United States Patent
Kim et al.

(10) Patent No.: US 11,649,277 B2
(45) Date of Patent: *May 16, 2023

(54) METHOD FOR TREATING SKIN DISEASES USING A HUMANIZED ANTIBODY THAT BINDS TO VIMENTIN

(71) Applicant: IMMUNEMED INC., Gangwon-do (KR)

(72) Inventors: Yoon-Won Kim, Gangwon-do (KR); Sungman Park, Gangwon-do (KR); Min Soo Kim, Gangwon-do (KR)

(73) Assignee: IMMUNEMED INC., Gangwon-Do (KR)

( * ) Notice: Subject to any disclaimer, the term of this patent is extended or adjusted under 35 U.S.C. 154(b) by 255 days.

This patent is subject to a terminal disclaimer.

(21) Appl. No.: 16/636,834

(22) PCT Filed: Aug. 30, 2018

(86) PCT No.: PCT/KR2018/010049
§ 371 (c)(1),
(2) Date: Feb. 5, 2020

(87) PCT Pub. No.: WO2019/045477
PCT Pub. Date: Mar. 7, 2019

(65) Prior Publication Data
US 2020/0362020 A1    Nov. 19, 2020

(30) Foreign Application Priority Data

Aug. 31, 2017  (KR) .................... 10-2017-0110924
Nov. 28, 2017  (WO) ................ PCT/KR2017/013706

(51) Int. Cl.
| | |
|---|---|
| *A61P 17/00* | (2006.01) |
| *C07K 16/18* | (2006.01) |
| *A61P 17/06* | (2006.01) |
| *A61P 17/04* | (2006.01) |
| *A61K 39/35* | (2006.01) |
| *A61P 37/08* | (2006.01) |
| *A61P 37/06* | (2006.01) |
| *A61K 39/00* | (2006.01) |
| *A61K 35/12* | (2015.01) |

(52) U.S. Cl.
CPC .............. *C07K 16/18* (2013.01); *A61K 39/35* (2013.01); *A61P 17/00* (2018.01); *A61P 17/04* (2018.01); *A61P 17/06* (2018.01); *A61P 37/06* (2018.01); *A61P 37/08* (2018.01); *A61K 2035/122* (2013.01); *A61K 2039/505* (2013.01); *C07K 2317/24* (2013.01); *C07K 2317/41* (2013.01); *C07K 2317/622* (2013.01)

(58) Field of Classification Search
None
See application file for complete search history.

(56) References Cited

U.S. PATENT DOCUMENTS

2004/0259112 A1    12/2004   Georges et al.

FOREIGN PATENT DOCUMENTS

| CA | 2988715 A1 | 12/2016 |
|---|---|---|
| EP | 1067142 A1 | 1/2001 |
| WO | WO 2016/200220 A1 | 12/2016 |

OTHER PUBLICATIONS

Li, .FJ. et al. J. Immunol. 199:1596-1605 (Year: 2017).*
Kinloch, A.J., et al. Arthrit. Rheum. 66;12:3359-3370 (Year: 2014).*
Snir, O., et al. Arthrit. Rheum. 62;1:44-52 (Year: 2010).*
Capriotti, K., et al. Dermatol. Ther.;5(4):247-252 (Year: 2015).*
Vora, R.V., et al. J. Clin. Diagn. Res.;9(11)1-2 (Year: 2015).*
Mor-vaknin et al: "Vimentin is secreted by activated macrophages", Nature Cell Biology, Macmillan Magazines Ltd, GB, vol. 5, Jan. 1, 2003 (Jan. 1, 2003), pp. 59-63.
Revishchin et al: "An immunohistochemical study of depigmented skin of vitiligo patients", Cell and Tissue Biology, Springer US, Boston, vol. 11, No. 4, Aug. 19, 2017 (Aug. 19, 2017). pp. 300-307.
Du, N. et al, "Cell surface vimentin is an attachment receptor for enterovirus 71", Journal of Virology, vol. 88, No. 10, pp. 5816-5833, May 2014.
Liang, J.-J. et al, "Vimentin binding is critical for infection by the virulent strain of Japanese encephalitis virus", Cellular Microbiology, 13(9), pp. 1358-1370, Jun. 27, 2011.
Hofmann, I. et al, "Interference in vimentin assembly in vitro by synthetic peptides derived from the vimentin head domain", Journal of Cell Science, vol. 101, pp. 687-700, 1992.
Office Action in Japanese Patent Application No. 2020-511948 dated Mar. 9, 2021.
Nippon Rinsho (Japanese Journal of Clinical Medicine), 1987, vol. 45, No. 10, pp. 2258-2262.

* cited by examiner

*Primary Examiner* — G. R. Ewoldt
(74) *Attorney, Agent, or Firm* — Knobbe, Martens, Olson & Bear LLP

(57) ABSTRACT

A method of treating skin diseases by administering a pharmaceutical composition including a humanized antibody which binds to vimentin.

4 Claims, 21 Drawing Sheets
Specification includes a Sequence Listing.

[FIG. 1]
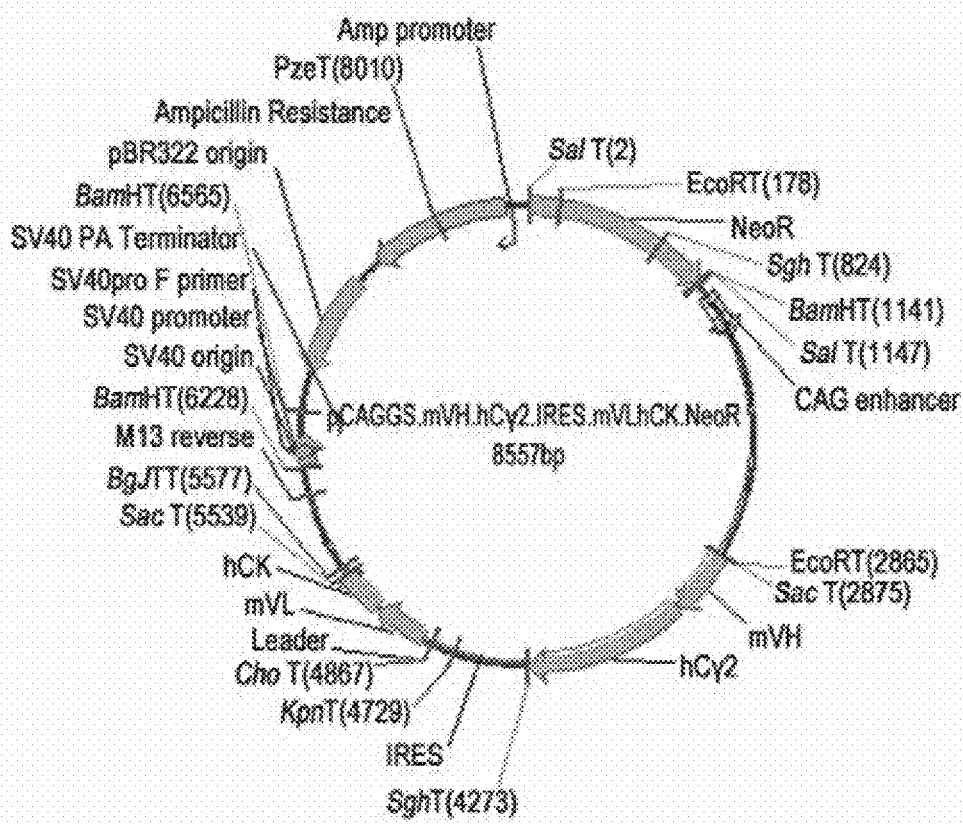
chVSF HC and LC
(simultaneous expression vectors)

[FIG. 2]
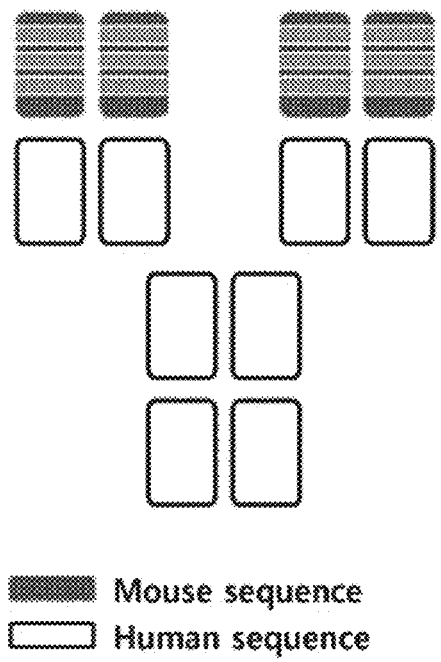
▬ Mouse sequence
☐ Human sequence
[FIG. 3]
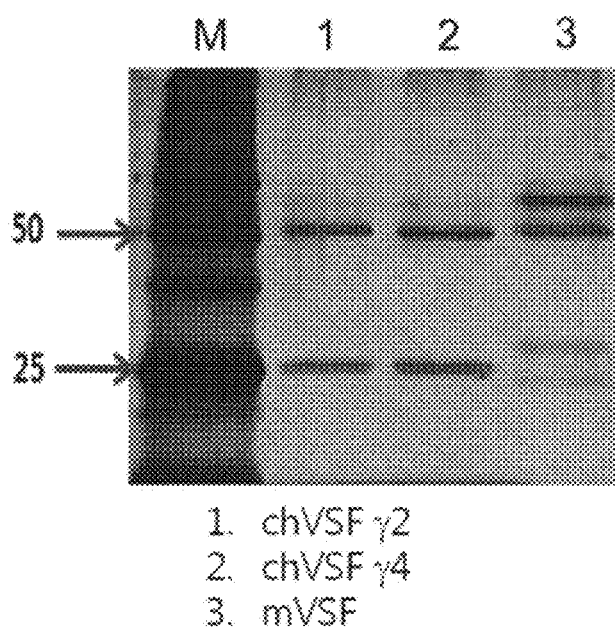
1. chVSF γ2
2. chVSF γ4
3. mVSF

[FIG. 4]    SEQ ID NO: 150

C GTCGAC GAGATCCAGCTGCAGCAGTCT

GAGATCCAGCTGCAGCAGTCT
GGAGCTGAGCTGGTGAAGCCTGGGGCTTCAGTGAAGATATCCTGCAAGGCTTCTGGTTACT
CATTCACTGGCTACAACATGAACTGGGTGAAGCAGAGCCATGGAAAGAGCCTTGAGTGGATT
GGAAATATTGATCCTTACTATGGTAGTACTACCTACAATCAGAAGTTCAAGGGCAAGGCCACA
TTGACTGTAGACAAATCTTCCAGCACAGCCTACATGCAGCTCAACAGCCTGACATCTGAGGA
CTCTGCAGTCTATTACTGTGCAAGAGAGACTGGGACGAGGGCTATGGACTACTGGGGTCAA
GGAACCTCAGTCACCGTCTCCTCA
CCTTGGAGTCAGTGGCAGAGGAGTCCACCTCCACCGAGACCACCTCC GCTGCG CCACCT
                                                CAGGA TGATCT GGTGGA
GGTGGCTCTGGTGGAGGTGGCTCTGACATCCAGATGACTCAGTC
                        GACATCCAGATGACTCAGTCTCCAGCCTCCCTATCTG
CATCTGTGGGAGAAACTGTCACCATGACATGTCGAGCAAGTGAGAATATTTACAGTAATTTAG
CATGGTATCAGCAGAAACAGGGAAAATCTCCTCAGCTCCTGGTCTATGTTGCAACAAACTTAG
CAGATGGTGTGCCATCAAGGTTCAGTGGCAGTGGATCAGGCACACAGTTTTCTCTGAAGATC
AACAGCCTGCAGCCTGAAGATTTTGGGAGTTATTACTGTCAACATTTTATGGTTCTCCTCGG
ACGTTCGGTGGAGGCACCAAGCTGGAAATCAAAC
                CCGTGGTTCGACCTTAGTTTGGAGCTCC

[FIG. 5]
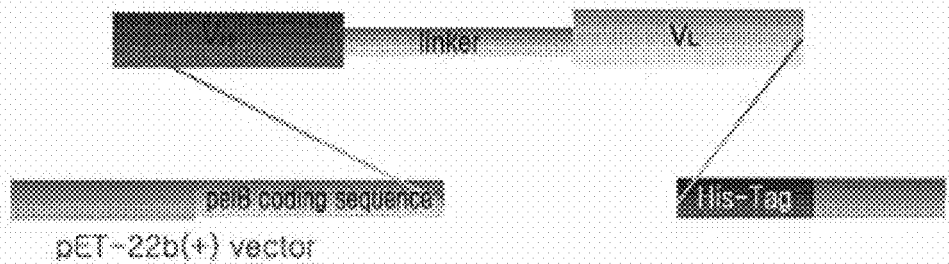
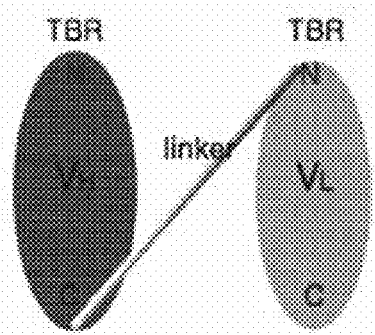

[FIG. 6]
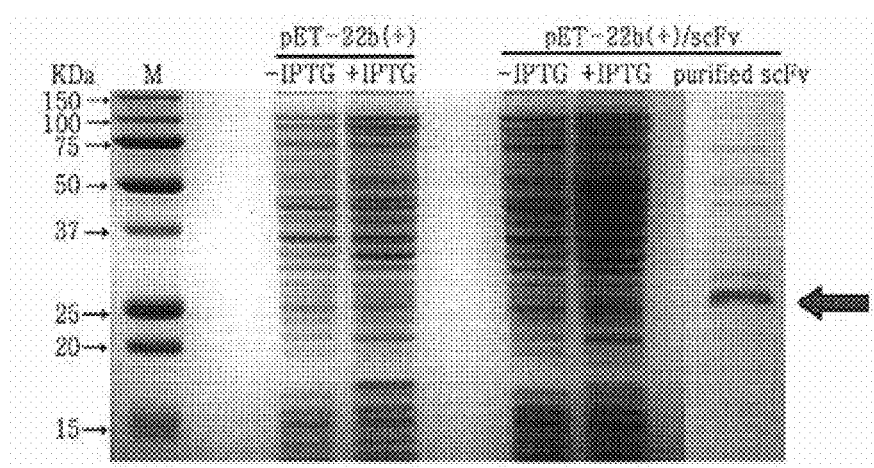
Lane 1: molecular weight marker.
Lane 2: pET-22b (+) (no induction).
Lane 3: pET-22b (+) (IPTG induction)
Lane 4: pET-22b (+)/scFv (no induction)
Lane 5: pET-22b (+)/scFv (IPTG induction)
Lane 6: purified scFv by Ni-NTA column (IPTG induction)

[FIG. 7]
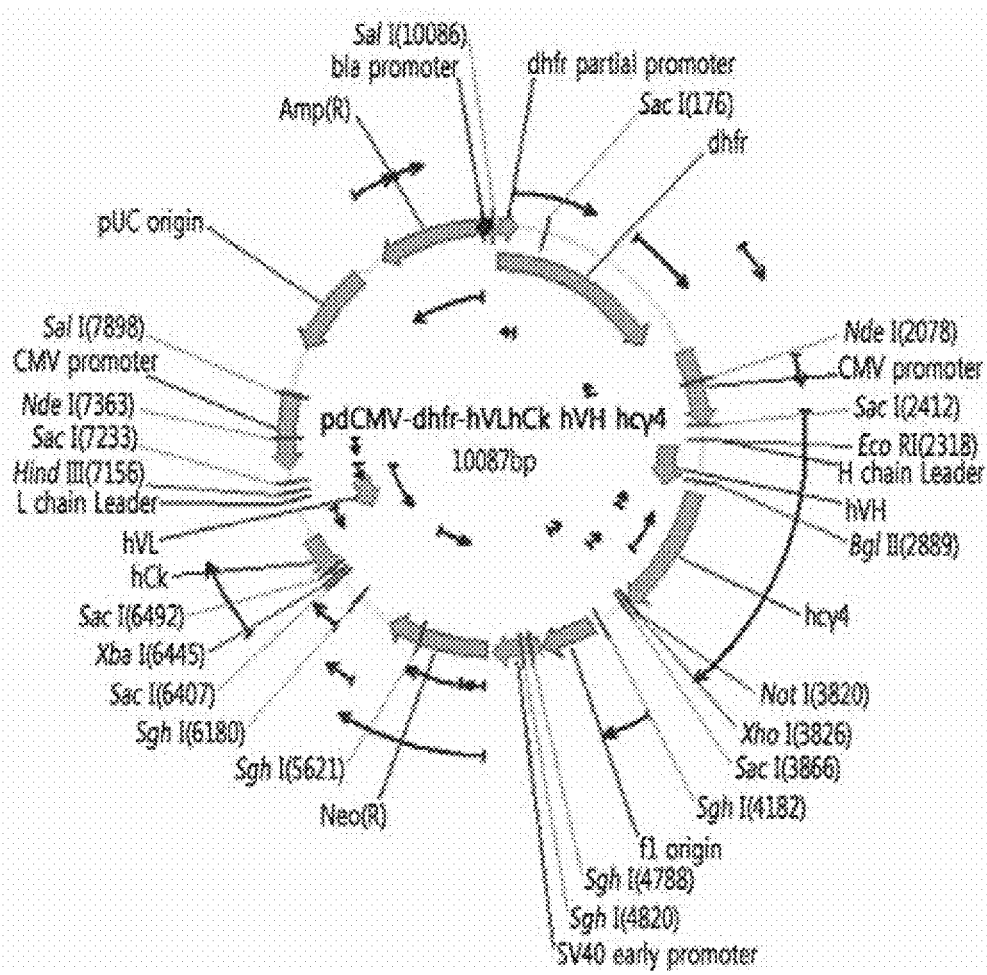
[FIG. 8]
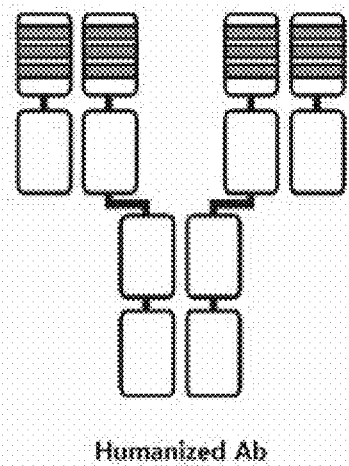
Humanized Ab

[FIG. 9]
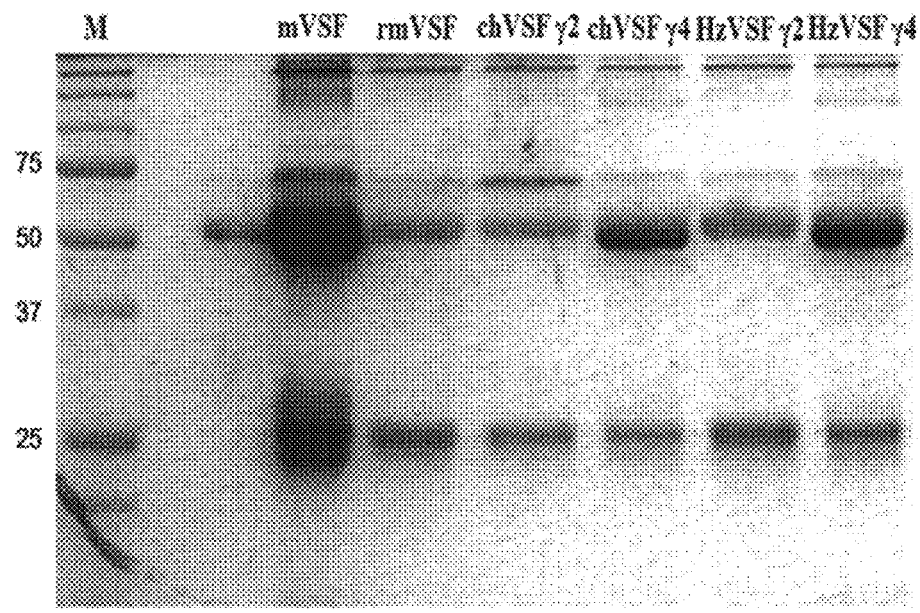
[FIG. 10]
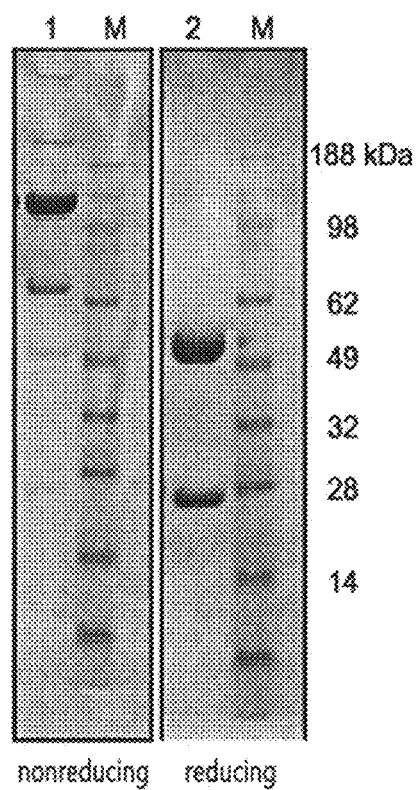

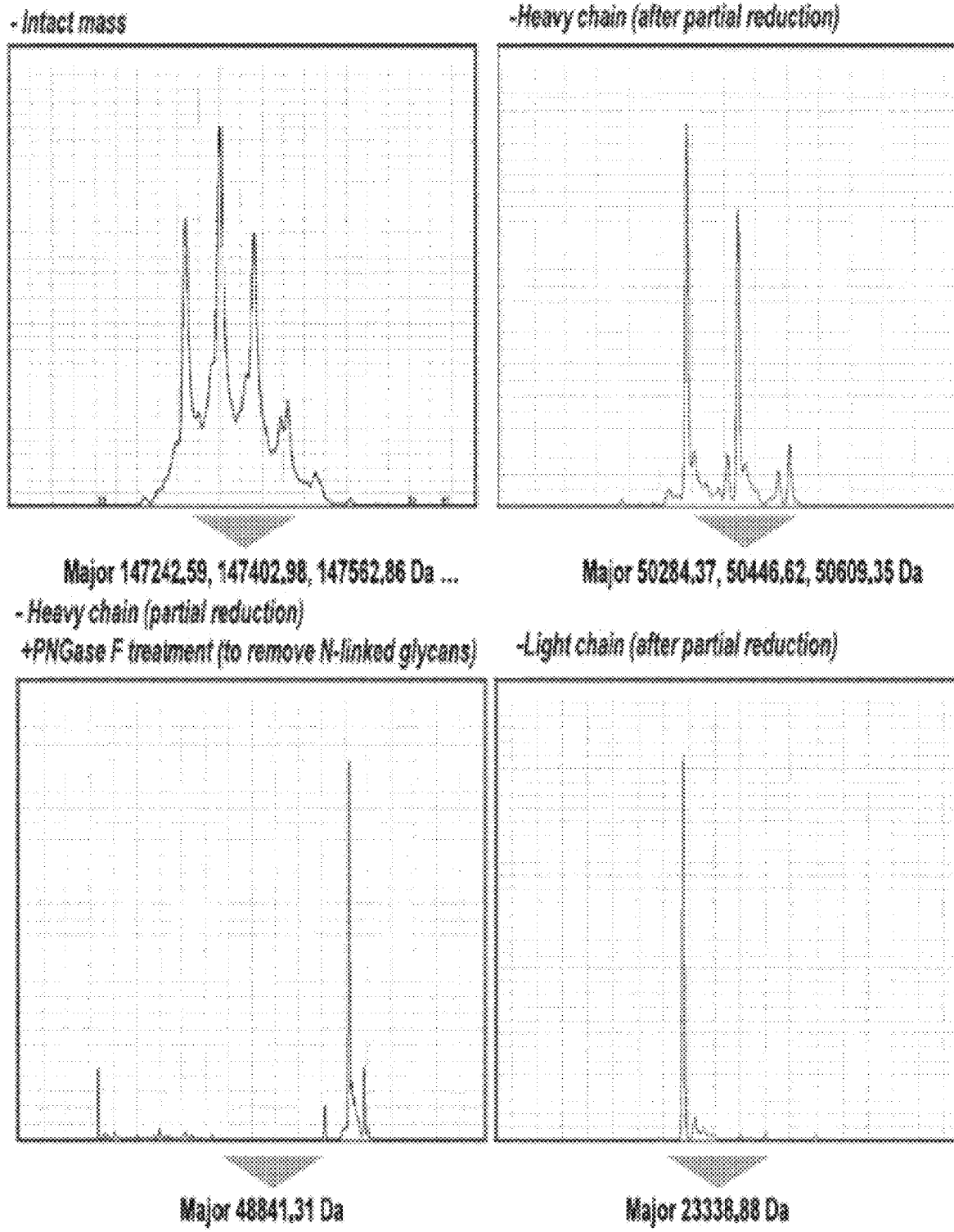

[FIG. 12]
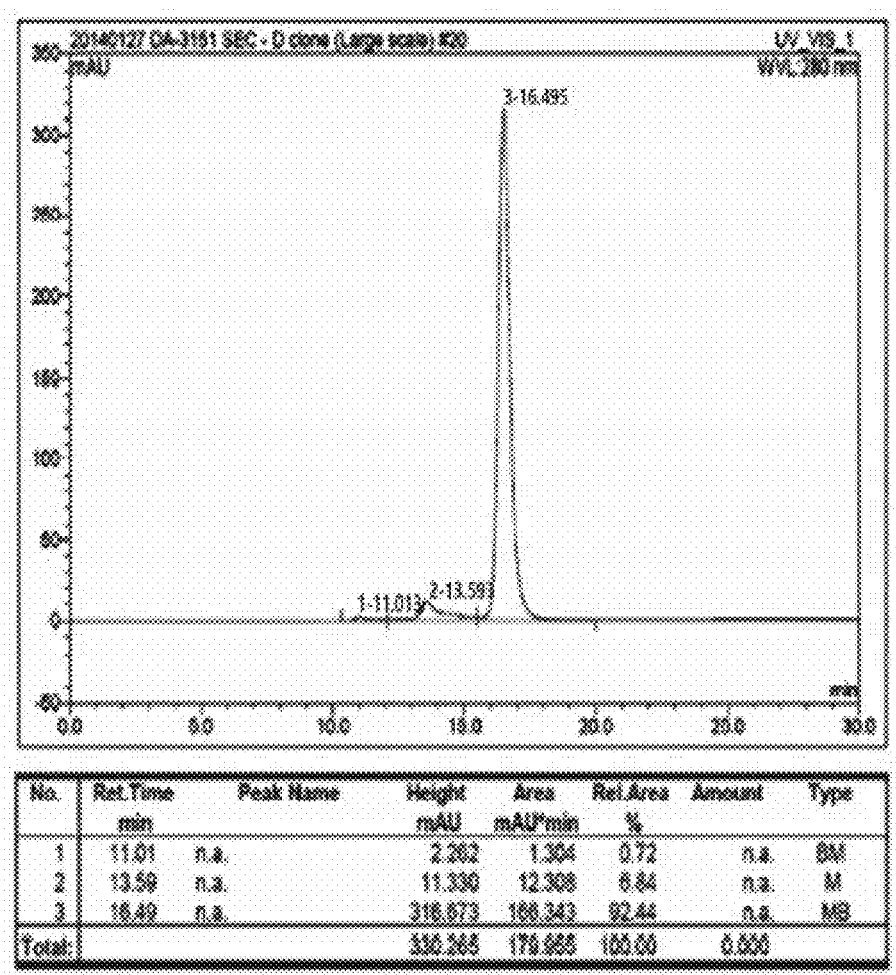

[FIG. 13]
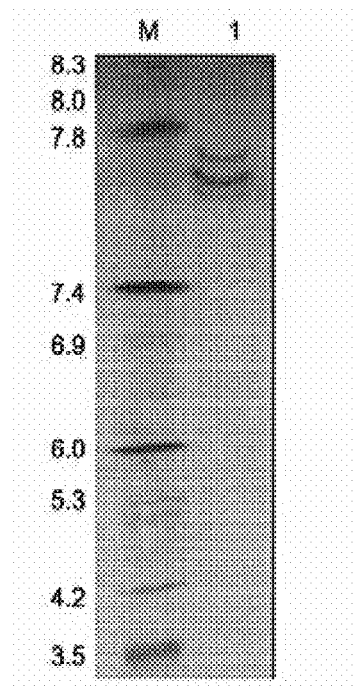
[FIG. 14]
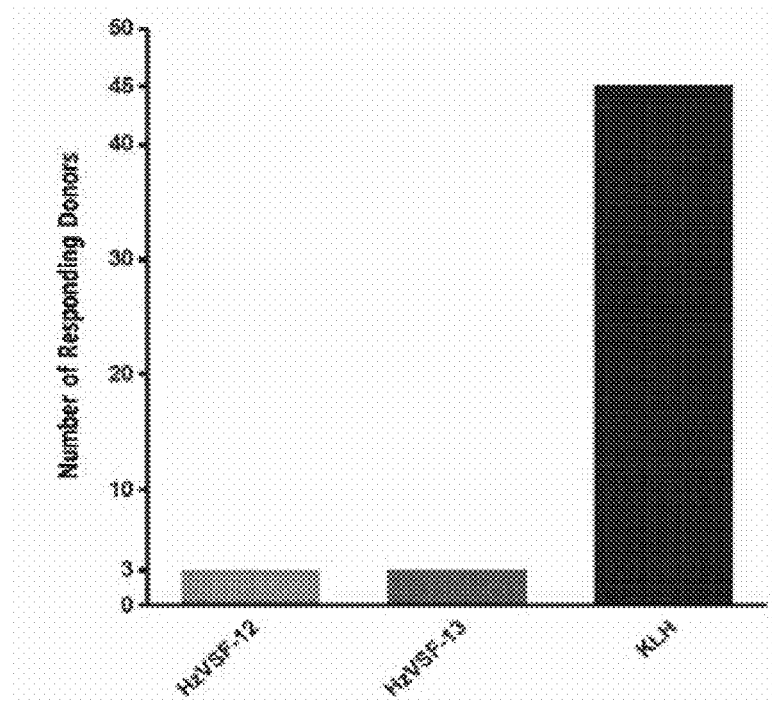

[FIG. 15]
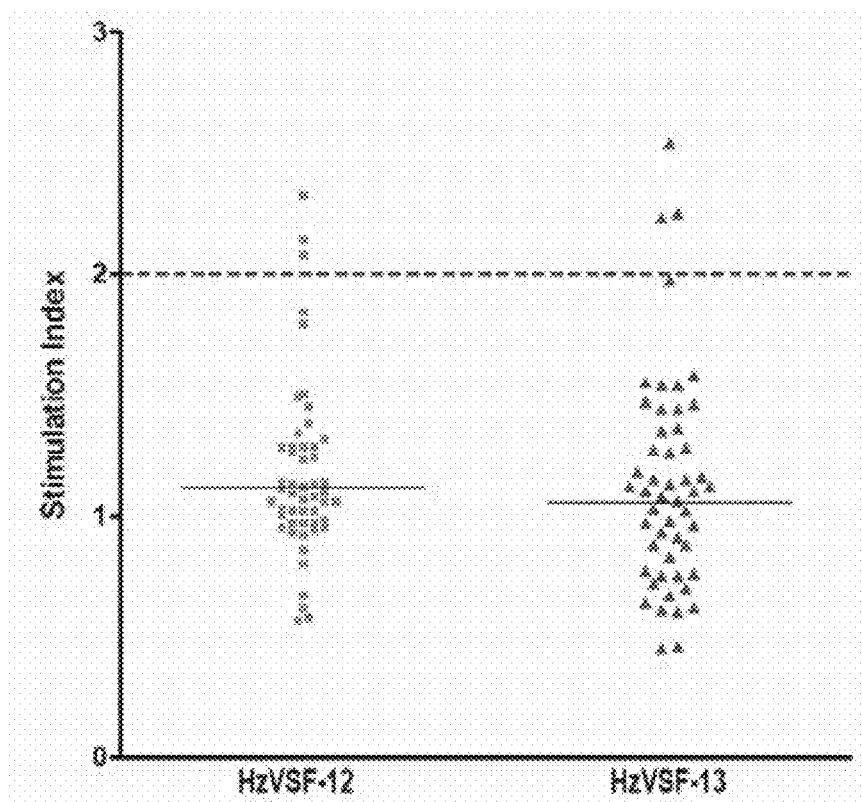

[FIG. 16]
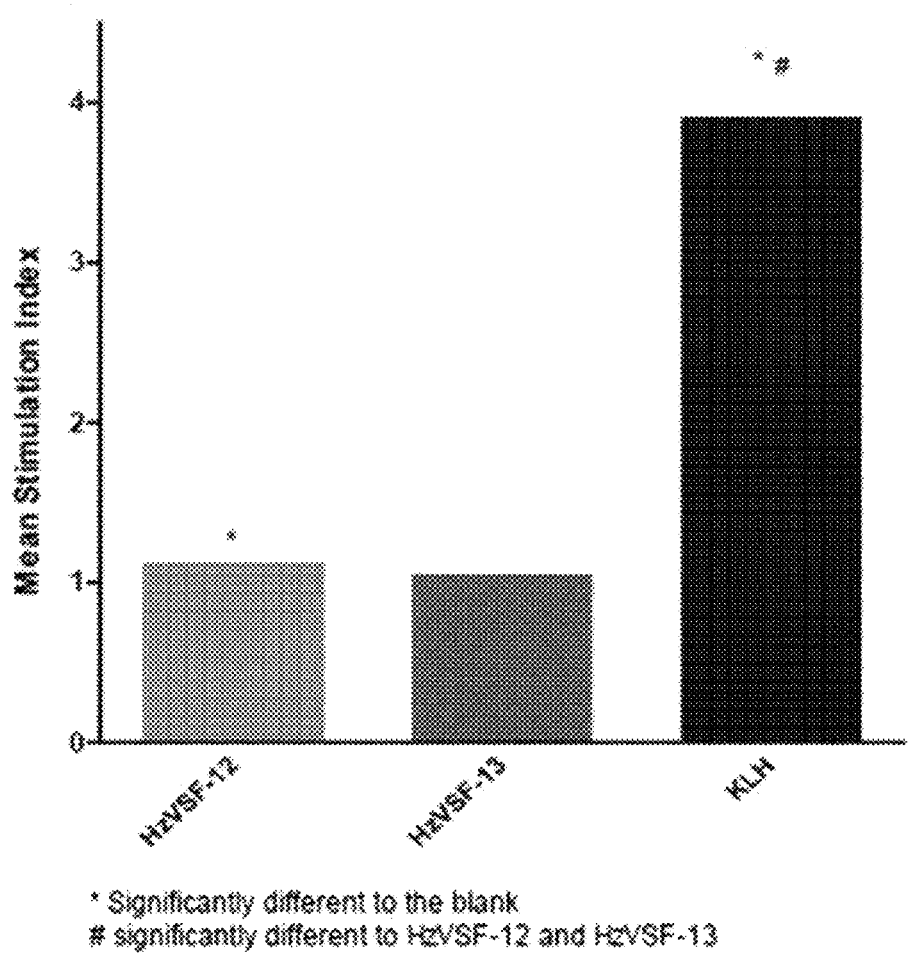

[FIG. 17]
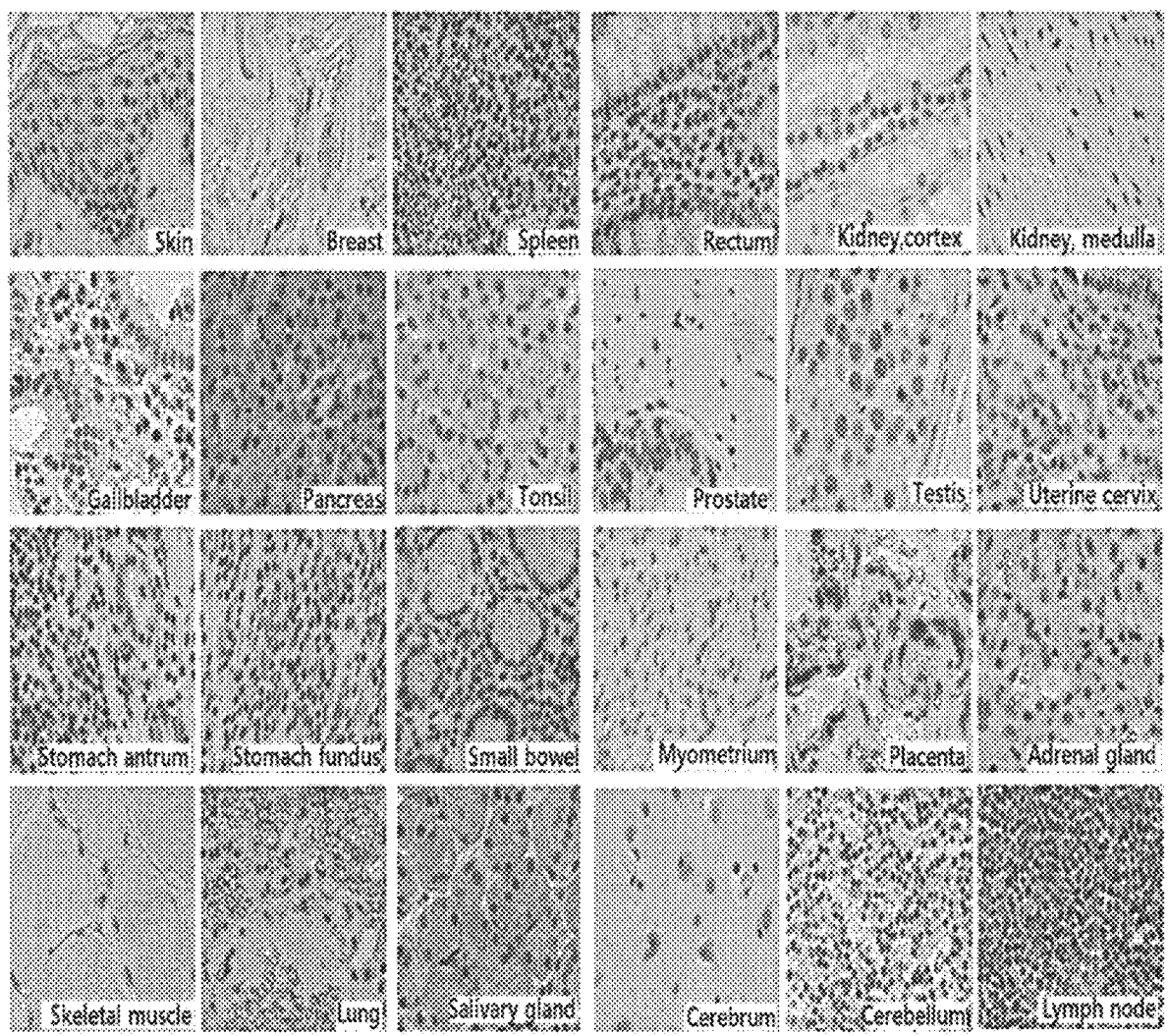

[FIG. 18]

| Disease | VR Expression (No. of positive case/No. of total case) | VR Expression (%) |
|---|---|---|
| Pityriasis rosea | 10/10 | 100 |
| Herpes zoster virus | 3/3 | 100 |
| Lichen simplex chronicus | 13/14 | 93 |
| Herpes simplex virus | 9/10 | 90 |
| Nummular eczema | 15/17 | 88 |
| Molluscum contagiosum | 10/14 | 71 |
| Psoriasis | 10/15 | 67 |
| Verruca vulgaris | 10/15 | 67 |
| Atopic dermatitis | 6/9 | 67 |
| Allergic contact dermatitis | 2/3 | 67 |
| Total | 88/110 | 80 |

[FIG. 19]
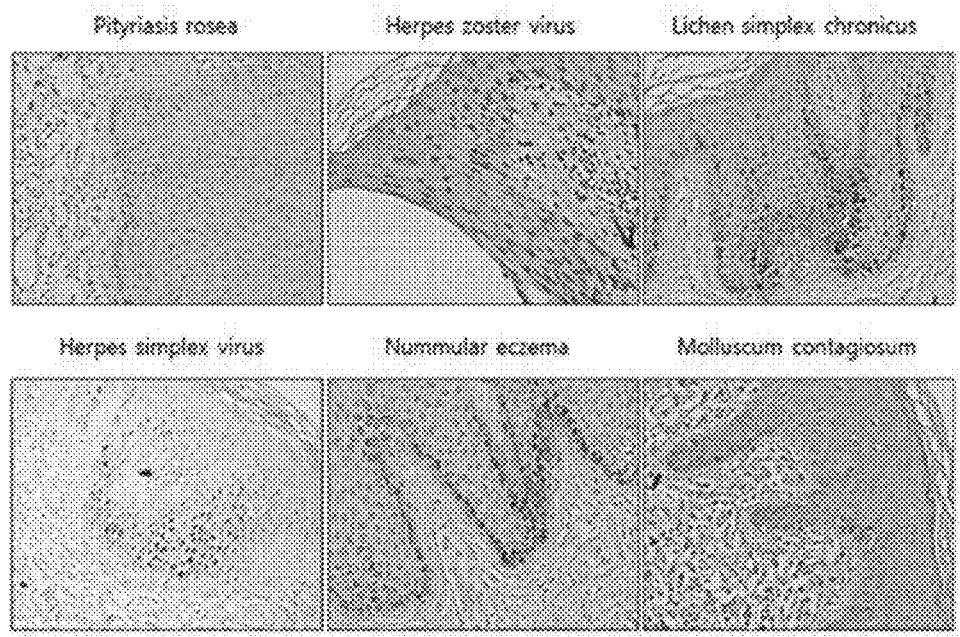
[FIG. 20]
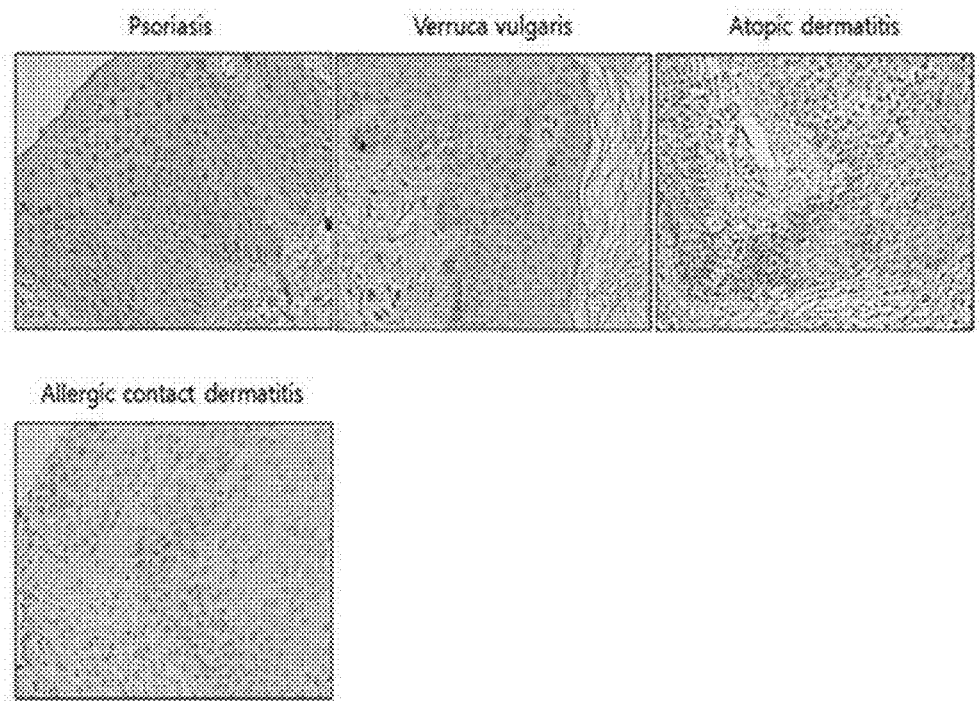

[FIG. 21]
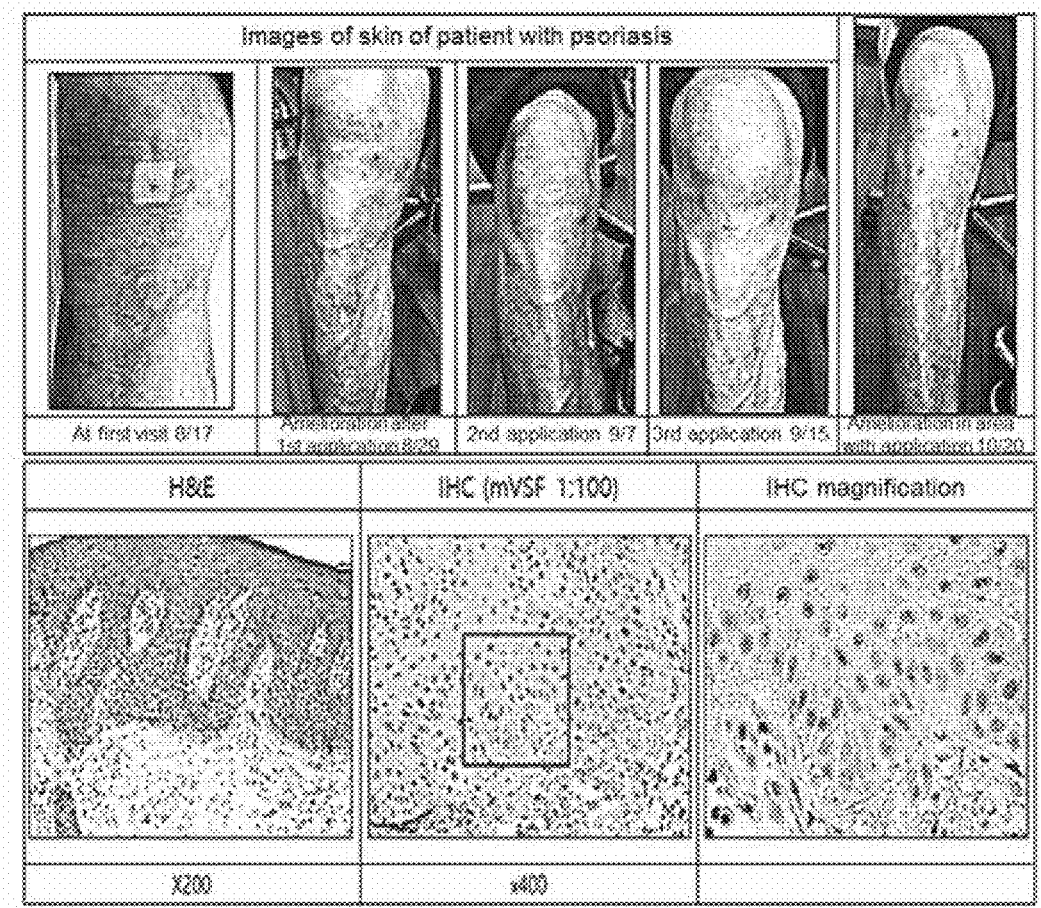

[FIG. 22]
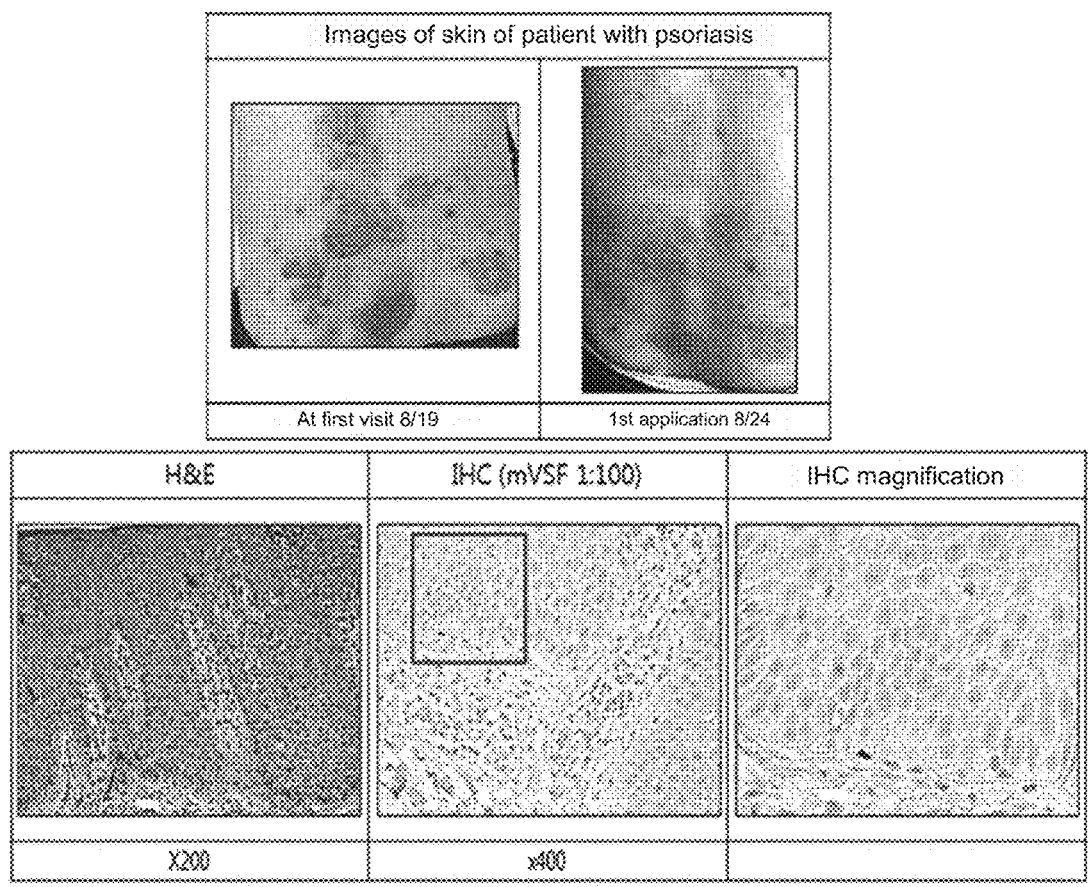

[FIG. 23]
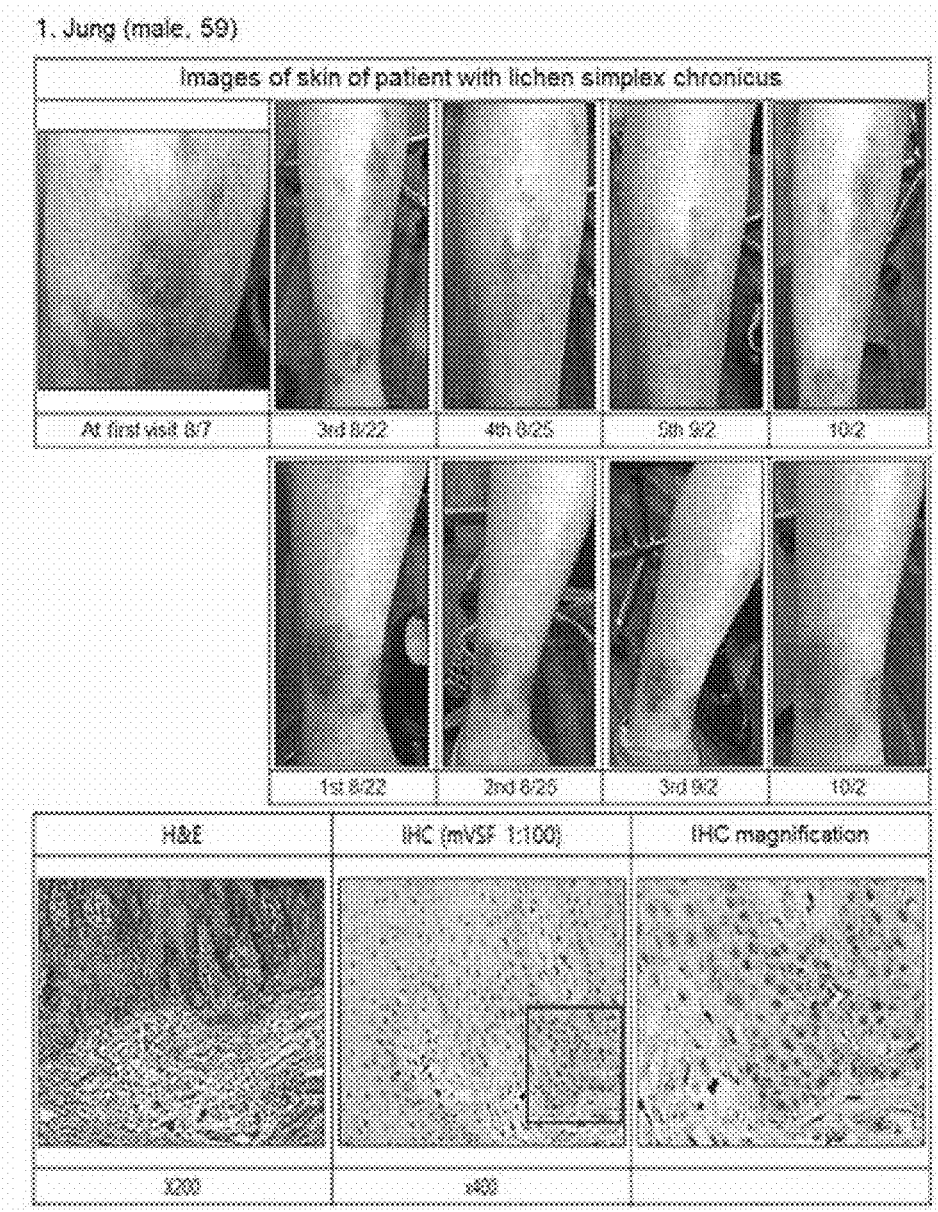

[FIG. 24]
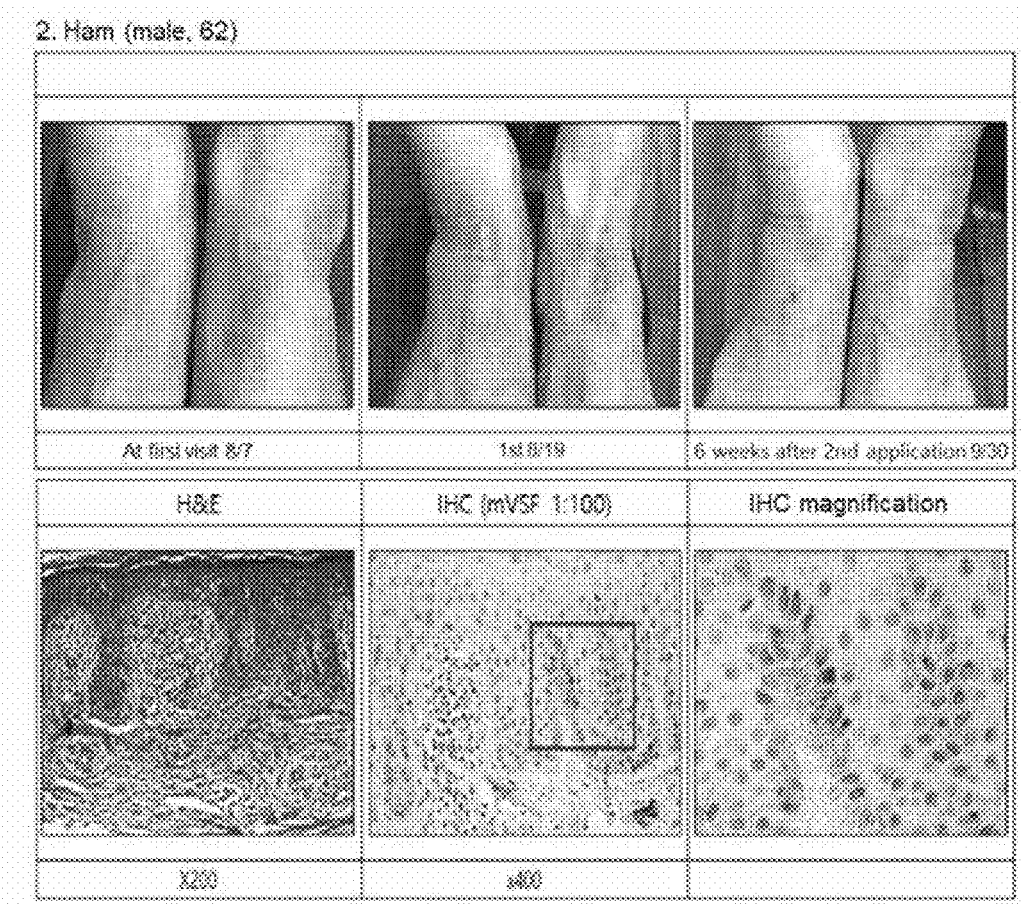

[FIG. 25]
3. Lee(male, 63)
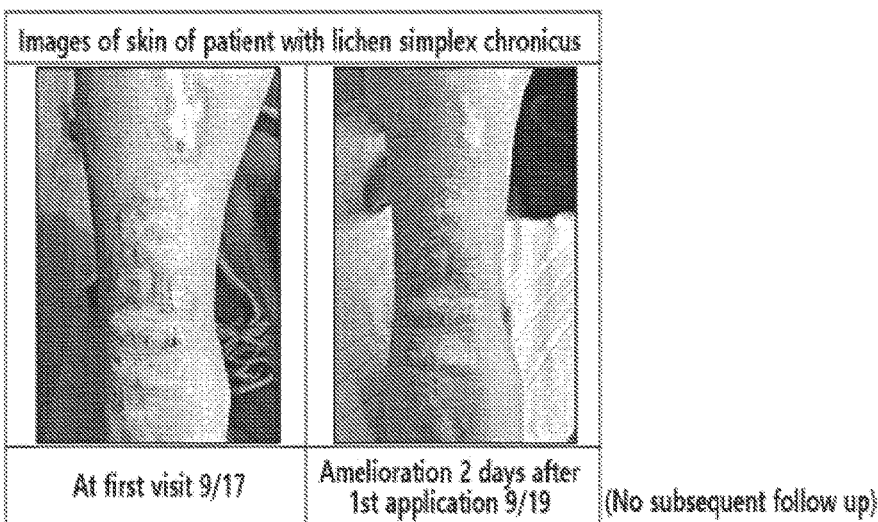
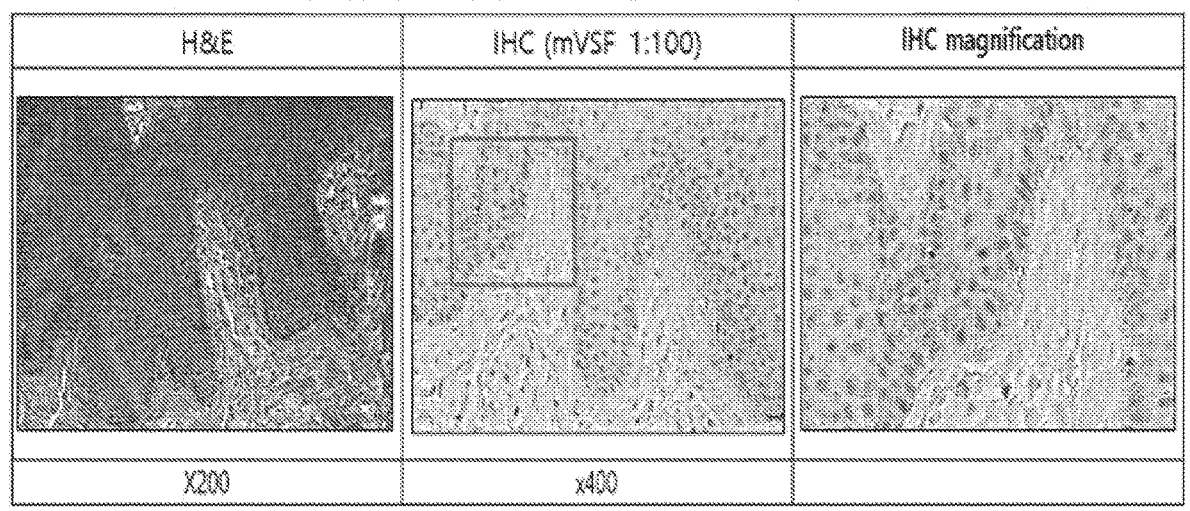
[FIG. 26]
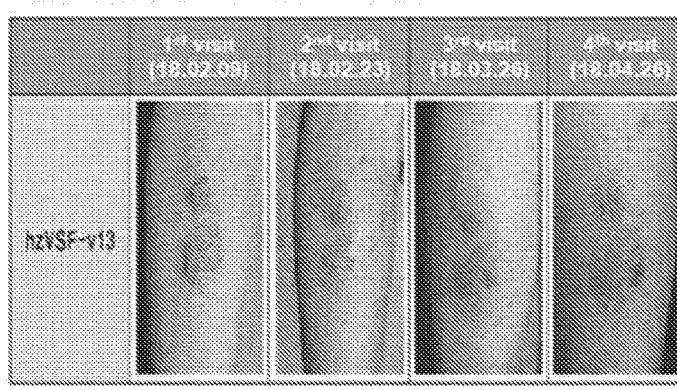

[FIG. 27]

|  |  |  | EASI/PASI hzVSF-v13 | | | EASI/PASI hzVSF-v13 |
|---|---|---|---|---|---|---|
|  |  |  | 1st | 2nd | 3rd |  |
| 001 | F/27 | Lichen simplex chronicus | 8 | 6 | 2 | -6 |
| 008 | M/47 | Lichen simplex chronicus | 9 | 7 | 6 | -3 |
| 002 | M/62 | nummular dermatitis | 11 | 8 | 4 | -7 |
| 003 | M/52 | nummular dermatitis | 5 | 1 | 1 | -4 |
| 011 | F/63 | nummular dermatitis | 9 | 5 | 4 | -5 |
| 006 | M/29 | eczema | 5 | 4 | 1 | -4 |
| 009 | M/52 | Atopic dermatitis | 10 | 5 | 4 | -6 |
| 012 | M/58 | dermatitis | 6 | 4 | 3 | -3 |
| 005 | F/32 | psoriasis | 7 | 6 | 3 | -4 |
| 007 | M/71 | severe psoriasis vulgaris | 10 | 6 | 5 | -5 |
| 010 | M/66 | psoriasis | 7 | 7 | 3 | -4 |

Difference from day 0, p value 0.4569
paired-t p 0.0002035

[FIG. 28]

|  |  |  | VAS hzVSF-v13 | | | VAS hzVSF-v13 |
|---|---|---|---|---|---|---|
|  |  |  | 1st | 2nd | 3rd |  |
| 001 | F/27 | Lichen simplex chronicus | 7 | 5 | 1 | -6 |
| 008 | M/47 | Lichen simplex chronicus | 6 | 4 | 4 | -2 |
| 002 | M/62 | nummular dermatitis | 10 | 9 | 5 | -5 |
| 003 | M/52 | nummular dermatitis | 6 | 2 | 1 | -5 |
| 011 | F/63 | nummular dermatitis | 8 | 4 | 3 | -5 |
| 006 | M/29 | eczema | 5 | 5 | 2 | -3 |
| 009 | M/52 | Atopic dermatitis | 6 | 3 | 2 | -4 |
| 012 | M/58 | dermatitis | 5 | 4 | 4 | -1 |
| 005 | F/32 | psoriasis | 4 | 2 | 1 | -3 |
| 007 | M/71 | severe psoriasis vulgaris | 8 | 6 | 3 | -5 |
| 010 | M/66 | psoriasis | 7 | 8 | 4 | -3 |

Difference from day 0, p value 0.491
paired-t p 0.0053038

SEQUENCE LISTING

```
<160> NUMBER OF SEQ ID NOS: 162

<210> SEQ ID NO 1
<211> LENGTH: 153
<212> TYPE: PRT
<213> ORGANISM: Artificial Sequence
<220> FEATURE:
<223> OTHER INFORMATION: Isoalted Vimentin fragment (142-294)

<400> SEQUENCE: 1

Gly Lys Ser Arg Leu Gly Asp Leu Tyr Glu Glu Met Arg Glu Leu
1               5                   10                  15

Arg Arg Gln Val Asp Gln Leu Thr Asn Asp Lys Ala Arg Val Glu Val
                20                  25                  30

Glu Arg Asp Asn Leu Ala Glu Asp Ile Met Arg Leu Arg Glu Lys Leu
                35                  40                  45

Gln Glu Glu Met Leu Gln Arg Glu Glu Ala Glu Asn Thr Leu Gln Ser
            50                  55                  60

Phe Arg Gln Asp Val Asp Asn Ala Ser Leu Ala Arg Leu Asp Leu Glu
65                  70                  75                  80

Arg Lys Val Glu Ser Leu Gln Glu Glu Ile Ala Phe Leu Lys Lys Leu
                    85                  90                  95

His Glu Glu Glu Ile Gln Glu Leu Gln Ala Gln Ile Gln Glu Gln His
                100                 105                 110

Val Gln Ile Asp Val Asp Val Ser Lys Pro Asp Leu Thr Ala Ala Leu
                115                 120                 125

Arg Asp Val Arg Gln Gln Tyr Glu Ser Val Ala Ala Lys Asn Leu Gln
    130                 135                 140

Glu Ala Glu Glu Trp Tyr Lys Ser Lys
145                 150

<210> SEQ ID NO 2
<211> LENGTH: 5
<212> TYPE: PRT
<213> ORGANISM: Artificial Sequence
<220> FEATURE:
<223> OTHER INFORMATION: CDR1 of heavy chain

<400> SEQUENCE: 2

Gly Tyr Asn Met Asn
1               5

<210> SEQ ID NO 3
<211> LENGTH: 17
<212> TYPE: PRT
<213> ORGANISM: Artificial Sequence
<220> FEATURE:
<223> OTHER INFORMATION: CDR2 of heavy chain

<400> SEQUENCE: 3

Asn Ile Asp Pro Tyr Tyr Gly Ser Thr Thr Tyr Ala Gln Lys Phe Gln
```

```
1               5                   10                  15
Gly

<210> SEQ ID NO 4
<211> LENGTH: 9
<212> TYPE: PRT
<213> ORGANISM: Artificial Sequence
<220> FEATURE:
<223> OTHER INFORMATION: CDR3 of heavy chain

<400> SEQUENCE: 4

Glu Thr Gly Thr Arg Ala Met Asp Tyr
1               5

<210> SEQ ID NO 5
<211> LENGTH: 11
<212> TYPE: PRT
<213> ORGANISM: Artificial Sequence
<220> FEATURE:
<223> OTHER INFORMATION: CDR1 of light chain

<400> SEQUENCE: 5

Arg Ala Ser Glu Asn Ile Tyr Ser Asn Leu Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: CDR2 of light chain

<400> SEQUENCE: 6

Val Ala Thr Asn Leu Ala Asp
1               5

<210> SEQ ID NO 7
<211> LENGTH: 9
<212> TYPE: PRT
<213> ORGANISM: Artificial Sequence
<220> FEATURE:
<223> OTHER INFORMATION: CDR3 of light chain

<400> SEQUENCE: 7

Gln His Phe Tyr Gly Ser Pro Arg Thr
1               5

<210> SEQ ID NO 8
<211> LENGTH: 169
<212> TYPE: PRT
<213> ORGANISM: Artificial Sequence
<220> FEATURE:
<223> OTHER INFORMATION: mVSF_VL

<400> SEQUENCE: 8

Met Ser Val Pro Thr Gln Val Leu Gly Leu Leu Leu Trp Leu Thr
1               5                   10                  15

Gly Asn Glu Asp Ser Thr Arg Asn Leu Leu Ser Phe Leu His Ser Val
            20                  25                  30

Leu Leu Gly Leu Asn Glu Asn Ser Leu Val Arg Glu Leu Ile Met Trp
        35                  40                  45

Val Ser Val Phe Asn Phe Pro Ile Val Gly Ala Arg Cys Asp Ile Gln
    50                  55                  60

Met Thr Gln Ser Pro Ala Ser Leu Ser Ala Ser Val Gly Glu Thr Val
```

```
                65                   70                  75                  80
Thr Met Thr Cys Arg Ala Ser Glu Asn Ile Tyr Ser Asn Leu Ala Trp
                    85                  90                  95

Tyr Gln Gln Lys Gln Gly Lys Ser Pro Gln Leu Leu Val Tyr Val Ala
                100                 105                 110

Thr Asn Leu Ala Asp Gly Val Pro Ser Arg Phe Ser Gly Ser Gly Ser
                115                 120                 125

Gly Thr Gln Phe Ser Leu Lys Ile Asn Ser Leu Gln Pro Glu Asp Phe
            130                 135                 140

Gly Ser Tyr Tyr Cys Gln His Phe Tyr Gly Ser Pro Arg Thr Phe Gly
145                 150                 155                 160

Gly Gly Thr Lys Leu Glu Ile Lys Arg
                165
```

```
<210> SEQ ID NO 9
<211> LENGTH: 118
<212> TYPE: PRT
<213> ORGANISM: Artificial Sequence
<220> FEATURE:
<223> OTHER INFORMATION: mVSF_VH

<400> SEQUENCE: 9

Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
                20                  25                  30

Asn Met Asn Trp Val Lys Gln Ser His Gly Lys Ser Leu Glu Trp Ile
            35                  40                  45

Gly Asn Ile Asp Pro Tyr Tyr Gly Ser Thr Thr Tyr Asn Gln Lys Phe
        50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Glu Thr Gly Thr Arg Ala Met Asp Tyr Trp Gly Gln Gly Thr
                100                 105                 110

Ser Val Thr Val Ser Ser
        115
```

```
<210> SEQ ID NO 10
<211> LENGTH: 118
<212> TYPE: PRT
<213> ORGANISM: Artificial Sequence
<220> FEATURE:
<223> OTHER INFORMATION: HzVSF_VH_WT

<400> SEQUENCE: 10

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Asn Met Asn Trp Val Arg Gln Ala Pro Gly Lys Gly Leu Glu Trp Met
            35                  40                  45

Gly Asn Ile Asp Pro Tyr Tyr Gly Ser Thr Thr Tyr Ala Gln Lys Phe
        50                  55                  60

Gln Gly Arg Val Thr Met Thr Val Asp Lys Ser Ile Ser Thr Ala Tyr
65                  70                  75                  80
```

```
Met Glu Leu Ser Arg Leu Arg Ser Asp Asp Thr Ala Val Tyr Tyr Cys
            85                  90                  95

Ala Arg Glu Thr Gly Thr Arg Ala Met Asp Tyr Trp Gly Gln Gly Thr
        100                 105                 110

Leu Val Thr Val Ser Ser
        115

<210> SEQ ID NO 11
<211> LENGTH: 445
<212> TYPE: PRT
<213> ORGANISM: Artificial Sequence
<220> FEATURE:
<223> OTHER INFORMATION: HzVSF_HC_WT - HzVSF hVH.hCgamma4_WT

<400> SEQUENCE: 11

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Glu Thr Gly Thr Arg Ala Met Asp Tyr Trp Gly Gln Gly Thr
        100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Lys Thr Tyr Thr Cys Asn Val Asp His Lys Pro Ser
    195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
        260                 265                 270

Phe Asn Trp Tyr Val Asp Gly Val Glu Val His Asn Ala Lys Thr Lys
    275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320
```

```
Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
        420                 425                 430

His Tyr Thr Gln Lys Ser Leu Ser Leu Ser Leu Gly Lys
    435                 440                 445

<210> SEQ ID NO 12
<211> LENGTH: 107
<212> TYPE: PRT
<213> ORGANISM: Artificial Sequence
<220> FEATURE:
<223> OTHER INFORMATION: HzVSF_VL_WT

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105

<210> SEQ ID NO 13
<211> LENGTH: 214
<212> TYPE: PRT
<213> ORGANISM: Artificial Sequence
<220> FEATURE:
<223> OTHER INFORMATION: HzVSF_LC_WT

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln His Phe Tyr Gly Ser Pro Arg
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 14
<211> LENGTH: 17
<212> TYPE: PRT
<213> ORGANISM: Artificial Sequence
<220> FEATURE:
<223> OTHER INFORMATION: CDR2 of heavy chain

<400> SEQUENCE: 14

Asn Ile Asp Pro Tyr Tyr Gly Ser Asp Thr Tyr Ala Gln Lys Phe Gln
1               5                   10                  15
Gly

<210> SEQ ID NO 15
<211> LENGTH: 8
<212> TYPE: PRT
<213> ORGANISM: Artificial Sequence
<220> FEATURE:
<223> OTHER INFORMATION: CDR3 of heavy chain

<400> SEQUENCE: 15

Glu Thr Gly Asn Arg Ala Met Asp
1               5

<210> SEQ ID NO 16
<211> LENGTH: 7
<212> TYPE: PRT
<213> ORGANISM: Artificial Sequence
<220> FEATURE:
<223> OTHER INFORMATION: CDR2 of light chain

<400> SEQUENCE: 16

Val Ala Asp Asn Leu Ala Asp
1               5

<210> SEQ ID NO 17
<211> LENGTH: 7
<212> TYPE: PRT
<213> ORGANISM: Artificial Sequence
<220> FEATURE:
<223> OTHER INFORMATION: CDR2 of light chain

<400> SEQUENCE: 17
```

Val Ala Asp Asn Leu Gly Asp
1               5

<210> SEQ ID NO 18
<211> LENGTH: 7
<212> TYPE: PRT
<213> ORGANISM: Artificial Sequence
<220> FEATURE:
<223> OTHER INFORMATION: CDR2 of light chain

<400> SEQUENCE: 18

Val Ala Asp Asn Arg Gly Asp
1               5

<210> SEQ ID NO 19
<211> LENGTH: 9
<212> TYPE: PRT
<213> ORGANISM: Artificial Sequence
<220> FEATURE:
<223> OTHER INFORMATION: CDR3 of light chain

<400> SEQUENCE: 19

Gln His Phe Tyr Gly Thr Pro Arg Thr
1               5

<210> SEQ ID NO 20
<211> LENGTH: 30
<212> TYPE: PRT
<213> ORGANISM: Artificial Sequence
<220> FEATURE:
<223> OTHER INFORMATION: FR1 of heavy chain

<400> SEQUENCE: 20

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 21
<211> LENGTH: 14
<212> TYPE: PRT
<213> ORGANISM: Artificial Sequence
<220> FEATURE:
<223> OTHER INFORMATION: FR2 of heavy chain

<400> SEQUENCE: 21

Trp Val Arg Gln Ala Pro Gly Lys Gly Leu Glu Trp Met Gly
1               5                   10

<210> SEQ ID NO 22
<211> LENGTH: 32
<212> TYPE: PRT
<213> ORGANISM: Artificial Sequence
<220> FEATURE:
<223> OTHER INFORMATION: FR3 of heavy chain

<400> SEQUENCE: 22

Arg Val Thr Met Thr Val Asp Lys Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 23
<211> LENGTH: 11
<212> TYPE: PRT
<213> ORGANISM: Artificial Sequence
<220> FEATURE:
<223> OTHER INFORMATION: FR4 of heavy chain

<400> SEQUENCE: 23

Trp Gly Gln Gly Thr Leu Val Thr Val Ser Ser
1               5                   10

<210> SEQ ID NO 24
<211> LENGTH: 23
<212> TYPE: PRT
<213> ORGANISM: Artificial Sequence
<220> FEATURE:
<223> OTHER INFORMATION: FR1 of light chain

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 25
<211> LENGTH: 15
<212> TYPE: PRT
<213> ORGANISM: Artificial Sequence
<220> FEATURE:
<223> OTHER INFORMATION: FR2 of light chain

<400> SEQUENCE: 25

Trp Tyr Gln Gln Lys Pro Gly Lys Ala Pro Lys Leu Leu Ile Tyr
1               5                   10                  15

<210> SEQ ID NO 26
<211> LENGTH: 32
<212> TYPE: PRT
<213> ORGANISM: Artificial Sequence
<220> FEATURE:
<223> OTHER INFORMATION: FR3 of light chain

<400> SEQUENCE: 26

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 27
<211> LENGTH: 10
<212> TYPE: PRT
<213> ORGANISM: Artificial Sequence
<220> FEATURE:
<223> OTHER INFORMATION: FR4 of light chain

<400> SEQUENCE: 27

Phe Gly Gly Gly Thr Lys Val Glu Ile Lys
1               5                   10

<210> SEQ ID NO 28
<211> LENGTH: 32
<212> TYPE: PRT
<213> ORGANISM: Artificial Sequence
<220> FEATURE:
<223> OTHER INFORMATION: FR3 of heavy chain

<400> SEQUENCE: 28

Arg Val Thr Met Thr Val Asp Thr Ser Ala Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 29
<211> LENGTH: 445
<212> TYPE: PRT
<213> ORGANISM: Artificial Sequence
<220> FEATURE:
<223> OTHER INFORMATION: HzVSF_a1_gamma4

<400> SEQUENCE: 29

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

```
Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 30
<211> LENGTH: 445
<212> TYPE: PRT
<213> ORGANISM: Artificial Sequence
<220> FEATURE:
<223> OTHER INFORMATION: HzVSF_a2_gamma4

<400> SEQUENCE: 30

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Ile
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270
```

Phe Asn Trp Tyr Val Asp Gly Val Glu Val His Asn Ala Lys Thr Lys
    275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 31
<211> LENGTH: 445
<212> TYPE: PRT
<213> ORGANISM: Artificial Sequence
<220> FEATURE:
<223> OTHER INFORMATION: HzVSF_a3_gamma4

<400> SEQUENCE: 31

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Ile
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 32
<211> LENGTH: 118
<212> TYPE: PRT
<213> ORGANISM: Artificial Sequence
<220> FEATURE:
<223> OTHER INFORMATION: HzVSF_VH_V1

<400> SEQUENCE: 32

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser
        115

<210> SEQ ID NO 33
<211> LENGTH: 445
<212> TYPE: PRT
<213> ORGANISM: Artificial Sequence
<220> FEATURE:
<223> OTHER INFORMATION: HzVSF_HC_V1

<400> SEQUENCE: 33

Glu Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 34
<211> LENGTH: 107
<212> TYPE: PRT
<213> ORGANISM: Artificial Sequence
<220> FEATURE:
<223> OTHER INFORMATION: HzVSF_VL_V1

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105

<210> SEQ ID NO 35
<211> LENGTH: 214
<212> TYPE: PRT
<213> ORGANISM: Artificial Sequence
<220> FEATURE:
<223> OTHER INFORMATION: HzVSF_LC_V1

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys Arg Thr Val Ala Ala
            100                 105                 110

-continued

```
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 36
<211> LENGTH: 118
<212> TYPE: PRT
<213> ORGANISM: Artificial Sequence
<220> FEATURE:
<223> OTHER INFORMATION: HzVSF_VH_V2

<400> SEQUENCE: 36

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Asn Met Asn Trp Val Arg Gln Ala Pro Gly Lys Gly Leu Glu Trp Met
        35                  40                  45
Gly Asn Ile Asp Pro Tyr Tyr Gly Ser Thr Thr Tyr Ala Gln Lys Phe
    50                  55                  60
Gln Gly Arg Val Thr Met Thr Val Asp Lys Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Glu Thr Gly Thr Arg Ala Met Asp Tyr Trp Gly Gln Gly Thr
            100                 105                 110
Leu Val Thr Val Ser Ser
        115
```

<210> SEQ ID NO 37
<211> LENGTH: 445
<212> TYPE: PRT
<213> ORGANISM: Artificial Sequence
<220> FEATURE:
<223> OTHER INFORMATION: HzVSF_HC_V2

<400> SEQUENCE: 37

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Asn Met Asn Trp Val Arg Gln Ala Pro Gly Lys Gly Leu Glu Trp Met
        35                  40                  45
Gly Asn Ile Asp Pro Tyr Tyr Gly Ser Thr Thr Tyr Ala Gln Lys Phe
    50                  55                  60
Gln Gly Arg Val Thr Met Thr Val Asp Lys Ser Ile Ser Thr Ala Tyr
```

```
                65                  70                  75                  80
Met Glu Leu Ser Arg Leu Arg Ser Asp Asp Thr Ala Val Tyr Tyr Cys
                        85                  90                  95

Ala Arg Glu Thr Gly Thr Arg Ala Met Asp Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
                180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
            435                 440                 445

<210> SEQ ID NO 38
<211> LENGTH: 107
<212> TYPE: PRT
<213> ORGANISM: Artificial Sequence
<220> FEATURE:
<223> OTHER INFORMATION: HzVSF_VL_V2
```

<400> SEQUENCE: 38

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Leu Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105
```

<210> SEQ ID NO 39
<211> LENGTH: 214
<212> TYPE: PRT
<213> ORGANISM: Artificial Sequence
<220> FEATURE:
<223> OTHER INFORMATION: HzVSF_LC_V2

<400> SEQUENCE: 39

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Leu Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 40
<211> LENGTH: 118
<212> TYPE: PRT

<213> ORGANISM: Artificial Sequence
<220> FEATURE:
<223> OTHER INFORMATION: HzVSF_VH_V3

<400> SEQUENCE: 40

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser
        115
```

<210> SEQ ID NO 41
<211> LENGTH: 445
<212> TYPE: PRT
<213> ORGANISM: Artificial Sequence
<220> FEATURE:
<223> OTHER INFORMATION: HzVSF_HC_V3

<400> SEQUENCE: 41

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205
```

```
Asn Thr Lys Val Asp Lys Arg Val Glu Ser Lys Tyr Gly Pro Cys
210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
                435                 440                 445

<210> SEQ ID NO 42
<211> LENGTH: 107
<212> TYPE: PRT
<213> ORGANISM: Artificial Sequence
<220> FEATURE:
<223> OTHER INFORMATION: HzVSF_VL_V3

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105

<210> SEQ ID NO 43
<211> LENGTH: 214
```

```
<212> TYPE: PRT
<213> ORGANISM: Artificial Sequence
<220> FEATURE:
<223> OTHER INFORMATION: HzVSF_LC_V3

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 44
<211> LENGTH: 118
<212> TYPE: PRT
<213> ORGANISM: Artificial Sequence
<220> FEATURE:
<223> OTHER INFORMATION: HzVSF_VH_V4

<400> SEQUENCE: 44

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110
```

Leu Val Thr Val Ser Ser
            115

<210> SEQ ID NO 45
<211> LENGTH: 445
<212> TYPE: PRT
<213> ORGANISM: Artificial Sequence
<220> FEATURE:
<223> OTHER INFORMATION: HzVSF_HC_V4

<400> SEQUENCE: 45

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

```
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly Lys
        435                 440                 445

<210> SEQ ID NO 46
<211> LENGTH: 107
<212> TYPE: PRT
<213> ORGANISM: Artificial Sequence
<220> FEATURE:
<223> OTHER INFORMATION: HzVSF_VL_V4

<400> SEQUENCE: 46

Asp Ile Gln Met Thr Gln Ser Pro Ser Ser Leu Ser Ala Ser Val Gly
1               5                   10                  15
Asp Arg Val Thr Ile Thr Cys Arg Ala Ser Glu Asn Ile Tyr Ser Asn
            20                  25                  30
Leu Ala Trp Tyr Gln Gln Lys Pro Gly Lys Ala Pro Lys Leu Leu Ile
        35                  40                  45
Tyr Val Ala Asp Asn Arg Gly Asp Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln His Phe Tyr Gly Thr Pro Arg
                85                  90                  95
Thr Phe Gly Gly Gly Thr Lys Val Glu Ile Lys
            100                 105

<210> SEQ ID NO 47
<211> LENGTH: 214
<212> TYPE: PRT
<213> ORGANISM: Artificial Sequence
<220> FEATURE:
<223> OTHER INFORMATION: HzVSF_LC_V4

<400> SEQUENCE: 47

Asp Ile Gln Met Thr Gln Ser Pro Ser Ser Leu Ser Ala Ser Val Gly
1               5                   10                  15
Asp Arg Val Thr Ile Thr Cys Arg Ala Ser Glu Asn Ile Tyr Ser Asn
            20                  25                  30
Leu Ala Trp Tyr Gln Gln Lys Pro Gly Lys Ala Pro Lys Leu Leu Ile
        35                  40                  45
Tyr Val Ala Asp Asn Arg Gly Asp Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln His Phe Tyr Gly Thr Pro Arg
                85                  90                  95
Thr Phe Gly Gly Gly Thr Lys Val Glu Ile Lys Arg Thr Val Ala Ala
```

```
                100             105             110
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135             140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 48
<211> LENGTH: 118
<212> TYPE: PRT
<213> ORGANISM: Artificial Sequence
<220> FEATURE:
<223> OTHER INFORMATION: HzVSF_VH_V5

<400> SEQUENCE: 48

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser
        115

<210> SEQ ID NO 49
<211> LENGTH: 445
<212> TYPE: PRT
<213> ORGANISM: Artificial Sequence
<220> FEATURE:
<223> OTHER INFORMATION: HzVSF_HC_V5

<400> SEQUENCE: 49

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60
```

-continued

Gln Gly Arg Val Thr Met Thr Val Asp Lys Ser Ile Ser Thr Ala Tyr
 65                  70                  75                  80

Met Glu Leu Ser Arg Leu Arg Ser Asp Asp Thr Ala Val Tyr Tyr Cys
             85                  90                  95

Ala Arg Glu Thr Gly Thr Arg Ala Met Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 50
<211> LENGTH: 107
<212> TYPE: PRT
<213> ORGANISM: Artificial Sequence
<220> FEATURE:
<223> OTHER INFORMATION: HzVSF_VL_V5

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105

<210> SEQ ID NO 51
<211> LENGTH: 214
<212> TYPE: PRT
<213> ORGANISM: Artificial Sequence
<220> FEATURE:
<223> OTHER INFORMATION: HzVSF_LC_V5

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 52
<211> LENGTH: 118

```
<212> TYPE: PRT
<213> ORGANISM: Artificial Sequence
<220> FEATURE:
<223> OTHER INFORMATION: HzVSF_VH_V6

<400> SEQUENCE: 52

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser
            115

<210> SEQ ID NO 53
<211> LENGTH: 445
<212> TYPE: PRT
<213> ORGANISM: Artificial Sequence
<220> FEATURE:
<223> OTHER INFORMATION: HzVSF_HC_V6

<400> SEQUENCE: 53

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Thr Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205
```

```
Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
            385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 54
<211> LENGTH: 107
<212> TYPE: PRT
<213> ORGANISM: Artificial Sequence
<220> FEATURE:
<223> OTHER INFORMATION: HzVSF_VL_V6

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105

<210> SEQ ID NO 55
```

<211> LENGTH: 214
<212> TYPE: PRT
<213> ORGANISM: Artificial Sequence
<220> FEATURE:
<223> OTHER INFORMATION: HzVSF_LC_V6

<400> SEQUENCE: 55

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 56
<211> LENGTH: 118
<212> TYPE: PRT
<213> ORGANISM: Artificial Sequence
<220> FEATURE:
<223> OTHER INFORMATION: HzVSF_VH_V7

<400> SEQUENCE: 56

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
```

```
            100                 105                 110

Leu Val Thr Val Ser Ser
            115

<210> SEQ ID NO 57
<211> LENGTH: 445
<212> TYPE: PRT
<213> ORGANISM: Artificial Sequence
<220> FEATURE:
<223> OTHER INFORMATION: HzVSF_HC_V7

<400> SEQUENCE: 57

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
```

```
                    340                 345                 350
Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 58
<211> LENGTH: 107
<212> TYPE: PRT
<213> ORGANISM: Artificial Sequence
<220> FEATURE:
<223> OTHER INFORMATION: HzVSF_VL_V7

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105

<210> SEQ ID NO 59
<211> LENGTH: 214
<212> TYPE: PRT
<213> ORGANISM: Artificial Sequence
<220> FEATURE:
<223> OTHER INFORMATION: HzVSF_LC_V7

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95
```

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 60
<211> LENGTH: 118
<212> TYPE: PRT
<213> ORGANISM: Artificial Sequence
<220> FEATURE:
<223> OTHER INFORMATION: HzVSF_VH_V8

<400> SEQUENCE: 60

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
            35                  40                  45

Gly Asn Ile Asp Pro Tyr Tyr Gly Ser Asp Thr Tyr Ala Gln Lys Phe
50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Asn Arg Ala Met Asp Tyr Trp Gly Gln Gly Thr
            100                 105                 110

Leu Val Thr Val Ser Ser
            115

<210> SEQ ID NO 61
<211> LENGTH: 445
<212> TYPE: PRT
<213> ORGANISM: Artificial Sequence
<220> FEATURE:
<223> OTHER INFORMATION: HzVSF_HC_V8

<400> SEQUENCE: 61

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
            35                  40                  45

Gly Asn Ile Asp Pro Tyr Tyr Gly Ser Asp Thr Tyr Ala Gln Lys Phe
50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Asn Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 62
<211> LENGTH: 107
<212> TYPE: PRT
<213> ORGANISM: Artificial Sequence
<220> FEATURE:

<223> OTHER INFORMATION: HzVSF_VL_V8

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105

<210> SEQ ID NO 63
<211> LENGTH: 214
<212> TYPE: PRT
<213> ORGANISM: Artificial Sequence
<220> FEATURE:
<223> OTHER INFORMATION: HzVSF_LC_V8

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 64

```
<211> LENGTH: 118
<212> TYPE: PRT
<213> ORGANISM: Artificial Sequence
<220> FEATURE:
<223> OTHER INFORMATION: HzVSF_VH_V9

<400> SEQUENCE: 64

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Asn Met Asn Trp Val Arg Gln Ala Pro Gly Lys Gly Leu Glu Trp Met
            35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
                100                 105                 110

Leu Val Thr Val Ser Ser
            115

<210> SEQ ID NO 65
<211> LENGTH: 445
<212> TYPE: PRT
<213> ORGANISM: Artificial Sequence
<220> FEATURE:
<223> OTHER INFORMATION: HzVSF_HC_V9

<400> SEQUENCE: 65

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Asn Met Asn Trp Val Arg Gln Ala Pro Gly Lys Gly Leu Glu Trp Met
            35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
```

```
                195                 200                 205
Asn Thr Lys Val Asp Lys Arg Val Glu Ser Lys Tyr Gly Pro Pro Cys
210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
            435                 440                 445

<210> SEQ ID NO 66
<211> LENGTH: 107
<212> TYPE: PRT
<213> ORGANISM: Artificial Sequence
<220> FEATURE:
<223> OTHER INFORMATION: HzVSF_VL_V9

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
                100                 105
```

<210> SEQ ID NO 67
<211> LENGTH: 214
<212> TYPE: PRT
<213> ORGANISM: Artificial Sequence
<220> FEATURE:
<223> OTHER INFORMATION: HzVSF_LC_V9

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 68
<211> LENGTH: 118
<212> TYPE: PRT
<213> ORGANISM: Artificial Sequence
<220> FEATURE:
<223> OTHER INFORMATION: HzVSF_VH_V10

<400> SEQUENCE: 68

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95
```

Ala Arg Glu Thr Gly Asn Arg Ala Met Asp Tyr Trp Gly Gln Gly Thr
            100                 105                 110

Leu Val Thr Val Ser Ser
            115

<210> SEQ ID NO 69
<211> LENGTH: 445
<212> TYPE: PRT
<213> ORGANISM: Artificial Sequence
<220> FEATURE:
<223> OTHER INFORMATION: HzVSF_HC_V10

<400> SEQUENCE: 69

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Thr Ala Val Tyr Tyr Cys
                85                  90                  95

Ala Arg Glu Thr Gly Asn Arg Ala Met Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

```
Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 70
<211> LENGTH: 107
<212> TYPE: PRT
<213> ORGANISM: Artificial Sequence
<220> FEATURE:
<223> OTHER INFORMATION: HzVSF_VL_V10

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105

<210> SEQ ID NO 71
<211> LENGTH: 214
<212> TYPE: PRT
<213> ORGANISM: Artificial Sequence
<220> FEATURE:
<223> OTHER INFORMATION: HzVSF_LC_V10

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95
```

-continued

```
Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 72
<211> LENGTH: 118
<212> TYPE: PRT
<213> ORGANISM: Artificial Sequence
<220> FEATURE:
<223> OTHER INFORMATION: HzVSF_VH_V11

<400> SEQUENCE: 72

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser
        115

<210> SEQ ID NO 73
<211> LENGTH: 445
<212> TYPE: PRT
<213> ORGANISM: Artificial Sequence
<220> FEATURE:
<223> OTHER INFORMATION: HzVSF_HC_V11

<400> SEQUENCE: 73

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
```

```
                50                  55                  60
Gln Gly Arg Val Thr Met Thr Val Asp Thr Ser Ala Ser Thr Ala Tyr
 65                  70                  75                  80
Met Glu Leu Ser Arg Leu Arg Ser Asp Thr Ala Val Tyr Tyr Cys
                 85                  90                  95
Ala Arg Glu Thr Gly Thr Arg Ala Met Asp Tyr Trp Gly Gln Gly Thr
                100                 105                 110
Leu Val Thr Val Ser Ser Ala Ser Thr Lys Gly Pro Ser Val Phe Pro
                115                 120                 125
Leu Ala Pro Cys Ser Arg Ser Thr Ser Glu Ser Thr Ala Ala Leu Gly
                130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Lys Thr Tyr Thr Cys Asn Val Asp His Lys Pro Ser
                195                 200                 205
Asn Thr Lys Val Asp Lys Arg Val Glu Ser Lys Tyr Gly Pro Pro Cys
                210                 215                 220
Pro Ser Cys Pro Ala Pro Glu Phe Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Gln Glu Asp Pro Glu Val Gln
                260                 265                 270
Phe Asn Trp Tyr Val Asp Gly Val Glu Val His Asn Ala Lys Thr Lys
                275                 280                 285
Pro Arg Glu Glu Gln Phe Asn Ser Thr Tyr Arg Val Val Ser Val Leu
                290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
                340                 345                 350
Gln Glu Glu Met Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
                370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
                420                 425                 430
His Tyr Thr Gln Lys Ser Leu Ser Leu Ser Leu Gly Lys
                435                 440                 445

<210> SEQ ID NO 74
<211> LENGTH: 107
<212> TYPE: PRT
<213> ORGANISM: Artificial Sequence
```

<220> FEATURE:
<223> OTHER INFORMATION: HzVSF_VL_V11

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Thr Pro Arg
                85                  90                  95

Thr Phe Gly Gly Gly Thr Lys Val Glu Ile Lys
            100                 105

<210> SEQ ID NO 75
<211> LENGTH: 214
<212> TYPE: PRT
<213> ORGANISM: Artificial Sequence
<220> FEATURE:
<223> OTHER INFORMATION: HzVSF_LC_V11

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Thr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 76
<211> LENGTH: 118
<212> TYPE: PRT
<213> ORGANISM: Artificial Sequence
<220> FEATURE:
<223> OTHER INFORMATION: HzVSF_VH_V12

<400> SEQUENCE: 76

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Asn Arg Ala Met Asp Tyr Trp Gly Gln Gly Thr
            100                 105                 110

Leu Val Thr Val Ser Ser
        115
```

<210> SEQ ID NO 77
<211> LENGTH: 445
<212> TYPE: PRT
<213> ORGANISM: Artificial Sequence
<220> FEATURE:
<223> OTHER INFORMATION: HzVSF_HC_V12

<400> SEQUENCE: 77

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Thr Ser Ala Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Asn Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
        210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 78
<211> LENGTH: 107
<212> TYPE: PRT
<213> ORGANISM: Artificial Sequence
<220> FEATURE:
<223> OTHER INFORMATION: HzVSF_VL_V12

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Thr Pro Arg
                85                  90                  95

Thr Phe Gly Gly Gly Thr Lys Val Glu Ile Lys
            100                 105

<210> SEQ ID NO 79
<211> LENGTH: 214
<212> TYPE: PRT
<213> ORGANISM: Artificial Sequence
<220> FEATURE:
<223> OTHER INFORMATION: HzVSF_LC_V12

<400> SEQUENCE: 79

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Arg Gly Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Thr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 80
<211> LENGTH: 118
<212> TYPE: PRT
<213> ORGANISM: Artificial Sequence
<220> FEATURE:
<223> OTHER INFORMATION: HzVSF_VH_V13

<400> SEQUENCE: 80

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

Ala Arg Glu Thr Gly Thr Arg Ala Met Asp Tyr Trp Gly Gln Gly Thr
            100                 105                 110

Leu Val Thr Val Ser Ser
        115

<210> SEQ ID NO 81
<211> LENGTH: 445
<212> TYPE: PRT
<213> ORGANISM: Artificial Sequence
<220> FEATURE:
<223> OTHER INFORMATION: HzVSF_HC_V13

<400> SEQUENCE: 81

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Asn Met Asn Trp Val Arg Gln Ala Pro Gly Lys Gly Leu Glu Trp Met
        35                  40                  45

Gly Asn Ile Asp Pro Tyr Tyr Gly Ser Asp Thr Tyr Ala Gln Lys Phe
    50                  55                  60

Gln Gly Arg Val Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Thr Gly Thr Arg Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 82
<211> LENGTH: 107
<212> TYPE: PRT
<213> ORGANISM: Artificial Sequence
<220> FEATURE:
<223> OTHER INFORMATION: HzVSF_VL_V13

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg
                85                  90                  95

Thr Phe Gly Gly Gly Thr Lys Val Glu Ile Lys
            100                 105

<210> SEQ ID NO 83
<211> LENGTH: 214
<212> TYPE: PRT
<213> ORGANISM: Artificial Sequence
<220> FEATURE:
<223> OTHER INFORMATION: HzVSF_LC_V13

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Val Ala Asp Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Gly Ser Pro Arg

```
                        85                  90                  95
        Thr Phe Gly Gly Gly Thr Lys Val Glu Ile Lys Arg Thr Val Ala Ala
                            100                 105                 110

Pro Ser Val Phe Ile Phe Pro Pro Ser Asp Glu Gln Leu Lys Ser Gly
                    115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
        145                 150                 155                 160

Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
            195                 200                 205

Phe Asn Arg Gly Glu Cys
            210
```

<210> SEQ ID NO 84
<211> LENGTH: 645
<212> TYPE: DNA
<213> ORGANISM: Artificial Sequence
<220> FEATURE:
<223> OTHER INFORMATION: HzVSF hVL.hCkappa

<400> SEQUENCE: 84

```
gacatccaga tgacccagtc tccatcctcc ctgtctgcat ctgtaggaga cagagtcacc    60
atcacttgcc gagcaagtga gaatatttac agtaatttag catggtatca gcagaaacca   120
gggaaagctc ctaagctcct gatctatgtt gcaacaaact agcagatgg ggtcccatca    180
aggttcagcg gcagtggatc tgggacagat tcactctca ccatcagcag cctgcagcct    240
gaagattttg caacttatta ctgtcaacat ttttatggtt ctcctcggac gttcggcgga   300
gggaccaagg tggagatcaa acgcacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag                   645
```

<210> SEQ ID NO 85
<211> LENGTH: 1335
<212> TYPE: DNA
<213> ORGANISM: Artificial Sequence
<220> FEATURE:
<223> OTHER INFORMATION: hVH.hCgamma2

<400> SEQUENCE: 85

```
gaggtgcagc tggtgcagtc tggggctgag gtgaagaagc ctggggcctc agtgaaggtc    60
tcctgcaagg cttctggata caccttcacc ggctacaaca tgaactgggt gcgacaggct   120
cctggaaaag ggcttgagtg gatgggaaat attgatcctt actatggtag tactacctat   180
gcacagaagt tcagggcag ggtcaccatg accgtagaca atccatcag cacagcctac    240
atggagctga gcaggctgag atctgacgac acggccgtgt attactgtgc gagagagact   300
gggacgaggg ctatggacta ctggggtcaa ggaaccctgg tcaccgtctc ctcagcctcc   360
```

```
accaagggcc catcggtctt ccccctggcg ccctgctcca ggagcacctc cgagagcaca    420
gcggccctgg gctgcctggt caaggactac ttccccgaac cggtgacggt gtcgtggaac    480
tcaggcgctc tgaccagcgg cgtgcacacc ttcccggctg tcctacagtc ctcaggactc    540
tactccctca gcagcgtggt gaccgtgccc tccagcaact tcggcaccca gacctacacc    600
tgcaacgtag atcacaagcc cagcaacacc aaggtggaca agacagttga gcgcaaatgt    660
tgtgtcgagt gcccaccgtg cccagcacca cctgtggcag gaccgtcagt cttcctcttc    720
cccccaaaac ccaaggacac cctcatgatc tcccggaccc ctgaggtcac gtgcgtggtg    780
gtggacgtga gccacgaaga ccccgaggtc cagttcaact ggtacgtgga cggcgtggag    840
gtgcataatg ccaagacaaa gccacgggag gagcagttca acagcacgtt ccgtgtggtc    900
agcgtcctca ccgtcgtgca ccaggactgg ctgaacggca aggagtacaa gtgcaaggtc    960
tccaacaaag gcctcccagc ccccatcgag aaaaccatct ccaaaccaa agggcagccc    1020 cgagaaccac aggtgtacac cctgccccca tcccgggagg agatgaccaa gaaccaggtc   1080
agcctgacct gcctggtcaa aggcttctac cccagcgaca tcgccgtgga gtgggagagc   1140
aatgggcagc cggagaacaa ctacaacacc acacctccca tgctggactc cgacggctcc   1200
ttcttcctct acagcaagct caccgtggac aagagcaggt ggcagcaggg gaacgtcttc   1260
tcatgctccg tgatgcatga ggctctgcac aaccactaca cgcagaagag cctctccctg   1320
tctccgggta aatga                                                    1335

<210> SEQ ID NO 86
<211> LENGTH: 1338
<212> TYPE: DNA
<213> ORGANISM: Artificial Sequence
<220> FEATURE:
<223> OTHER INFORMATION: hVH.hCgamma4

<400> SEQUENCE: 86
gaggtgcagc tggtgcagtc tggggctgag gtgaagaagc ctggggcctc agtgaaggtc     60
tcctgcaagg cttctggata caccttcacc ggctacaaca tgaactgggt gcgacaggct    120
cctggaaaag gcttgagtg gatgggaaat attgatcctt actatggtag tactacctat    180
gcacagaagt ttcagggcag ggtcaccatg accgtagaca atccatcag cacagcctac    240 atggagctga gcaggctgag atctgacgac acggccgtgt attactgtgc gagagagact    300
gggacgaggg ctatggacta ctggggtcaa ggaaccctgg tcaccgtctc ctcagcttcc    360
accaagggcc catccgtctt ccccctggcg ccctgctcca ggagcacctc cgagagcaca    420
gccgccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcacgaa gacctacacc    600 tgcaacgtag atcacaagcc cagcaacacc aaggtggaca agagagttga gtccaaatat    660
ggtcccccat gcccatcatg cccagcacct gagttcctgg ggggaccatc agtcttcctg    720
ttccccccaa acccaaggac actctcatg atctcccgga cccctgaggt cacgtgcgtg    780
gtggtggacg tgagccagga agaccccgag gtccagttca ctggtacgt ggatggcgtg    840 gaggtgcata tgccaagac aaagccgcgg gaggagcagt tcaacagcac gtaccgtgtg    900
gtcagcgtcc tcaccgtcct gcaccaggac tggctgaacg gcaaggagta caagtgcaag    960
gtctccaaca aaggcctccc gtcctccatc gagaaaacca tctccaaagc caagggcag   1020
```

```
cccgagagc acaggtgta cacctgccc ccatcccagg aggagatgac caagaaccag    1080
gtcagcctga cctgcctggt caaaggcttc taccccagcg acatcgccgt ggagtgggag    1140
agcaatgggc agccggagaa caactacaag accacgcctc ccgtgctgga ctccgacggc    1200
tccttcttcc tctacagcag gctaaccgtg gacaagagca ggtggcagga ggggaatgtc    1260
ttctcatgct ccgtgatgca tgaggctctg cacaaccact acacacagaa gagcctctcc    1320
ctgtctctgg gtaaatga                                                  1338

<210> SEQ ID NO 87
<211> LENGTH: 1338
<212> TYPE: DNA
<213> ORGANISM: Artificial Sequence
<220> FEATURE:
<223> OTHER INFORMATION: HzVSF a1 gamma4

<400> SEQUENCE: 87
gagatccagc tggtgcagtc tggggctgag gtgaagaagc ctggggcctc agtgaaggtc     60
tcctgcaagg cttctggata caccttcacc ggctacaaca tgaactgggt gcgacaggct    120
cctggaaaag ggcttgagtg gatgggaaat attgatcctt actatggtag tactacctat    180
gcacagaagt ttcagggcag ggtcaccatg accgtagaca atccatcag cacagcctac     240 atggagctga gcaggctgag atctgacgac acggccgtgt attactgtgc gagagagact    300
gggacgaggg ctatgactac tgggggtcaa ggaaccctgg tcaccgtctc ctcagcctcc    360
accaagggcc catccgtctt ccccctggcg ccctgctcca ggagcacctc cgagagcaca    420
gccgccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcacgaa gacctacacc    600 tgcaacgtag atcacaagcc cagcaacacc aaggtggaca agagagttga gtccaaatat    660 ggtccccat gcccatcatg cccagcacct gagttcctgg ggggaccatc agtcttcctg    720
ttccccccaa aacccaagga cactctcatg atctcccgga cccctgaggt cacgtgcgtg    780
gtggtggacg tgagccagga agaccccgag gtccagttca actggtacgt ggatggcgtg    840
gaggtgcata atgccaagac aaagccgcgg gaggagcagt tcaacagcac gtaccgtgtg    900
gtcagcgtcc tcaccgtcct gcaccaggac tggctgaacg gcaaggagta caagtgcaag    960
gtctccaaca aaggcctccc gtcctccatc gagaaaacca tctccaaagc caaagggcag    1020 cccgagagc acaggtgta cacctgccc ccatcccagg aggagatgac caagaaccag    1080
gtcagcctga cctgcctggt caaaggcttc taccccagcg acatcgccgt ggagtgggag    1140
agcaatgggc agccggagaa caactacaag accacgcctc ccgtgctgga ctccgacggc    1200
tccttcttcc tctacagcag gctaaccgtg gacaagagca ggtggcagga ggggaatgtc    1260
ttctcatgct ccgtgatgca tgaggctctg cacaaccact acacacagaa gagcctctcc    1320
ctgtctctgg gtaaatga                                                  1338

<210> SEQ ID NO 88
<211> LENGTH: 1338
<212> TYPE: DNA
<213> ORGANISM: Artificial Sequence
<220> FEATURE:
<223> OTHER INFORMATION: HzVSF a2 gamma4

<400> SEQUENCE: 88
gaggtgcagc tggtgcagtc tggggctgag gtgaagaagc ctggggcctc agtgaaggtc     60
```

```
tcctgcaagg cttctggata caccttcacc ggctacaaca tgaactgggt gcgacaggct      120
cctggaaaag ggcttgagtg gattggaaat attgatcctt actatggtag tactacctat      180
gcacagaagt ttcagggcag ggtcaccatg accgtagaca atccatcag cacagcctac       240 atggagctga gcaggctgag atctgacgac acggccgtgt attactgtgc gagagagact      300
gggacgaggg ctatggacta ctggggtcaa ggaaccctgg tcaccgtctc ctcagcctcc      360
accaagggcc catccgtctt ccccctggcg ccctgctcca ggagcacctc cgagagcaca      420
gccgccctgg gctgcctggt caaggactac ttccccgaac cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct gggcacgaa gacctacacc       600 tgcaacgtag atcacaagcc cagcaacacc aaggtggaca gagagttga gtccaaatat       660 ggtcccccat gcccatcatg cccagcacct gagttcctgg ggggaccatc agtcttcctg      720
ttccccccaa aacccaagga cactctcatg atctcccgga cccctgaggt cacgtgcgtg      780
gtggtggacg tgagccagga agaccccgag gtccagttca actggtacgt ggatggcgtg      840
gaggtgcata atgccaagac aaagccgcgg gaggagcagt tcaacagcac gtaccgtgtg      900
gtcagcgtcc tcaccgtcct gcaccaggac tggctgaacg gcaaggagta caagtgcaag      960
gtctccaaca aaggcctccc gtcctccatc gagaaaacca tctccaaagc caaagggcag      1020
ccccgagagc cacaggtgta caccctgccc ccatcccagg aggagatgac caagaaccag      1080
gtcagcctga cctgcctggt caaaggcttc taccccagcg acatcgccgt ggagtgggag      1140
agcaatgggc agccggagaa caactacaag accacgcctc ccgtgctgga ctccgacggc      1200
tccttcttcc tctacagcag gctaaccgtg gacaagagca ggtggcagga ggggaatgtc      1260
ttctcatgct ccgtgatgca tgaggctctg cacaaccact acacacagaa gagcctctcc      1320
ctgtctctgg gtaaatga                                                    1338

<210> SEQ ID NO 89
<211> LENGTH: 1338
<212> TYPE: DNA
<213> ORGANISM: Artificial Sequence
<220> FEATURE:
<223> OTHER INFORMATION: HzVSF a3 gamma4

<400> SEQUENCE: 89
gagatccagc tggtgcagtc tggggctgag gtgaagaagc ctggggcctc agtgaaggtc       60
tcctgcaagg cttctggata caccttcacc ggctacaaca tgaactgggt gcgacaggct      120
cctggaaaag ggcttgagtg gattggaaat attgatcctt actatggtag tactacctat      180
gcacagaagt ttcagggcag ggtcaccatg accgtagaca atccatcag cacagcctac       240 atggagctga gcaggctgag atctgacgac acggccgtgt attactgtgc gagagagact      300
gggacgaggg ctatggacta ctggggtcaa ggaaccctgg tcaccgtctc ctcagcctcc      360
accaagggcc catccgtctt ccccctggcg ccctgctcca ggagcacctc cgagagcaca      420
gccgccctgg gctgcctggt caaggactac ttccccgaac cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct gggcacgaa gacctacacc       600 tgcaacgtag atcacaagcc cagcaacacc aaggtggaca gagagttga gtccaaatat       660 ggtcccccat gcccatcatg cccagcacct gagttcctgg ggggaccatc agtcttcctg      720
```

| | |
|---|---|
| ttccccccaa acccaagga cactctcatg atctcccgga ccectgaggt cacgtgcgtg | 780 |
| gtggtggacg tgagccagga agaccccgag gtccagttca actggtacgt ggatggcgtg | 840 |
| gaggtgcata atgccaagac aaagccgcgg gaggagcagt tcaacagcac gtaccgtgtg | 900 |
| gtcagcgtcc tcaccgtcct gcaccaggac tggctgaacg gcaaggagta caagtgcaag | 960 |
| gtctccaaca aaggcctccc gtcctccatc gagaaaacca tctccaaagc caaagggcag | 1020 |
| ccccgagagc cacaggtgta caccctgccc ccatcccagg aggagatgac caagaaccag | 1080 |
| gtcagcctga cctgcctggt caaaggcttc taccccagcg acatcgccgt ggagtgggag | 1140 |
| agcaatgggc agccggagaa caactacaag accacgcctc ccgtgctgga ctccgacggc | 1200 |
| tccttcttcc tctacagcag gctaaccgtg gacaagagca ggtggcagga ggggaatgtc | 1260 |
| ttctcatgct ccgtgatgca tgaggctctg cacaaccact acacacagaa gagcctctcc | 1320 |
| ctgtctctgg gtaaatga | 1338 |

<210> SEQ ID NO 90
<211> LENGTH: 645
<212> TYPE: DNA
<213> ORGANISM: Artificial Sequence
<220> FEATURE:
<223> OTHER INFORMATION: LC1

<400> SEQUENCE: 90

| | |
|---|---|
| gacatccaga tgacccagtc tccatcctcc ctgtctgcat ctgtaggaga cagagtcacc | 60 |
| atcacttgcc gagcaagtga gaatatttac agtaatttag catggtatca gcagaaacca | 120 |
| gggaaagctc ctaagctcct gatctatgtt gcagacaact agcagatgg ggtcccatca | 180 |
| aggttcagcg gcagtggatc tgggacagat ttcactctca ccatcagcag cctgcagcct | 240 |
| gaagattttg caacttatta ctgtcaacat ttttatggtt ctcctcggac gttcggcgga | 300 |
| gggaccaagg tggagatcaa acgtacggtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gttag | 645 |

<210> SEQ ID NO 91
<211> LENGTH: 645
<212> TYPE: DNA
<213> ORGANISM: Artificial Sequence
<220> FEATURE:
<223> OTHER INFORMATION: LC4

<400> SEQUENCE: 91

| | |
|---|---|
| gacatccaga tgacccagtc tccatcctcc ctgtctgcat ctgtaggaga cagagtcacc | 60 |
| atcacttgcc gagcaagtga gaatatttac agtaatttag catggtatca gcagaaacca | 120 |
| gggaaagctc ctaagctcct gatctatgtt gcagacaacc gcggagatgg ggtcccatca | 180 |
| aggttcagcg gcagtggatc tgggacagat ttcactctca ccatcagcag cctgcagcct | 240 |
| gaagattttg caacttatta ctgtcaacat ttttatggta cccctcggac gttcggcgga | 300 |
| gggaccaagg tggagatcaa acgtacggtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |

```
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645
```

<210> SEQ ID NO 92
<211> LENGTH: 354
<212> TYPE: DNA
<213> ORGANISM: Artificial Sequence
<220> FEATURE:
<223> OTHER INFORMATION: VH1

<400> SEQUENCE: 92

```
gaggtgcagc tggtgcagtc tggggctgag gtgaagaagc ctggggcctc agtgaaggtc    60
tcctgcaagg cttctggata caccttcacc ggctacaaca tgaactgggt gcgacaggct    120
cctggaaaag ggcttgagtg gatgggaaat attgatcctt actatggtag tgatacctat    180
gcacagaagt tcagggcag ggtcaccatg accgtagaca aatccatcag cacagcctac    240
atggagctga gcaggctgag atctgacgac acggccgtgt attactgtgc gagagagact    300
gggacgaggg ctatggacta ctggggtcaa ggaaccctgg tcaccgtctc ctca          354
```

<210> SEQ ID NO 93
<211> LENGTH: 354
<212> TYPE: DNA
<213> ORGANISM: Artificial Sequence
<220> FEATURE:
<223> OTHER INFORMATION: VH4

<400> SEQUENCE: 93

```
gaggtgcagc tggtgcagtc tggggctgag gtgaagaagc ctggggcctc agtgaaggtc    60
tcctgcaagg cttctggata caccttcacc ggctacaaca tgaactgggt gcgacaggct    120
cctggaaaag ggcttgagtg gatgggaaat attgatcctt actatggtag tgatacctat    180
gcacagaagt tcagggcag ggtcaccatg accgtagaca cttccgcaag cacagcctac    240
atggagctga gcaggctgag atctgacgac acggccgtgt attactgtgc gagagagact    300
gggaataggg ctatggacta ctggggtcaa ggaaccctgg tcaccgtctc ctca          354
```

<210> SEQ ID NO 94
<211> LENGTH: 1338
<212> TYPE: DNA
<213> ORGANISM: Artificial Sequence
<220> FEATURE:
<223> OTHER INFORMATION: HzVSF_V1_HC

<400> SEQUENCE: 94

```
gaggtgcagc tggtgcagtc tggggctgag gtgaagaagc ctggggcctc agtgaaggtc    60
tcctgcaagg cttctggata caccttcacc ggctacaaca tgaactgggt gcgacaggct    120
cctggaaaag ggcttgagtg gatgggaaat attgatcctt actatggtag tactacctat    180
gcacagaagt tcagggcag ggtcaccatg accgtagaca aatccatcag cacagcctac    240
atggagctga gcaggctgag atctgacgac acggccgtgt attactgtgc gagagagact    300
gggacgaggg ctatggacta ctggggtcaa ggaaccctgg tcaccgtctc ctcagcttcc    360
accaagggcc catccgtctt ccccctggcg ccctgctcca ggagcacctc cgagagcaca    420
gccgccctgg gctgcctggt caaggactac ttccccgaac cggtgacggt gtcgtggaac    480
tcaggcgccc tgaccagcgg cgtgcacacc ttcccggctg tcctacagtc ctcaggactc    540
```

| | |
|---|---|
| tactccctca gcagcgtggt gaccgtgccc tccagcagct tgggcacgaa gacctacacc | 600 |
| tgcaacgtag atcacaagcc cagcaacacc aaggtggaca agagagttga gtccaaatat | 660 |
| ggtcccccat gcccatcatg cccagcacct gagttcctgg ggggaccatc agtcttcctg | 720 |
| ttccccccaa aacccaagga cactctcatg atctcccgga cccctgaggt cacgtgcgtg | 780 |
| gtggtggacg tgagccagga agaccccgag gtccagttca actggtacgt ggatggcgtg | 840 |
| gaggtgcata atgccaagac aaagccgcgg gaggagcagt tcaacagcac gtaccgtgtg | 900 |
| gtcagcgtcc tcaccgtcct gcaccaggac tggctgaacg gcaaggagta caagtgcaag | 960 |
| gtctccaaca aaggcctccc gtcctccatc gagaaaacca tctccaaagc caaagggcag | 1020 |
| ccccgagagc cacaggtgta caccctgccc ccatcccagg aggagatgac caagaaccag | 1080 |
| gtcagcctga cctgcctggt caaaggcttc taccccagcg acatcgccgt ggagtgggag | 1140 |
| agcaatgggc agccggagaa caactacaag accacgcctc ccgtgctgga ctccgacggc | 1200 |
| tccttcttcc tctacagcag gctaaccgtg gacaagagca ggtggcagga ggggaatgtc | 1260 |
| ttctcatgct ccgtgatgca tgaggctctg cacaaccact acacacagaa gagcctctcc | 1320 |
| ctgtctctgg gtaaatga | 1338 |

<210> SEQ ID NO 95
<211> LENGTH: 645
<212> TYPE: DNA
<213> ORGANISM: Artificial Sequence
<220> FEATURE:
<223> OTHER INFORMATION: HzVSF_V1_LC

<400> SEQUENCE: 95

| | |
|---|---|
| gacatccaga tgacccagtc tccatcctcc ctgtctgcat ctgtaggaga cagagtcacc | 60 |
| atcacttgcc gagcaagtga gaatatttac agtaatttag catggtatca gcagaaacca | 120 |
| gggaaagctc ctaagctcct gatctatgtt gcagacaact tagcagatgg ggtcccatca | 180 |
| aggttcagcg gcagtggatc tgggacagat ttcactctca ccatcagcag cctgcagcct | 240 |
| gaagattttg caacttatta ctgtcaacat ttttatggtt ctcctcggac gttcggcgga | 300 |
| gggaccaagg tggagatcaa acgtacggtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gttag | 645 |

<210> SEQ ID NO 96
<211> LENGTH: 1338
<212> TYPE: DNA
<213> ORGANISM: Artificial Sequence
<220> FEATURE:
<223> OTHER INFORMATION: HzVSF_V2_HC

<400> SEQUENCE: 96

| | |
|---|---|
| gaggtgcagc tggtgcagtc tggggctgag gtgaagaagc tggggcctc agtgaaggtc | 60 |
| tcctgcaagg cttctggata caccttcacc ggctacaaca tgaactgggt gcgacaggct | 120 |
| cctggaaaag gcttgagtg gatgggaaat attgatcctt actatggtag tactacctat | 180 |
| gcacagaagt tcagggcag ggtcaccatg accgtagaca aatccatcag cacagcctac | 240 |
| atggagctga gcaggctgag atctgacgac acggccgtgt attactgtgc gagagagact | 300 |

```
gggacgaggg  ctatggacta  ctggggtcaa  ggaaccctgg  tcaccgtctc  ctcagcttcc    360
accaagggcc  catccgtctt  cccctggcg   ccctgctcca  ggagcacctc  cgagagcaca    420
gccgccctgg  gctgcctggt  caaggactac  ttccccgaac  cggtgacggt  gtcgtggaac    480
tcaggcgccc  tgaccagcgg  cgtgcacacc  ttccggctg   tcctacagtc  tcaggactc     540 tactccctca  gcagcgtggt  gaccgtgccc  tccagcagct  gggcacgaa   gacctacacc    600 tgcaacgtag  atcacaagcc  cagcaacacc  aaggtggaca  agagagttga  gtccaaatat    660 ggtccccat   gcccatcatg  cccagcacct  gagttcctgg  ggggaccatc  agtcttcctg    720 ttcccccaa   aacccaagga  cactctcatg  atctcccgga  cccctgaggt  cacgtgcgtg    780
gtggtggacg  tgagccagga  agaccccgag  gtccagttca  actggtacgt  ggatggcgtg    840
gaggtgcata  atgccaagac  aaagccgcgg  gaggagcagt  tcaacagcac  gtaccgtgtg    900
gtcagcgtcc  tcaccgtcct  gcaccaggac  tggctgaacg  gcaaggagta  caagtgcaag    960
gtctccaaca  aaggcctccc  gtcctccatc  gagaaaacca  tctccaaagc  caaagggcag   1020
ccccgagagc  cacaggtgta  caccctgccc  ccatcccagg  aggagatgac  caagaaccag   1080
gtcagcctga  cctgcctggt  caaaggcttc  taccccagcg  acatcgccgt  ggagtgggag   1140
agcaatgggc  agccggagaa  caactacaag  accacgcctc  ccgtgctgga  ctccgacggc   1200
tccttcttcc  tctacagcag  gctaaccgtg  gacaagagca  ggtggcagga  ggggaatgtc   1260
ttctcatgct  ccgtgatgca  tgaggctctg  cacaaccact  acacacagaa  gagcctctcc   1320
ctgtctctgg  gtaaatga                                                    1338
```

<210> SEQ ID NO 97
<211> LENGTH: 645
<212> TYPE: DNA
<213> ORGANISM: Artificial Sequence
<220> FEATURE:
<223> OTHER INFORMATION: HzVSF_V2_LC

<400> SEQUENCE: 97

```
gacatccaga  tgacccagtc  tccatcctcc  ctgtctgcat  ctgtaggaga  cagagtcacc    60
atcacttgcc  gagcaagtga  gaatatttac  agtaatttag  catggtatca  gcagaaacca   120
gggaaagctc  ctaagctcct  gatctatgtt  gcagacaact  taggagatgg  ggtcccatca   180
aggttcagcg  gcagtggatc  tgggacagat  ttcactctca  ccatcagcag  cctgcagcct   240
gaagattttg  caacttatta  ctgtcaacat  ttttatggtt  ctcctcggac  gttcggcgga   300
gggaccaagg  tggagatcaa  acgtacggtg  gctgcaccat  ctgtcttcat  cttcccgcca   360
tctgatgagc  agttgaaatc  tggaactgcc  tctgttgtgt  gcctgctgaa  taacttctat   420
cccagagagg  ccaaagtaca  gtggaaggtg  gataacgccc  tccaatcggg  taactcccag   480
gagagtgtca  cagagcagga  cagcaaggac  agcacctaca  gcctcagcag  caccctgacg   540
ctgagcaaag  cagactacga  gaaacacaaa  gtctacgcct  cgaagtcac   ccatcagggc   600 ctgagctcgc  ccgtcacaaa  gagcttcaac  aggggagagt  gttag                    645
```

<210> SEQ ID NO 98
<211> LENGTH: 1338
<212> TYPE: DNA
<213> ORGANISM: Artificial Sequence
<220> FEATURE:
<223> OTHER INFORMATION: HzVSF_V3_HC

<400> SEQUENCE: 98

| | |
|---|---:|
| gaggtgcagc tggtgcagtc tggggctgag gtgaagaagc ctggggcctc agtgaaggtc | 60 |
| tcctgcaagg cttctggata caccttcacc ggctacaaca tgaactgggt gcgacaggct | 120 |
| cctggaaaag ggcttgagtg gatgggaaat attgatcctt actatggtag tactacctat | 180 |
| gcacagaagt tcagggcag gtcaccatg accgtagaca atccatcag cacagcctac | 240 |
| atggagctga gcaggctgag atctgacgac acggccgtgt attactgtgc gagagagact | 300 |
| gggacgaggg ctatggacta ctggggtcaa ggaaccctgg tcaccgtctc ctcagcttcc | 360 |
| accaagggcc catccgtctt ccccctggcg ccctgctcca ggagcacctc cgagagcaca | 420 |
| gccgccctgg gctgcctggt caaggactac ttccccgaac cggtgacggt gtcgtggaac | 480 |
| tcaggcgccc tgaccagcgg cgtgcacacc ttcccggctg tcctacagtc ctcaggactc | 540 |
| tactccctca gcagcgtggt gaccgtgccc tccagcagct gggcacgaa gacctacacc | 600 |
| tgcaacgtag atcacaagcc cagcaacacc aaggtggaca gagagttga gtccaaatat | 660 |
| ggtcccccat gcccatcatg cccagcacct gagttcctgg ggggaccatc agtcttcctg | 720 |
| ttccccccaa aacccaagga cactctcatg atctcccgga cccctgaggt cacgtgcgtg | 780 |
| gtggtggacg tgagccagga agaccccgag gtccagttca actggtacgt ggatggcgtg | 840 |
| gaggtgcata atgccaagac aaagccgcgg gaggagcagt tcaacagcac gtaccgtgtg | 900 |
| gtcagcgtcc tcaccgtcct gcaccaggac tggctgaacg gcaaggagta caagtgcaag | 960 |
| gtctccaaca aaggcctccc gtcctccatc gagaaaacca tctccaaagc caagggcag | 1020 |
| ccccgagagc cacaggtgta caccctgccc ccatcccagg aggagatgac caagaaccag | 1080 |
| gtcagcctga cctgcctggt caaaggcttc taccccagcg acatcgccgt ggagtgggag | 1140 |
| agcaatgggc agccggagaa caactacaag accacgcctc ccgtgctgga ctccgacggc | 1200 |
| tccttcttcc tctacagcag gctaaccgtg gacaagagca ggtggcagga ggggaatgtc | 1260 |
| ttctcatgct ccgtgatgca tgaggctctg cacaaccact acacacagaa gagcctctcc | 1320 |
| ctgtctctgg gtaaatga | 1338 |

<210> SEQ ID NO 99
<211> LENGTH: 645
<212> TYPE: DNA
<213> ORGANISM: Artificial Sequence
<220> FEATURE:
<223> OTHER INFORMATION: HzVSF_V3_LC

<400> SEQUENCE: 99

| | |
|---|---:|
| gacatccaga tgacccagtc tccatcctcc ctgtctgcat ctgtaggaga cagagtcacc | 60 |
| atcacttgcc gagcaagtga gaatatttac agtaatttag catggtatca gcagaaacca | 120 |
| gggaaagctc ctaagctcct gatctatgtt gcagacaacc gcggagatgg ggtcccatca | 180 |
| aggttcagcg gcagtggatc tgggacagat ttcactctca ccatcagcag cctgcagcct | 240 |
| gaagattttg caacttatta ctgtcaacat ttttatggtt ctcctcggac gttcggcgga | 300 |
| gggaccaagg tggagatcaa acgtacggtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gttag | 645 |

<210> SEQ ID NO 100
<211> LENGTH: 1338
<212> TYPE: DNA
<213> ORGANISM: Artificial Sequence
<220> FEATURE:
<223> OTHER INFORMATION: HzVSF_V4_HC

<400> SEQUENCE: 100

| | | | | | |
|---|---|---|---|---|---|
| gaggtgcagc | tggtgcagtc | tggggctgag | gtgaagaagc | ctggggcctc | agtgaaggtc | 60 |
| tcctgcaagg | cttctggata | caccttcacc | ggctacaaca | tgaactgggt | gcgacaggct | 120 |
| cctggaaaag | ggcttgagtg | gatgggaaat | attgatcctt | actatggtag | tactacctat | 180 |
| gcacagaagt | tcagggcag | ggtcaccatg | accgtagaca | aatccatcag | cacagcctac | 240 |
| atggagctga | gcaggctgag | atctgacgac | acggccgtgt | attactgtgc | gagagagact | 300 |
| gggacgaggg | ctatggacta | ctggggtcaa | ggaaccctgg | tcaccgtctc | ctcagcttcc | 360 |
| accaagggcc | catccgtctt | ccccctggcg | ccctgctcca | ggagcacctc | cgagagcaca | 420 |
| gccgccctgg | gctgcctggt | caaggactac | ttccccgaac | cggtgacggt | gtcgtggaac | 480 |
| tcaggcgccc | tgaccagcgg | cgtgcacacc | ttcccggctg | tcctacagtc | ctcaggactc | 540 |
| tactccctca | gcagcgtggt | gaccgtgccc | tccagcagct | tgggcacgaa | gacctacacc | 600 |
| tgcaacgtag | atcacaagcc | cagcaacacc | aaggtggaca | agagagttga | gtccaaatat | 660 |
| ggtcccccat | gcccatcatg | cccagcacct | gagttcctgg | ggggaccatc | agtcttcctg | 720 |
| ttccccccaa | aacccaagga | cactctcatg | atctcccgga | cccctgaggt | cacgtgcgtg | 780 |
| gtggtggacg | tgagccagga | agaccccgag | gtccagttca | actggtacgt | ggatggcgtg | 840 |
| gaggtgcata | atgccaagac | aaagccgcgg | gaggagcagt | tcaacagcac | gtaccgtgtg | 900 |
| gtcagcgtcc | tcaccgtcct | gcaccaggac | tggctgaacg | gcaaggagta | caagtgcaag | 960 |
| gtctccaaca | aaggcctccc | gtcctccatc | gagaaaacca | tctccaaagc | caaagggcag | 1020 |
| ccccgagagc | cacaggtgta | caccctgccc | ccatcccagg | aggagatgac | caagaaccag | 1080 |
| gtcagcctga | cctgcctggt | caaaggcttc | taccccagcg | acatcgccgt | ggagtgggag | 1140 |
| agcaatgggc | agccggagaa | caactacaag | accacgcctc | ccgtgctgga | ctccgacggc | 1200 |
| tccttcttcc | tctacagcag | gctaaccgtg | gacaagagca | ggtggcagga | ggggaatgtc | 1260 |
| ttctcatgct | ccgtgatgca | tgaggctctg | cacaaccact | acacacagaa | gagcctctcc | 1320 |
| ctgtctctgg | gtaaatga | | | | | 1338 |

<210> SEQ ID NO 101
<211> LENGTH: 645
<212> TYPE: DNA
<213> ORGANISM: Artificial Sequence
<220> FEATURE:
<223> OTHER INFORMATION: HzVSF_V4_LC

<400> SEQUENCE: 101

| | | | | | |
|---|---|---|---|---|---|
| gacatccaga | tgacccagtc | tccatcctcc | ctgtctgcat | ctgtaggaga | cagagtcacc | 60 |
| atcacttgcc | gagcaagtga | gaatatttac | agtaatttag | catggtatca | gcagaaacca | 120 |
| gggaaagctc | ctaagctcct | gatctatgtt | gcagacaacc | gcggagatgg | ggtcccatca | 180 |
| aggttcagcg | gcagtggatc | tgggacagat | ttcactctca | ccatcagcag | cctgcagcct | 240 |
| gaagattttg | caacttatta | ctgtcaacat | ttttatggta | ccctcggac | gttcggcgga | 300 |
| gggaccaagg | tggagatcaa | acgtacggtg | gctgcaccat | ctgtcttcat | cttcccgcca | 360 |
| tctgatgagc | agttgaaatc | tggaactgcc | tctgttgtgt | gcctgctgaa | taacttctat | 420 |

| | |
|---|---|
| cccagagagg ccaaagtaca gtggaaggtg ataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gttag | 645 |

<210> SEQ ID NO 102
<211> LENGTH: 1338
<212> TYPE: DNA
<213> ORGANISM: Artificial Sequence
<220> FEATURE:
<223> OTHER INFORMATION: HzVSF_V5_HC

<400> SEQUENCE: 102

| | |
|---|---|
| gaggtgcagc tggtgcagtc tggggctgag gtgaagaagc tggggcctc agtgaaggtc | 60 |
| tcctgcaagg cttctggata ccttcacc ggctacaaca tgaactgggt gcgacaggct | 120 |
| cctggaaaag gcttgagtg gatgggaaat attgatcctt actatggtag tgatacctat | 180 |
| gcacagaagt ttcagggcag ggtcaccatg accgtagaca aatccatcag cacagcctac | 240 |
| atggagctga gcaggctgag atctgacgac acggccgtgt attactgtgc gagagagact | 300 |
| gggacgaggg ctatggacta ctggggtcaa ggaaccctgg tcaccgtctc ctcagcttcc | 360 |
| accaagggcc catccgtctt ccccctggcg ccctgctcca ggagcacctc cgagagcaca | 420 |
| gccgccctgg gctgcctggt caaggactac ttccccgaac cggtgacggt gtcgtggaac | 480 |
| tcaggcgccc tgaccagcgg cgtgcacacc ttcccggctg tcctacagtc ctcaggactc | 540 |
| tactccctca gcagcgtggt gaccgtgccc tccagcagct gggcacgaa gacctacacc | 600 |
| tgcaacgtag atcacaagcc cagcaacacc aaggtggaca gagagttga gtccaaatat | 660 |
| ggtccccat gcccatcatg cccagcacct gagttcctgg ggggaccatc agtcttcctg | 720 |
| ttccccccaa aacccaagga cactctcatg atctcccgga cccctgaggt cacgtgcgtg | 780 |
| gtggtggacg tgagccagga agaccccgag gtccagttca actggtacgt ggatggcgtg | 840 |
| gaggtgcata atgccaagac aaagccgcgg gaggagcagt tcaacagcac gtaccgtgtg | 900 |
| gtcagcgtcc tcaccgtcct gcaccaggac tggctgaacg gcaaggagta caagtgcaag | 960 |
| gtctccaaca aaggcctccc gtcctccatc gagaaaacca tctccaaagc caaagggcag | 1020 |
| ccccgagagc cacaggtgta caccctgccc ccatcccagg aggagatgac caagaaccag | 1080 |
| gtcagcctga cctgcctggt caaaggcttc taccccagcg acatcgccgt ggagtgggag | 1140 |
| agcaatgggc agccggagaa caactacaag accacgcctc ccgtgctgga ctccgacggc | 1200 |
| tccttcttcc tctacagcag gctaaccgtg gacaagagca ggtggcagga ggggaatgtc | 1260 |
| ttctcatgct ccgtgatgca tgaggctctg cacaaccact acacacagaa gagcctctcc | 1320 |
| ctgtctctgg gtaaatga | 1338 |

<210> SEQ ID NO 103
<211> LENGTH: 645
<212> TYPE: DNA
<213> ORGANISM: Artificial Sequence
<220> FEATURE:
<223> OTHER INFORMATION: HzVSF_V5_LC

<400> SEQUENCE: 103

| | |
|---|---|
| gacatccaga tgacccagtc tccatcctcc ctgtctgcat ctgtaggaga cagagtcacc | 60 |
| atcacttgcc gagcaagtga gaatatttac agtaatttag catggtatca gcagaaacca | 120 |
| gggaaagctc ctaagctcct gatctatgtt gcaacaaact tagcagatgg ggtcccatca | 180 |

```
aggttcagcg gcagtggatc tgggacagat tcactctca ccatcagcag cctgcagcct      240
gaagattttg caacttatta ctgtcaacat ttttatggtt ctcctcggac gttcggcgga      300
gggaccaagg tggagatcaa acgtacggtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gttag                      645
```

```
<210> SEQ ID NO 104
<211> LENGTH: 1338
<212> TYPE: DNA
<213> ORGANISM: Artificial Sequence
<220> FEATURE:
<223> OTHER INFORMATION: HzVSF_V6_HC

<400> SEQUENCE: 104
gaggtgcagc tggtgcagtc tggggctgag gtgaagaagc tggggcctc agtgaaggtc       60 tcctgcaagg cttctggata caccttcacc ggctacaaca tgaactgggt gcgacaggct      120
cctggaaaag ggcttgagtg gatgggaaat attgatcctt actatggtag tactacctat      180
gcacagaagt ttcagggcag ggtcaccatg accgtagaca cttccgcaag cacagcctac      240
atggagctga gcaggctgag atctgacgac acggccgtgt attactgtgc gagagagact      300
gggacgaggg ctatggacta ctggggtcaa ggaaccctgg tcaccgtctc ctcagcttcc      360
accaagggcc catccgtctt ccccctggcg ccctgctcca ggagcacctc cgagagcaca      420
gccgccctgg gctgcctggt caaggactac ttccccgaac cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct gggcacgaa gacctacacc      600 tgcaacgtag atcacaagcc cagcaacacc aaggtggaca gagagttgag tccaaatat      660 ggtcccccat gcccatcatg cccagcacct gagttcctgg ggggaccatc agtcttcctg      720
ttccccccaa aacccaagga cactctcatg atctcccgga cccctgaggt cacgtgcgtg      780
gtggtggacg tgagccagga agaccccgag gtccagttca actggtacgt ggatggcgtg      840
gaggtgcata atgccaagac aaagccgcgg gaggagcagt tcaacagcac gtaccgtgtg      900
gtcagcgtcc tcaccgtcct gcaccaggac tggctgaacg gcaaggagta caagtgcaag      960
gtctccaaca aaggcctccc gtcctccatc gagaaaacca tctccaaagc caaagggcag     1020
ccccgagagc cacaggtgta caccctgccc ccatcccagg aggagatgac caagaaccag     1080
gtcagcctga cctgcctggt caaaggcttc taccccagcg acatcgccgt ggagtgggag     1140
agcaatgggc agccggagaa caactacaag accacgcctc ccgtgctgga ctccgacggc     1200
tccttcttcc tctacagcag gctaaccgtg gacaagagca ggtggcagga ggggaatgtc     1260
ttctcatgct ccgtgatgca tgaggctctg cacaaccact acacacagaa gagcctctcc     1320
ctgtctctgg gtaaatga                                                   1338
```

```
<210> SEQ ID NO 105
<211> LENGTH: 645
<212> TYPE: DNA
<213> ORGANISM: Artificial Sequence
<220> FEATURE:
```

<223> OTHER INFORMATION: HzVSF_V6_LC

<400> SEQUENCE: 105

| | |
|---|---|
| gacatccaga tgacccagtc tccatcctcc ctgtctgcat ctgtaggaga cagagtcacc | 60 |
| atcacttgcc gagcaagtga gaatatttac agtaatttag catggtatca gcagaaacca | 120 |
| gggaaagctc ctaagctcct gatctatgtt gcaacaaact tagcagatgg ggtcccatca | 180 |
| aggttcagcg gcagtggatc tgggacagat ttcactctca ccatcagcag cctgcagcct | 240 |
| gaagattttg caacttatta ctgtcaacat ttttatggtt ctcctcggac gttcggcgga | 300 |
| gggaccaagg tggagatcaa acgtacggtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gttag | 645 |

<210> SEQ ID NO 106
<211> LENGTH: 1338
<212> TYPE: DNA
<213> ORGANISM: Artificial Sequence
<220> FEATURE:
<223> OTHER INFORMATION: HzVSF_V7_HC

<400> SEQUENCE: 106

| | |
|---|---|
| gaggtgcagc tggtgcagtc tggggctgag gtgaagaagc tggggcctc agtgaaggtc | 60 |
| tcctgcaagg cttctggata caccttcacc ggctacaaca tgaactgggt gcgacaggct | 120 |
| cctggaaaag gcttgagtg gatgggaaat attgatcctt actatggtag tgataccat | 180 |
| gcacagaagt ttcagggcag ggtcaccatg accgtagaca cwtccgsmag cacagcctac | 240 |
| atggagctga gcaggctgag atctgacgac acggccgtgt attactgtgc gagagagact | 300 |
| gggacgaggg ctatggacta ctggggtcaa ggaaccctgg tcaccgtctc ctcagcttcc | 360 |
| accaagggcc catccgtctt ccccctggcg ccctgctcca ggagcacctc cgagagcaca | 420 |
| gccgccctgg gctgcctggt caaggactac ttccccgaac cggtgacggt gtcgtggaac | 480 |
| tcaggcgccc tgaccagcgg cgtgcacacc ttcccggctg tcctacagtc ctcaggactc | 540 |
| tactccctca gcagcgtggt gaccgtgccc tccagcagct gggcacgaa gacctacacc | 600 |
| tgcaacgtag atcacaagcc cagcaacacc aaggtggaca gagagttga gtccaaatat | 660 |
| ggtcccccat gcccatcatg cccagcacct gagttcctgg ggggaccatc agtcttcctg | 720 |
| ttccccccaa aacccaagga cactctcatg atctcccgga cccctgaggt cacgtgcgtg | 780 |
| gtggtggacg tgagccagga agaccccgag gtccagttca actggtacgt ggatggcgtg | 840 |
| gaggtgcata atgccaagac aaagccgcgg gaggagcagt tcaacagcac gtaccgtgtg | 900 |
| gtcagcgtcc tcaccgtcct gcaccaggac tggctgaacg gcaaggagta caagtgcaag | 960 |
| gtctccaaca aaggcctccc gtcctccatc gagaaaacca tctccaaagc caagggcag | 1020 |
| ccccgagagc cacaggtgta caccctgccc ccatcccagg aggagatgac caagaaccag | 1080 |
| gtcagcctga cctgcctggt caaaggcttc taccccagcg acatcgccgt ggagtgggag | 1140 |
| agcaatgggc agccggagaa caactacaag accacgcctc ccgtgctgga ctccgacggc | 1200 |
| tccttcttcc tctacagcag gctaaccgtg gacaagagca ggtggcagga ggggaatgtc | 1260 |
| ttctcatgct ccgtgatgca tgaggctctg cacaaccact acacacagaa gagcctctcc | 1320 |

<210> SEQ ID NO 107
<211> LENGTH: 645
<212> TYPE: DNA
<213> ORGANISM: Artificial Sequence
<220> FEATURE:
<223> OTHER INFORMATION: HzVSF_V7_LC

<400> SEQUENCE: 107

```
gacatccaga tgacccagtc tccatcctcc ctgtctgcat ctgtaggaga cagagtcacc    60
atcacttgcc gagcaagtga gaatatttac agtaatttag catggtatca gcagaaacca   120
gggaaagctc ctaagctcct gatctatgtt gcaacaaact tagcagatgg ggtcccatca   180
aggttcagcg gcagtggatc tgggacagat ttcactctca ccatcagcag cctgcagcct   240
gaagattttg caacttatta ctgtcaacat ttttatggtt ctcctcggac gttcggcgga   300
gggaccaagg tggagatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cccctgacg   540
ctgagcaaag cagactacga aaacacaaa gtctacgcct gcgaagtcac ccatcagggc   600
ctgagctcgc ccgtcacaaa gagcttcaac aggggagagt gttag                  645
```

<210> SEQ ID NO 108
<211> LENGTH: 1338
<212> TYPE: DNA
<213> ORGANISM: Artificial Sequence
<220> FEATURE:
<223> OTHER INFORMATION: HzVSF_V8_HC

<400> SEQUENCE: 108

```
gaggtgcagc tggtgcagtc tggggctgag gtgaagaagc ctggggcctc agtgaaggtc    60
tcctgcaagg cttctggata caccttcacc ggctacaaca tgaactgggt gcgacaggct   120
cctggaaaag ggcttgagtg gatgggaaat attgatcctt actatggtag tgataccta   180
gcacagaagt tcagggcag ggtcaccatg accgtagaca cttccgcaag cacagcctac   240
atggagctga gcaggctgag atctgacgac acggccgtgt attactgtgc gagagagact   300
gggaataggg ctatggacta ctggggtcaa ggaaccctgg tcaccgtctc ctcagcttcc   360
accaagggcc catccgtctt ccccctggcg ccctgctcca ggagcacctc cgagagcaca   420
gccgccctgg gctgcctggt caaggactac ttccccgaac cggtgacggt gtcgtggaac   480
tcaggcgccc tgaccagcgg cgtgcacacc ttcccggctg tcctacagtc ctcaggactc   540
tactccctca gcagcgtggt gaccgtgccc tccagcagct gggcacgaa gacctacacc   600
tgcaacgtag atcacaagcc cagcaacacc aaggtggaca gagagttga gtccaaatat   660
ggtcccccat gcccatcatg cccagcacct gagttcctgg ggggaccatc agtcttcctg   720
ttcccccaa acccaaggc cactctcatg atctcccgga cccctgaggt cacgtgcgtg   780
gtggtggacg tgagccagga agaccccgag gtccagttca actggtacgt ggatggcgtg   840
gaggtgcata atgccaagac aaagccgcgg gaggagcagt tcaacagcac gtaccgtgtg   900
gtcagcgtcc tcaccgtcct gcaccaggac tggctgaacg gcaaggagta caagtgcaag   960
gtctccaaca aaggcctccc gtcctccatc gagaaaacca tctccaaagc caagggcag  1020
```

| ccccgagagc cacaggtgta caccctgccc ccatcccagg aggagatgac caagaaccag | 1080 |
| gtcagcctga cctgcctggt caaaggcttc taccccagcg acatcgccgt ggagtgggag | 1140 |
| agcaatgggc agccggagaa caactacaag accacgcctc ccgtgctgga ctccgacggc | 1200 |
| tccttcttcc tctacagcag gctaaccgtg gacaagagca ggtggcagga ggggaatgtc | 1260 |
| ttctcatgct ccgtgatgca tgaggctctg cacaaccact acacacagaa gagcctctcc | 1320 |
| ctgtctctgg gtaaatga | 1338 |

<210> SEQ ID NO 109
<211> LENGTH: 645
<212> TYPE: DNA
<213> ORGANISM: Artificial Sequence
<220> FEATURE:
<223> OTHER INFORMATION: HzVSF_V8_LC

<400> SEQUENCE: 109

| gacatccaga tgacccagtc tccatcctcc ctgtctgcat ctgtaggaga cagagtcacc | 60 |
| atcacttgcc gagcaagtga gaatatttac agtaatttag catggtatca gcagaaacca | 120 |
| gggaaagctc ctaagctcct gatctatgtt gcaacaaact tagcagatgg ggtcccatca | 180 |
| aggttcagcg gcagtggatc tgggacagat ttcactctca ccatcagcag cctgcagcct | 240 |
| gaagattttg caacttatta ctgtcaacat ttttatggtt ctcctcggac gttcggcgga | 300 |
| gggaccaagg tggagatcaa acgtacggtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag cacccrgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gttag | 645 |

<210> SEQ ID NO 110
<211> LENGTH: 1338
<212> TYPE: DNA
<213> ORGANISM: Artificial Sequence
<220> FEATURE:
<223> OTHER INFORMATION: HzVSF_V9_HC

<400> SEQUENCE: 110

| gaggtgcagc tggtgcagtc tggggctgag gtgaagaagc ctggggcctc agtgaaggtc | 60 |
| tcctgcaagg cttctggata caccttcacc ggctacaaca tgaactgggt gcgacaggct | 120 |
| cctggaaaag ggcttgagtg gatgggaaat attgatcctt actatggtag tgatacctat | 180 |
| gcacagaagt tcagggcag gtcaccatg accgtagaca cttccgcaag cacagcctac | 240 |
| atggagctga gcaggctgag atctgacgac acggccgtgt attactgtgc gagagagact | 300 |
| gggacgaggg ctatggacta ctggggtcaa ggaaccctgg tcaccgtctc ctcagcttcc | 360 |
| accaagggcc catccgtctt ccccctggcg ccctgctcca ggagcacctc cgagagcaca | 420 |
| gccgccctgg gctgcctggt caaggactac ttccccgaac cggtgacggt gtcgtggaac | 480 |
| tcaggcgccc tgaccagcgg cgtgcacacc ttcccggctg tcctacagtc ctcaggactc | 540 |
| tactccctca gcagcgtggt gaccgtgccc tccagcagct gggcacgaa gacctacacc | 600 |
| tgcaacgtag atcacaagcc cagcaacacc aaggtggaca agagagttga gtccaaatat | 660 |
| ggtccccat gccatcatg cccagcacct gagttcctgg ggggaccatc agtcttcctg | 720 |
| ttccccccaa aacccaagga cactctcatg atctcccgga cccctgaggt cacgtgcgtg | 780 |

```
gtggtggacg tgagccagga agaccccgag gtccagttca actggtacgt ggatggcgtg    840
gaggtgcata atgccaagac aaagccgcgg gaggagcagt caacagcac gtaccgtgtg     900 gtcagcgtcc tcaccgtcct gcaccaggac tggctgaacg gcaaggagta caagtgcaag    960
gtctccaaca aaggcctccc gtcctccatc gagaaaacca tctccaaagc caagggcag    1020 ccccgagagc cacaggtgta cacctgccc ccatcccagg aggagatgac caagaaccag    1080
gtcagcctga cctgcctggt caaaggcttc taccccagcg acatcgccgt ggagtgggag    1140
agcaatgggc agccggagaa caactacaag accacgcctc ccgtgctgga ctccgacggc    1200
tccttcttcc tctacagcag gctaaccgtg gacaagagca ggtggcagga ggggaatgtc    1260
ttctcatgct ccgtgatgca tgaggctctg cacaaccact acacacagaa gagcctctcc    1320
ctgtctctgg gtaaatga                                                 1338
```

<210> SEQ ID NO 111
<211> LENGTH: 645
<212> TYPE: DNA
<213> ORGANISM: Artificial Sequence
<220> FEATURE:
<223> OTHER INFORMATION: HzVSF_V9_LC

<400> SEQUENCE: 111

```
gacatccaga tgacccagtc tccatcctcc ctgtctgcat ctgtaggaga cagagtcacc     60
atcacttgcc gagcaagtga gaatatttac agtaatttag catggtatca gcagaaacca    120
gggaaagctc ctaagctcct gatctatgtt gcagacaacc gcggagatgg ggtcccatca    180
aggttcagcg gcagtggatc tgggacagat ttcactctca ccatcagcag cctgcagcct    240
gaagattttg caacttatta ctgtcaacat ttttatggtt ctcctcggac gttcggcgga    300
gggaccaagg tggagatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg ataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645
```

<210> SEQ ID NO 112
<211> LENGTH: 1338
<212> TYPE: DNA
<213> ORGANISM: Artificial Sequence
<220> FEATURE:
<223> OTHER INFORMATION: HzVSF_V10_HC

<400> SEQUENCE: 112

```
gaggtgcagc tggtgcagtc tggggctgag gtgaagaagc ctggggcctc agtgaaggtc     60
tcctgcaagg cttctggata caccttcacc ggctacaaca tgaactgggt gcgacaggct    120
cctggaaaag ggcttgagtg gatgggaaat attgatcctt actatggtag tgataccat    180 gcacagaagt tcagggcag gtcaccatg accgtagaca cttccgcaag cacagcctac    240
atggagctga gcaggctgag atctgacgac acggccgtgt attactgtgc gagagagact    300
gggaataggg ctatggacta ctggggtcaa ggaaccctgg tcaccgtctc ctcagcttcc    360 accaaggggcc catccgtctt ccccctggcg ccctgctcca ggagcacctc cgagagcaca    420
gccgccctgg gctgcctggt caaggactac ttccccgaac cggtgacggt gtcgtggaac    480
```

| | | |
|---|---|---|
| tcaggcgccc tgaccagcgg cgtgcacacc ttcccggctg tcctacagtc ctcaggactc | 540 | |
| tactccctca gcagcgtggt gaccgtgccc tccagcagct tgggcacgaa gacctacacc | 600 | |
| tgcaacgtag atcacaagcc cagcaacacc aaggtggaca gagagttga gtccaaatat | 660 | |
| ggtcccccat gcccatcatg cccagcacct gagttcctgg ggggaccatc agtcttcctg | 720 | |
| ttccccccaa acccaagga cactctcatg atctcccgga cccctgaggt cacgtgcgtg | 780 | |
| gtggtggacg tgagccagga agaccccgag gtccagttca actggtacgt ggatggcgtg | 840 | |
| gaggtgcata atgccaagac aaagccgcgg gaggagcagt tcaacagcac gtaccgtgtg | 900 | |
| gtcagcgtcc tcaccgtcct gcaccaggac tggctgaacg gcaaggagta caagtgcaag | 960 | |
| gtctccaaca aaggcctccc gtcctccatc gagaaaacca tctccaaagc caaagggcag | 1020 | |
| ccccgagagc cacaggtgta caccctgccc ccatcccagg aggagatgac caagaaccag | 1080 | |
| gtcagcctga cctgcctggt caaaggcttc taccccagcg acatcgccgt ggagtgggag | 1140 | |
| agcaatgggc agccggagaa caactacaag accacgcctc ccgtgctgga ctccgacggc | 1200 | |
| tccttcttcc tctacagcag gctaaccgtg gacaagagca ggtggcagga ggggaatgtc | 1260 | |
| ttctcatgct ccgtgatgca tgaggctctg cacaaccact acacacagaa gagcctctcc | 1320 | |
| ctgtctctgg gtaaatga | 1338 | |

<210> SEQ ID NO 113
<211> LENGTH: 645
<212> TYPE: DNA
<213> ORGANISM: Artificial Sequence
<220> FEATURE:
<223> OTHER INFORMATION: HzVSF_V10_LC

<400> SEQUENCE: 113

| | | |
|---|---|---|
| gacatccaga tgacccagtc tccatcctcc ctgtctgcat ctgtaggaga cagagtcacc | 60 | |
| atcacttgcc gagcaagtga gaatatttac agtaatttag catggtatca gcagaaacca | 120 | |
| gggaaagctc ctaagctcct gatctatgtt gcagacaacc gcgagatgg ggtcccatca | 180 | |
| aggttcagcg gcagtggatc tgggacagat ttcactctca ccatcagcag cctgcagcct | 240 | |
| gaagattttg caacttatta ctgtcaacat ttttatggtt ctcctcggac gttcggcgga | 300 | |
| gggaccaagg tggagatcaa acgtacggtg gctgcaccat ctgtcttcat cttcccgcca | 360 | |
| tctgatgagc agttgaaatc tggaactgcc tctgttgtgt gcctgctgaa taacttctat | 420 | |
| cccagagagg ccaaagtaca gtggaaggtg gataacgccc tccaatcggg taactcccag | 480 | |
| gagagtgtca cagagcagga cagcaaggac agcacctaca gcctcagcag cacccctgacg | 540 | |
| ctgagcaaag cagactacga gaaacacaaa gtctacgcct gcgaagtcac ccatcagggc | 600 | |
| ctgagctcgc ccgtcacaaa gagcttcaac aggggagagt gttag | 645 | |

<210> SEQ ID NO 114
<211> LENGTH: 1338
<212> TYPE: DNA
<213> ORGANISM: Artificial Sequence
<220> FEATURE:
<223> OTHER INFORMATION: HzVSF_V11_HC

<400> SEQUENCE: 114

| | | |
|---|---|---|
| gaggtgcagc tggtgcagtc tggggctgag gtgaagaagc ctggggcctc agtgaaggtc | 60 | |
| tcctgcaagg cttctggata cacctttacc ggctacaaca tgaactgggt gcgacaggct | 120 | |
| cctggaaaag ggcttgagtg gatgggaaat attgatcctt actatggtag tgataccta t | 180 | |
| gcacagaagt ttcagggcag ggtcaccatg accgtagaca cttccgcaag cacagcctac | 240 | |

-continued

```
atggagctga gcaggctgag atctgacgac acggccgtgt attactgtgc gagagagact      300
gggacgaggg ctatggacta ctggggtcaa ggaaccctgg tcaccgtctc ctcagcttcc      360
accaagggcc catccgtctt ccccctggcg ccctgctcca ggagcacctc cgagagcaca      420
gccgccctgg gctgcctggt caaggactac ttccccgaac cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct gggcacgaa gacctacacc      600 tgcaacgtag atcacaagcc cagcaacacc aaggtggaca gagagttga gtccaaatat      660 ggtcccccat gcccatcatg cccagccct gagttcctgg ggggaccatc agtcttcctg      720
ttccccccaa acccaagga cactctcatg atctcccgga cccctgaggt cacgtgcgtg      780
gtggtggacg tgagccagga agaccccgag gtccagttca actggtacgt ggatggcgtg      840
gaggtgcata atgccaagac aaagccgcgg gaggagcagt tcaacagcac gtaccgtgtg      900
gtcagcgtcc tcaccgtcct gcaccaggac tggctgaacg gcaaggagta caagtgcaag      960
gtctccaaca aaggcctccc gtcctccatc gagaaaacca tctccaaagc caaagggcag      1020
ccccgagagc cacaggtgta caccctgccc ccatcccagg aggagatgac caagaaccag      1080
gtcagcctga cctgcctggt caaaggcttc taccccagcg acatcgccgt ggagtgggag      1140
agcaatgggc agccggagaa caactacaag accacgcctc ccgtgctgga ctccgacggc      1200
tccttcttcc tctacagcag gctaaccgtg gacaagagca ggtggcagga ggggaatgtc      1260
ttctcatgct ccgtgatgca tgaggctctg cacaaccact acacacagaa gagcctctcc      1320
ctgtctctgg gtaaatga                                                    1338
```

<210> SEQ ID NO 115
<211> LENGTH: 645
<212> TYPE: DNA
<213> ORGANISM: Artificial Sequence
<220> FEATURE:
<223> OTHER INFORMATION: HzVSF_V11_LC

<400> SEQUENCE: 115

```
gacatccaga tgacccagtc tccatcctcc ctgtctgcat ctgtaggaga cagagtcacc       60
atcacttgcc gagcaagtga gaatatttac agtaatttag catggtatca gcagaaacca      120
gggaaagctc ctaagctcct gatctatgtt gcagacaacc gcggagatgg ggtcccatca      180
aggttcagcg gcagtggatc tgggacagat ttcactctca ccatcagcag cctgcagcct      240
gaagattttg caacttatta ctgtcaacat ttttatggta cccctcggac gttcggcgga      300
gggaccaagg tggagatcaa acgtacggtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gttag                      645
```

<210> SEQ ID NO 116
<211> LENGTH: 1338
<212> TYPE: DNA
<213> ORGANISM: Artificial Sequence
<220> FEATURE:
<223> OTHER INFORMATION: HzVSF_V12_HC

<400> SEQUENCE: 116

```
gaggtgcagc tggtgcagtc tggggctgag gtgaagaagc ctggggcctc agtgaaggtc      60
tcctgcaagg cttctggata caccttcacc ggctacaaca tgaactgggt gcgacaggct     120
cctggaaaag gcttgagtg gatgggaaat attgatcctt actatggtag tgatacctat     180
gcacagaagt ttcagggcag ggtcaccatg accgtagaca cttccgcaag cacagcctac     240
atggagctga gcaggctgag atctgacgac acggccgtgt attactgtgc gagagagact     300
gggaataggg ctatggacta ctggggtcaa ggaaccctgg tcaccgtctc ctcagcttcc     360
accaagggcc catccgtctt ccccctggcg ccctgctcca ggagcacctc cgagagcaca     420
gccgccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcacgaa gacctacacc      600
tgcaacgtag atcacaagcc cagcaacacc aaggtggaca gagagttga gtccaaatat      660
ggtcccccat gcccatcatg cccagcacct gagttcctgg gggaccatc agtcttcctg      720
ttccccccaa aacccaagga cactctcatg atctcccgga cccctgaggt cacgtgcgtg     780
gtggtggacg tgagccagga agaccccgag gtccagttca actggtacgt ggatggcgtg     840
gaggtgcata atgccaagac aaagccgcgg gaggagcagt tcaacagcac gtaccgtgtg     900
gtcagcgtcc tcaccgtcct gcaccaggac tggctgaacg gcaaggagta caagtgcaag     960
gtctccaaca aaggcctccc gtcctccatc gagaaaacca tctccaaagc caaagggcag    1020
ccccgagagc cacaggtgta caccctgccc ccatcccagg aggagatgac caagaaccag    1080
gtcagcctga cctgcctggt caaaggcttc taccccagcg acatcgccgt ggagtgggag    1140
agcaatgggc agccggagaa caactacaag accacgcctc ccgtgctgga ctccgacggc    1200
tccttcttcc tctacagcag gctaaccgtg gacaagagca ggtggcagga ggggaatgtc    1260
ttctcatgct ccgtgatgca tgaggctctg cacaaccact acacacagaa gagcctctcc    1320
ctgtctctgg gtaaatga                                                  1338
```

<210> SEQ ID NO 117
<211> LENGTH: 645
<212> TYPE: DNA
<213> ORGANISM: Artificial Sequence
<220> FEATURE:
<223> OTHER INFORMATION: HzVSF_V12_LC

<400> SEQUENCE: 117

```
gacatccaga tgacccagtc tccatcctcc ctgtctgcat ctgtaggaga cagagtcacc      60
atcacttgcc gagcaagtga gaatatttac agtaatttag catggtatca gcagaaacca     120
gggaaagctc ctaagctcct gatctatgtt gcagacaacc gcggagatgg ggtcccatca     180
aggttcagcg gcagtggatc tgggacagat ttcactctca ccatcagcag cctgcagcct     240
gaagattttg caacttatta ctgtcaacat ttttatggta cccctcggac gttcggcgga     300
gggaccaagg tggagatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg    540
ctgagcaaag cagactacga gaaacacaaa gtctacgcct gcgaagtcac ccatcagggc     600
ctgagctcgc ccgtcacaaa gagcttcaac aggggagagt gttag                     645
```

<210> SEQ ID NO 118
<211> LENGTH: 1338
<212> TYPE: DNA
<213> ORGANISM: Artificial Sequence
<220> FEATURE:
<223> OTHER INFORMATION: HzVSF_V13_HC

<400> SEQUENCE: 118

```
gaggtgcagc tggtgcagtc tggggctgag gtgaagaagc ctggggcctc agtgaaggtc        60
tcctgcaagg cttctggata caccttcacc ggctacaaca tgaactgggt gcgacaggct       120
cctggaaaag gcttgagtg gatgggaaat attgatcctt actatggtag tgatacctat       180
gcacagaagt ttcagggcag ggtcaccatg accgtagaca atccatcag cacagcctac        240 atggagctga gcaggctgag atctgacgac acggccgtgt attactgtgc gagagagact       300
gggacgaggg ctatggacta ctggggtcaa ggaaccctgg tcaccgtctc ctcagcttcc       360
accaagggcc catccgtctt ccccctggcg ccctgctcca ggagcacctc cgagagcaca       420
gccgccctgg gctgcctggt caaggactac ttccccgaac cggtgacggt gtcgtggaac       480
tcaggcgccc tgaccagcgg cgtgcacacc ttcccggctg tcctacagtc ctcaggactc       540
tactccctca gcagcgtggt gaccgtgccc tccagcagct gggcacgaa gacctacacc        600 tgcaacgtag atcacaagcc cagcaacacc aaggtggaca gagagttga gtccaaatat        660 ggtcccccat gcccatcatg cccagcacct gagttcctgg ggggaccatc agtcttcctg       720 ttcccccccaa aacccaagga cactctcatg atctcccgga cccctgaggt cacgtgcgtg      780
gtggtggacg tgagccagga agaccccgag gtccagttca actggtacgt ggatggcgtg       840
gaggtgcata atgccaagac aaagccgcgg gaggagcagt tcaacagcac gtaccgtgtg       900
gtcagcgtcc tcaccgtcct gcaccaggac tggctgaacg gcaaggagta caagtgcaag       960
gtctccaaca aaggcctccc gtcctccatc gagaaaacca tctccaaagc caaagggcag      1020
ccccgagagc cacaggtgta caccctgccc ccatcccagg aggagatgac caagaaccag      1080
gtcagcctga cctgcctggt caaaggcttc taccccagcg acatcgccgt ggagtgggag      1140
agcaatgggc agccggagaa caactacaag accacgcctc ccgtgctgga ctccgacggc      1200
tccttcttcc tctacagcag gctaaccgtg gacaagagca ggtggcagga ggggaatgtc      1260
ttctcatgct ccgtgatgca tgaggctctg cacaaccact acacacagaa gagcctctcc      1320
ctgtctctgg gtaaatga                                                   1338
```

<210> SEQ ID NO 119
<211> LENGTH: 645
<212> TYPE: DNA
<213> ORGANISM: Artificial Sequence
<220> FEATURE:
<223> OTHER INFORMATION: HzVSF_V13_LC

<400> SEQUENCE: 119

```
gacatccaga tgacccagtc tccatcctcc ctgtctgcat ctgtaggaga cagagtcacc        60
atcacttgcc gagcaagtga gaatatttac agtaatttag catggtatca gcagaaacca       120
gggaaagctc ctaagctcct gatctatgtt gcagacaact tagcagatgg ggtcccatca       180
aggttcagcg gcagtggatc tgggacagat ttcactctca ccatcagcag cctgcagcct       240
gaagattttg caacttatta ctgtcaacat ttttatggtt ctcctcggac gttcggcgga       300
gggaccaagg tggagatcaa acgtacggtg gctgcaccat ctgtcttcat cttcccgcca       360
```

-continued

| | |
|---|---|
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gttag | 645 |

<210> SEQ ID NO 120
<211> LENGTH: 1417
<212> TYPE: DNA
<213> ORGANISM: Artificial Sequence
<220> FEATURE:
<223> OTHER INFORMATION: HzVSF V12_HC_optimization

<400> SEQUENCE: 120

| | |
|---|---|
| aagcttgccg ccaccatgga atggtcctgg gtgttcctgt tcttcctgtc cgtgaccacc | 60 |
| ggcgtgcact ccgaagtgca gctggtgcag tctggcgccg aagtgaagaa acctggcgcc | 120 |
| tccgtgaagg tgtcctgcaa ggcttccggc tacacctta ccggctacaa catgaactgg | 180 |
| gtgcgacagg cccctggcaa gggcctggaa tggatgggca acatcgaccc ctactacggc | 240 |
| tccgacacct acgcccagaa attccagggc agagtgacca tgaccgtgga cacctctgcc | 300 |
| tccaccgcct acatggaact gtcccggctg agatccgacg acaccgccgt gtactactgc | 360 |
| gccagagaga caggcaaccg ggccatggat tattggggcc agggcaccct cgtgaccgtg | 420 |
| tctagcgctt ctaccaaggg cccctccgtg ttccctctgg ccccttgctc cagatccacc | 480 |
| tccgagtcta ccgccgctct gggctgcctc gtgaaggact acttccccga gcccgtgaca | 540 |
| gtgtcctgga actctggcgc tctgacctct ggcgtgcaca ccttccctgc tgtgctgcag | 600 |
| tcctccggcc tgtactccct gtcctccgtc gtgactgtgc cctccagctc tctgggcacc | 660 |
| aagacctaca cctgtaacgt ggaccacaag ccctccaaca ccaaggtgga caagcgggtg | 720 |
| gaatctaagt acggccctcc ctgccctagc tgccctgccc ctgagtttct gggaggccct | 780 |
| tctgtgtttc tgttcccccc aaagcccaag gacaccctga tgatctcccg gacccccgaa | 840 |
| gtgacctgcg tggtggtgga tgtgtcccag gaagatcccg aggtgcagtt caattggtac | 900 |
| gtggacggcg tggaagtgca caacgccaag accaagccta gagaggaaca gttcaactcc | 960 |
| acctaccggg tggtgtccgt gctgaccgtg ctgcaccagg attggctgaa cggcaaagag | 1020 |
| tacaagtgca aggtgtccaa caagggactg cccagctcca tcgaaaagac catctccaag | 1080 |
| gccaagggcc agccccggga acccaggtg tacacactgc ctccaagcca ggaagagatg | 1140 |
| accaagaacc aggtgtccct gacctgtctc gtgaaaggct tctacccctc cgatatcgcc | 1200 |
| gtggaatggg agtccaacgg ccagcctgag aacaactaca agaccacccc cctgtgctg | 1260 |
| gactccgacg gctccttctt tctgtactct cggctgacag tggacaagtc ccggtggcag | 1320 |
| gaaggcaacg tgttcctg cagcgtgatg cacgaggccc tgcacaacca ctacacccag | 1380 |
| aagtccctgt ccctgtctct gggaaagtga tgaattc | 1417 |

<210> SEQ ID NO 121
<211> LENGTH: 727
<212> TYPE: DNA
<213> ORGANISM: Artificial Sequence
<220> FEATURE:
<223> OTHER INFORMATION: HzVSF V12_LC_optimization

<400> SEQUENCE: 121

| | |
|---|---|
| aagcttgccg ccaccatgtc cgtgcctacc caggtgctgg gactgctgct gctgtggctg | 60 |

```
accgacgcca gatgcgacat ccagatgacc cagtccccct ccagcctgtc tgcttccgtg    120
ggcgacagag tgaccatcac ctgtcgggcc tccgagaaca tctactccaa cctggcctgg    180
tatcagcaga agcccggcaa ggccccccaag ctgctgatct acgtggccga caatagaggc    240
gacggcgtgc cctccagatt ctccggctct ggctctggca ccgactttac cctgaccatc    300
agctccctgc agcccgagga cttcgccacc tactactgcc agcacttcta cggcaccccc    360
cggacatttg gcggaggcac caaggtggaa atcaagcgga ccgtggccgc tcccctccgtg    420 ttcatcttcc caccttccga cgagcagctg aagtccggca ccgcttctgt cgtgtgcctg    480
ctgaacaact ctaccccccg cgaggccaag gtgcagtgga aggtggacaa cgccctgcag    540
tccggcaact cccaggaatc cgtgaccgag caggactcca aggacagcac ctactccctg    600
tcctccaccc tgaccctgtc caaggccgac tacgagaagc acaaggtgta cgcctgcgaa    660
gtgacccacc agggcctgtc tagccccgtg accaagtctt tcaaccgggg cgagtgctga    720
tgaattc                                                             727

<210> SEQ ID NO 122
<211> LENGTH: 1417
<212> TYPE: DNA
<213> ORGANISM: Artificial Sequence
<220> FEATURE:
<223> OTHER INFORMATION: HzVSF V13_HC_optimization

<400> SEQUENCE: 122
aagcttgccg ccaccatgga atggtcctgg gtgttcctgt tcttcctgtc cgtgaccacc     60
ggcgtgcact ccgaagtgca gctggtgcag tctggcgccg aagtgaagaa acctggcgcc    120
tccgtgaagg tgtcctgcaa ggcttccggc tacaccttta ccggctacaa catgaactgg    180
gtgcgacagg cccctggcaa gggcctggaa tggatgggca catcgaccc ctactacggc    240 tccgacacct acgcccagaa attccagggc agagtgacca tgaccgtgga caagtccatc    300
tccaccgcct acatggaact gtcccggctg agatccgacg acaccgccgt gtactactgc    360
gccagagaga caggcacccg ggccatggat tattgggggcc agggcaccct cgtgaccgtg    420
tcctctgctt ctaccaaggg ccctccgtg ttccctctgg ccccttgctc cagatccacc    480
tccgagtcta ccgccgctct gggctgcctc gtgaaggact acttccccga gcccgtgaca    540
gtgtcttgga actctggcgc cctgacctct ggcgtgcaca ccttttccagc tgtgctgcag    600 tcctccggcc tgtactccct gtcctccgtc gtgactgtgc cctccagctc tctgggcacc    660
aagacctaca cctgtaacgt ggaccacaag ccctccaaca ccaaggtgga caagcgggtg    720
gaatctaagt acggccctcc ctgccctagc tgccctgccc ctgagtttct gggaggccct    780
tctgtgtttc tgttcccccc aaagcccaag gacaccctga tgatctcccg gacccccgaa    840
gtgacctgcg tggtggtgga tgtgtcccag gaagatcccg aggtgcagtt caattggtac    900
gtggacggcg tggaagtgca caacgccaag accaagccta gagaggaaca gttcaactcc    960
acctaccggg tggtgtccgt gctgaccgtg ctgcaccagg attggctgaa cggcaaagag   1020
tacaagtgca aggtgtccaa caagggactg cccagctcca tcgaaaagac catctccaag   1080
gccaagggcc agccccggga accccaggtg tacacactgc ctccaagcca ggaagagatg   1140
accaagaacc aggtgtccct gacctgtctc gtgaaaggct ctacccctc cgatatcgcc   1200 gtggaatggg agtccaacgg ccagcctgag aacaactaca agaccacccc cctgtgctg   1260 gactccgacg gctccttctt tctgtactct cggctgacag tggataagtc ccggtggcag   1320
```

```
gaaggcaacg tgttctcctg cagcgtgatg cacgaggccc tgcacaacca ctacacccag    1380
aagtccctgt ccctgtctct gggaaagtga tgaattc                             1417

<210> SEQ ID NO 123
<211> LENGTH: 727
<212> TYPE: DNA
<213> ORGANISM: Artificial Sequence
<220> FEATURE:
<223> OTHER INFORMATION: HzVSF V13_LC_optimization

<400> SEQUENCE: 123
aagcttgccg ccaccatgtc cgtgcctacc caggtgctgg gactgctgct gctgtggctg      60
accgacgcca gatgcgacat ccagatgacc cagtccccct ccagcctgtc tgcttccgtg     120
ggcgacagag tgaccatcac ctgtcgggcc tccgagaaca tctactccaa cctggcctgg     180
tatcagcaga agcccggcaa ggcccccaag ctgctgatct acgtggccga taacctggcc     240
gacggcgtgc cctctagatt ctccggctct ggctctggca ccgactttac cctgaccatc     300
agctccctgc agcccgagga cttcgccacc tactactgcc agcacttcta cggctccccc     360
cggacatttg gcggaggcac caaggtggaa atcaagcgga ccgtggccgc tccctccgtg     420
ttcatcttcc caccttccga cgagcagctg aagtccggca ccgcttctgt cgtgtgcctg     480
ctgaacaact ctaccccccg cgaggccaag gtgcagtgga aggtggacaa cgccctgcag     540
tccggcaact cccaggaatc cgtgaccgag caggactcca aggacagcac ctactccctg     600
tcctccaccc tgaccctgtc caaggccgac tacgagaagc acaaggtgta cgcctgcgaa     660
gtgacccacc agggcctgtc tagccccgtg accaagtctt tcaaccgggg cgagtgctga     720
tgaattc                                                              727

<210> SEQ ID NO 124
<211> LENGTH: 25
<212> TYPE: DNA
<213> ORGANISM: Artificial Sequence
<220> FEATURE:
<223> OTHER INFORMATION: mVH F primer

<400> SEQUENCE: 124
cgagctcatg ggatggagct ggatc                                           25

<210> SEQ ID NO 125
<211> LENGTH: 24
<212> TYPE: DNA
<213> ORGANISM: Artificial Sequence
<220> FEATURE:
<223> OTHER INFORMATION: mVH R primer

<400> SEQUENCE: 125
cggtacctga ggagacggtg actg                                            24

<210> SEQ ID NO 126
<211> LENGTH: 37
<212> TYPE: DNA
<213> ORGANISM: Artificial Sequence
<220> FEATURE:
<223> OTHER INFORMATION: KpnI_delR primer

<400> SEQUENCE: 126
gggcccttgg tggaagctga ggagacggtg actgagg                              37

<210> SEQ ID NO 127
<211> LENGTH: 25
```

```
<212> TYPE: DNA
<213> ORGANISM: Artificial Sequence
<220> FEATURE:
<223> OTHER INFORMATION: mVL F primer

<400> SEQUENCE: 127
catcgatatg agtgtgccca ctcag                                         25

<210> SEQ ID NO 128
<211> LENGTH: 24
<212> TYPE: DNA
<213> ORGANISM: Artificial Sequence
<220> FEATURE:
<223> OTHER INFORMATION: mVL R primer

<400> SEQUENCE: 128
cctcgagttt gatttccagc ttgg                                          24

<210> SEQ ID NO 129
<211> LENGTH: 42
<212> TYPE: DNA
<213> ORGANISM: Artificial Sequence
<220> FEATURE:
<223> OTHER INFORMATION: Xho_modR primer

<400> SEQUENCE: 129
agatggtgca gccaccgtgc gtttgatttc agcttggtg cc                       42

<210> SEQ ID NO 130
<211> LENGTH: 354
<212> TYPE: DNA
<213> ORGANISM: Artificial Sequence
<220> FEATURE:
<223> OTHER INFORMATION: ScFv VSF H

<400> SEQUENCE: 130
gagatccagc tgcagcagtc tggagctgag ctggtgaagc ctggggcttc agtgaagata    60
tcctgcaagg cttctggtta ctcattcact ggctacaaca tgaactgggt gaagcagagc   120
catggaaaga gccttgagtg gattggaaat attgatcctt actatggtag tactacctac   180
aatcagaagt tcaagggcaa ggccacattg actgtagaca atcttccag cacagcctac    240 atgcagctca acagcctgac atctgaggac tctgcagtct attactgtgc aagagagact   300
gggacgaggg ctatggacta ctggggtcaa ggaacctcag tcaccgtctc ctca         354

<210> SEQ ID NO 131
<211> LENGTH: 118
<212> TYPE: PRT
<213> ORGANISM: Artificial Sequence
<220> FEATURE:
<223> OTHER INFORMATION: scFv VSF H

<400> SEQUENCE: 131

Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser His Gly Lys Ser Leu Glu Trp Ile
        35                  40                  45

Gly Asn Ile Asp Pro Tyr Tyr Gly Ser Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80
```

```
Met Gln Leu Asn Ser Leu Thr Ser Glu Asp Ser Ala Val Tyr Tyr Cys
                85                  90                  95

Ala Arg Glu Thr Gly Thr Arg Ala Met Asp Tyr Trp Gly Gln Gly Thr
            100                 105                 110

Ser Val Thr Val Ser Ser
        115
```

<210> SEQ ID NO 132
<211> LENGTH: 321
<212> TYPE: DNA
<213> ORGANISM: Artificial Sequence
<220> FEATURE:
<223> OTHER INFORMATION: scFv VSF L3

<400> SEQUENCE: 132

```
gacatccaga tgactcagtc tccagcctcc ctatctgcat ctgtgggaga aactgtcacc     60
atgacatgtc gagcaagtga gaatatttac agtaatttag catggtatca gcagaaacag    120
ggaaaatctc ctcagctcct ggtctatgtt gcaacaaact tagcagatgg tgtgccatca    180
aggttcagtg gcagtggatc aggcacacag ttttctctga agatcaacag cctgcagcct    240
gaagattttg ggagttatta ctgtcaacat ttttatggtt ctcctcggac gttcggtgga    300
ggcaccaagc tggaaatcaa a                                              321
```

<210> SEQ ID NO 133
<211> LENGTH: 107
<212> TYPE: PRT
<213> ORGANISM: Artificial Sequence
<220> FEATURE:
<223> OTHER INFORMATION: scFv VSF L3

<400> SEQUENCE: 133

```
Asp Ile Gln Met Thr Gln Ser Pro Ala Ser Leu Ser Ala Ser Val Gly
1               5                   10                  15

Glu Thr Val Thr Met Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Val Ala Thr Asn Leu Ala Asp Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Phe Tyr Gly Ser Pro Arg
                85                  90                  95

Thr Phe Gly Gly Gly Thr Lys Leu Glu Ile Lys
            100                 105
```

<210> SEQ ID NO 134
<211> LENGTH: 13
<212> TYPE: PRT
<213> ORGANISM: Artificial Sequence
<220> FEATURE:
<223> OTHER INFORMATION: mVSF CDR-L1

<400> SEQUENCE: 134

```
Arg Ala Ser Glu Asn Ile Tyr Ser Asn Leu Ala Trp Tyr
1               5                   10
```

<210> SEQ ID NO 135
<211> LENGTH: 11

-continued

```
<212> TYPE: PRT
<213> ORGANISM: Artificial Sequence
<220> FEATURE:
<223> OTHER INFORMATION: mVSF CDR-L2

<400> SEQUENCE: 135

Leu Leu Val Tyr Val Ala Thr Asn Leu Ala Asp
1               5                   10

<210> SEQ ID NO 136
<211> LENGTH: 9
<212> TYPE: PRT
<213> ORGANISM: Artificial Sequence
<220> FEATURE:
<223> OTHER INFORMATION: mVSF CDR-L3

<400> SEQUENCE: 136

Gln His Phe Tyr Gly Ser Pro Arg Thr
1               5

<210> SEQ ID NO 137
<211> LENGTH: 10
<212> TYPE: PRT
<213> ORGANISM: Artificial Sequence
<220> FEATURE:
<223> OTHER INFORMATION: mVSF CDR-H1

<400> SEQUENCE: 137

Gly Tyr Ser Phe Thr Gly Tyr Asn Met Asn
1               5                   10

<210> SEQ ID NO 138
<211> LENGTH: 20
<212> TYPE: PRT
<213> ORGANISM: Artificial Sequence
<220> FEATURE:
<223> OTHER INFORMATION: mVSF CD

```
                 20                  25                  30

Ala Ser Val Gly Glu Thr Val Thr Met Thr Cys Arg Ala Ser Glu Asn
         35                  40                  45

Ile Tyr Ser Asn Leu Ala Trp Tyr Gln Gln Lys Gln Gly Lys Ser Pro
 50                  55                  60

Gln Leu Leu Val Tyr Val Ala Thr Asn Leu Ala Asp Gly Val Pro Ser
 65                  70                  75                  80

Arg Phe Ser Gly Ser Gly Ser Gly Thr Gln Phe Ser Leu Lys Ile Asn
                 85                  90                  95

Ser Leu Gln Pro Glu Asp Phe Gly Ser Tyr Tyr Cys Gln His Phe Tyr
            100                 105                 110

Gly Ser Pro Arg Thr Phe Gly Gly Gly Thr Lys Leu Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys
145                 150
```

<210> SEQ ID NO 141
<211> LENGTH: 142
<212> TYPE: PRT
<213> ORGANISM: Artificial Sequence
<220> FEATURE:
<223> OTHER INFORMATION: chVSFg4

<400> SEQUENCE: 141

```
Met Gly Trp Ser Trp Ile Phe Leu Phe Leu Leu Ser Val Thr Ala Gly
 1               5                  10                  15

Val His Ser Glu Ile Gln Leu Gln Gln Ser Gly Ala Glu Leu Val Lys
                 20                  25                  30

Pro Gly Ala Ser Val Lys Ile Ser Cys Lys Ala Ser Gly Tyr Ser Phe
         35                  40                  45

Thr Gly Tyr Asn Met Asn Trp Val Lys Gln Ser His Gly Lys Ser Leu
 50                  55                  60

Glu Trp Ile Gly Asn Ile Asp Pro Tyr Tyr Gly Ser Thr Thr Tyr Asn
65                   70                  75                  80

Gln Lys Phe Lys Gly Lys Ala Thr Leu Thr Val Asp Lys Ser Ser Ser
                 85                  90                  95

Thr Ala Tyr Met Gln Leu Asn Ser Leu Thr Ser Glu Asp Ser Ala Val
            100                 105                 110

Tyr Tyr Cys Ala Arg Glu Thr Gly Thr Arg Ala Met Asp Tyr Asn Gly
            115                 120                 125

Gln Gly Thr Ser Val Thr Val Ser Ser Gly Thr Ala Ser Thr
        130                 135                 140
```

<210> SEQ ID NO 142
<211> LENGTH: 131
<212> TYPE: PRT
<213> ORGANISM: Artificial Sequence
<220> FEATURE:
<223> OTHER INFORMATION: chVSFg2

<400> SEQUENCE: 142

```
Glu Ile Gln Leu Gln Gln Ser Gly Ala Glu Leu Val Lys Pro Gly Ala
 1               5                  10                  15

Ser Val Lys Ile Ser Cys Lys Ala Ser Gly Tyr Ser Phe Thr Gly Tyr
                 20                  25                  30
```

-continued

Asn Met Asn Trp Val Lys Gln Ser His Gly Lys Ser Leu Glu Trp Ile
           35                  40                  45

Gly Asn Ile Asp Pro Tyr Tyr Gly Ser Thr Thr Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Gln Leu Asn Ser Leu Thr Ser Glu Asp Ser Ala Val Tyr Tyr Cys
               85                  90                  95

Ala Arg Glu Thr Gly Thr Arg Ala Met Asp Tyr Trp Gly Gln Gly Thr
              100                 105                 110

Ser Val Thr Val Ser Ser Ala Ser Thr Lys Gly Pro Ser Val Phe Pro
              115                 120                 125

Leu Ala Pro
   130

<210> SEQ ID NO 143
<211> LENGTH: 234
<212> TYPE: PRT
<213> ORGANISM: Artificial Sequence
<220> FEATURE:
<223> OTHER INFORMATION: chVSF light chain

<400> SEQUENCE: 143

Met Ser Val Pro Thr Gln Val Leu Gly Leu Leu Leu Leu Trp Leu Thr
  1               5                  10                  15

Gly Ala Arg Cys Asp Ile Gln Met Thr Gln Ser Pro Ala Ser Leu Ser
               20                  25                  30

Ala Ser Val Gly Glu Thr Val Thr Met Thr Cys Arg Ala Ser Glu Asn
           35                  40                  45

Ile Tyr Ser Asn Leu Ala Trp Tyr Gln Gln Lys Gln Gly Lys Ser Pro
 50                  55                  60

Gln Leu Leu Val Tyr Val Ala Thr Asn Leu Ala Asp Gly Val Pro Ser
 65                  70                  75                  80

Arg Phe Ser Gly Ser Gly Ser Gly Thr Gln Phe Ser Leu Lys Ile Asn
               85                  90                  95

Ser Leu Gln Pro Glu Asp Phe Gly Ser Tyr Tyr Cys Gln His Phe Tyr
              100                 105                 110

Gly Ser Pro Arg Thr Phe Gly Gly Gly Thr Lys Leu Glu Ile Lys Arg
              115                 120                 125

Thr Val Ala Ala Pro Ser Val Phe Ile Phe Pro Pro Ser Asp Glu Gln
   130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
              180                 185                 190

Tyr Ser Leu Ser Ser Thr Leu Thr Leu Ser Lys Ala Asp Tyr Glu Lys
              195                 200                 205

His Lys Val Tyr Ala Cys Glu Val Thr His Gln Gly Leu Ser Ser Pro
   210                 215                 220

Val Thr Lys Ser Phe Asn Arg Gly Glu Cys
225                 230

<210> SEQ ID NO 144
<211> LENGTH: 234

<212> TYPE: PRT
<213> ORGANISM: Artificial Sequence
<220> FEATURE:
<223> OTHER INFORMATION: hCk - mVL

<400> SEQUENCE: 144

| | | | | | | | | | | | | | | |
|---|---|---|---|---|---|---|---|---|---|---|---|---|---|---|
| Met | Ser | Val | Pro | Thr | Gln | Val | Arg | Gly | Leu | Leu | Leu | Trp | Leu | Thr |
| 1 | | | | 5 | | | | | 10 | | | | | 15 |
| Gly | Ala | Arg | Cys | Asp | Ile | Gln | Met | Thr | Gln | Ser | Pro | Ala | Ser | Leu | Ser |
| | | | 20 | | | | | 25 | | | | | 30 | | |
| Ala | Ser | Val | Gly | Glu | Thr | Val | Thr | Met | Thr | Cys | Arg | Ala | Ser | Glu | Asn |
| | | | 35 | | | | | 40 | | | | | 45 | | |
| Ile | Tyr | Ser | Asn | Leu | Ala | Trp | Tyr | Gln | Gln | Lys | Gln | Gly | Lys | Ser | Pro |
| | 50 | | | | | 55 | | | | | 60 | | | | |
| Gln | Leu | Leu | Val | Tyr | Val | Ala | Thr | Asn | Leu | Ala | Asp | Gly | Val | Pro | Ser |
| 65 | | | | | 70 | | | | | 75 | | | | | 80 |
| Arg | Phe | Ser | Gly | Ser | Gly | Ser | Gly | Thr | Gln | Phe | Ser | Leu | Met | Ile | Asn |
| | | | | 85 | | | | | 90 | | | | | 95 | |
| Ser | Leu | Gln | Pro | Glu | Asp | Phe | Gly | Ser | Tyr | Tyr | Cys | Gln | His | Phe | Tyr |
| | | | 100 | | | | | 105 | | | | | 110 | | |
| Gly | Pro | Pro | Arg | Thr | Phe | Gly | Gly | Gly | Thr | Lys | Leu | Glu | Ile | Lys | Leu |
| | | | 115 | | | | | 120 | | | | | 125 | | |
| Glu | Val | Ala | Ala | Pro | Ser | Val | Phe | Ile | Phe | Pro | Pro | Ser | Asp | Glu | Gln |
| | 130 | | | | | 135 | | | | | 140 | | | | |
| Leu | Lys | Ser | Gly | Thr | Ala | Ser | Val | Val | Cys | Leu | Leu | Asn | Asn | Phe | Tyr |
| 145 | | | | | 150 | | | | | 155 | | | | | 160 |
| Pro | Arg | Glu | Ala | Lys | Val | Gln | Trp | Lys | Val | Asp | Asn | Ala | Leu | Gln | Ser |
| | | | | 165 | | | | | 170 | | | | | 175 | |
| Gly | Asn | Ser | Gln | Glu | Ser | Val | Thr | Glu | Gln | Asp | Ser | Lys | Asp | Ser | Thr |
| | | | 180 | | | | | 185 | | | | | 190 | | |
| Tyr | Ser | Leu | Ser | Ser | Thr | Leu | Thr | Leu | Ser | Lys | Ala | Asp | Tyr | Glu | Lys |
| | | | 195 | | | | | 200 | | | | | 205 | | |
| His | Lys | Val | Tyr | Ala | Cys | Glu | Val | Thr | His | Gln | Gly | Leu | Ser | Ser | Pro |
| | 210 | | | | | 215 | | | | | 220 | | | | |
| Val | Thr | Lys | Ser | Phe | Asn | Arg | Gly | Glu | Cys | | | | | | |
| 225 | | | | | 230 | | | | | | | | | | |

<210> SEQ ID NO 145
<211> LENGTH: 705
<212> TYPE: DNA
<213> ORGANISM: Artificial Sequence
<220> FEATURE:
<223> OTHER INFORMATION: hCk - mVL

<400> SEQUENCE: 145

| | | |
|---|---|---|
| atgagtgtgc ccactcaggt ccgggggttg ctgctgctgt ggcttacagg tgccagatgt | 60 |
| gacatccaga tgactcagtc tccagcctcc ctatctgcat ctgtgggaga aactgtcacc | 120 |
| atgacatgtc gagcaagtga gaatatttac agtaatttag catggtatca gcagaaacag | 180 |
| ggaaaatctc ctcagctcct ggtctatgtt gcaacaaact agcagatgg tgtgccatca | 240 |
| aggttcagtg gcagtggatc aggcacacag ttttctctga tgatcaacag cctgcagcct | 300 |
| gaagattttg ggagttatta ctgtcaacat ttttatggtc ctcctcggac gttcggtgga | 360 |
| ggcaccaagc tggaaatcaa actcgaggtg gctgcaccat ctgtcttcat cttcccgcca | 420 |
| tctgatgagc agttgaaatc tggaactgcc tctgttgtgt gcctgctgaa taacttctat | 480 |
| cccagagagg ccaaagtaca gtggaaggtg gataacgccc tccaatcggg taactcccag | 540 |

```
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttag                   705
```

<210> SEQ ID NO 146
<211> LENGTH: 465
<212> TYPE: PRT
<213> ORGANISM: Artificial Sequence
<220> FEATURE:
<223> OTHER INFORMATION: hCr2 - mVH

<400> SEQUENCE: 146

```
Met Gly Trp Ser Trp Ile Phe Leu Phe Leu Leu Ser Val Thr Ala Gly
1               5                   10                  15

Val His Ser Glu Ile Gln Leu Gln Gln Ser Gly Ala Glu Leu Val Lys
            20                  25                  30

Pro Gly Ala Ser Val Lys Ile Ser Cys Lys Ala Ser Gly Tyr Ser Phe
        35                  40                  45

Thr Gly Tyr Asn Met Asn Trp Val Lys Gln Ser His Gly Lys Ser Leu
    50                  55                  60

Glu Trp Ile Gly Asn Ile Asp Pro Tyr Tyr Gly Ser Thr Thr Tyr Asn
65                  70                  75                  80

Gln Lys Phe Lys Gly Lys Ala Thr Leu Thr Val Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Ala Arg Glu Thr Gly Thr Arg Ala Met Asp Tyr Trp Gly
        115                 120                 125

Gln Gly Thr Ser Val Thr Val Ser Ser Gly Thr Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335
```

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Asn Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 147
<211> LENGTH: 1398
<212> TYPE: DNA
<213> ORGANISM: Artificial Sequence
<220> FEATURE:
<223> OTHER INFORMATION: hCr2 - mVH

<400> SEQUENCE: 147

```
atgggatgga gctggatctt tctcttcctt ctgtcagtaa ctgcaggtgt ccactctgag      60
atccagctgc agcagtctgg agctgagctg gtgaagcctg gggcttcagt gaagatatcc     120
tgcaaggctt ctggttactc attcactggc tacaacatga actgggtgaa gcagagccat     180
ggaaagagcc ttgagtggat tggaaatatt gatccttact atggtagtac tacctacaat     240
cagaagttca aggcaaggc cacattgact gtagacaaat cttccagcac agcctacatg     300
cagctcaaca gcctgacatc tgaggactct gcagtctatt actgtgcaag agagactggg     360
acgagggcta tggactactg gggtcaagga acctcagtca ccgtctcctc aggtaccgcc     420
tccaccaagg gcccatcggt cttccccctg gcgccctgct ccaggagcac ctccgagagc     480
acagcggccc tgggctgcct ggtcaaggac tacttccccg aaccggtgac ggtgtcgtgg     540
aactcaggcg ctctgaccag cggcgtgcac accttcccgg ctgtcctaca gtcctcagga     600
ctctactccc tcagcagcgt ggtgaccgtg ccctccagca cttcggcac ccagacctac     660
acctgcaacg tagatcacaa gcccagcaac accaaggtgg acaagacagt tgagcgcaaa     720
tgttgtgtcg agtgcccacc gtgcccagca ccacctgtgg caggaccgtc agtcttcctc     780
ttccccccaa aacccaagga caccctcatg atctcccgga cccctgaggt cacgtgcgtg     840
gtggtggacg tgagccacga agaccccgag gtccagttca actggtacgt ggacggcgtg     900
gaggtgcata atgccaagac aaagccacgg gaggagcagt tcaacagcac gttccgtgtg     960
gtcagcgtcc tcaccgtcgt gcaccaggac tggctgaacg gcaaggagta caagtgcaag    1020
gtctccaaca aaggcctccc agcccccatc gagaaaacca tctccaaaac caaagggcag    1080
ccccgagaac cacaggtgta caccctgccc ccatcccggg aggagatgac caagaaccag    1140
gtcagcctga cctgcctggt caaaggcttc taccccagcg acatcgccgt ggagtgggag    1200
agcaatgggc agccggagaa caactacaac accacacctc ccatgctgga ctccgacggc    1260
```

```
tccttcttcc tctacagcaa gctcaccgtg acaagagca ggtggcagca ggggaacgtc   1320
ttctcatgct ccgtgatgca tgaggctctg cacaaccact acacgcagaa gagcctctcc   1380
ctgtctccgg gtaaatga                                                 1398
```

<210> SEQ ID NO 148
<211> LENGTH: 466
<212> TYPE: PRT
<213> ORGANISM: Artificial Sequence
<220> FEATURE:
<223> OTHER INFORMATION: hCr4 - mVH

<400> SEQUENCE: 148

```
Met Gly Trp Ser Trp Ile Phe Leu Phe Leu Leu Ser Val Thr Ala Gly
1               5                   10                  15

Val His Ser Glu Ile Gln Leu Gln Gln Ser Gly Ala Glu Leu Val Lys
            20                  25                  30

Pro Gly Ala Ser Val Lys Ile Ser Cys Lys Ala Ser Gly Tyr Ser Phe
        35                  40                  45

Thr Gly Tyr Asn Met Asn Trp Val Lys Gln Ser His Gly Lys Ser Leu
    50                  55                  60

Glu Trp Ile Gly Asn Ile Asp Pro Tyr Tyr Gly Ser Thr Thr Tyr Asn
65                  70                  75                  80

Gln Lys Phe Lys Gly Lys Ala Thr Leu Thr Val Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Ala Arg Glu Thr Gly Thr Arg Ala Met Asp Tyr Trp Gly
        115                 120                 125

Gln Gly Thr Ser Val Thr Val Ser Ser Gly Thr Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Ser Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335
```

Glu Tyr Lys Cys Lys Val Ser Asn Lys Gly Leu Pro Ser Ser Ile Glu
                340                 345                 350

Lys Thr Ile Ser Lys Ala Lys Gly Gln Pro Arg Glu Pro Gln Val Tyr
            355                 360                 365

Thr Leu Pro Pro Ser Gln Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys
465

<210> SEQ ID NO 149
<211> LENGTH: 1401
<212> TYPE: DNA
<213> ORGANISM: Artificial Sequence
<220> FEATURE:
<223> OTHER INFORMATION: hCr4 - mVH

<400> SEQUENCE: 149

| | | |
|---|---|---|
| atgggatgga gctggatctt tctcttcctt ctgtcagtaa ctgcaggtgt ccactctgag | 60 |
| atccagctgc agcagtctgg agctgagctg gtgaagcctg ggcttcagt gaagatatcc | 120 |
| tgcaaggctt ctggttactc attcactggc tacaacatga actgggtgaa gcagagccat | 180 |
| ggaaagagcc ttgagtggat tggaaatatt gatccttact atggtagtac tacctacaat | 240 |
| cagaagttca gggcaaggc cacattgact gtagacaaat cttccagcac agcctacatg | 300 |
| cagctcaaca gcctgacatc tgaggactct gcagtctatt actgtgcaag agagactggg | 360 |
| acgagggcta tggactactg gggtcaagga acctcagtca ccgtctcctc aggtaccgct | 420 |
| tccaccaagg gcccatccgt cttccccctg gcgccctgct ccaggagcac ctccgagagc | 480 |
| acagccgccc tgggctgcct ggtcaaggac tacttcccg aaccggtgac ggtgtcgtgg | 540 |
| aactcaggcg ccctgaccag cggcgtgcac accttcccgg ctgtcctaca gtcctcagga | 600 |
| ctctactccc tcagcagcgt ggtgaccgtg ccctccagca gcttgggcac gaagacctac | 660 |
| acctgcaacg tagatcacaa gcccagcaac accaaggtgg acaagagagt tgagtccaaa | 720 |
| tatggtcccc catgcccatc atgcccagca cctgagttcc tggggggacc atcagtcttc | 780 |
| ctgttccccc caaaacccaa ggacactctc atgatctccc ggaccctga ggtcacgtgc | 840 |
| gtggtggtgg acgtgagcca ggaagacccc gaggtccagt tcaactggta cgtggatggc | 900 |
| gtggaggtgc ataatgccaa gacaaagccg cgggaggagc agttcaacag cacgtaccgt | 960 |
| gtggtcagcg tcctcaccgt cctgcaccag gactggctga acggcaagga gtacaagtgc | 1020 |
| aaggtctcca acaaaggcct cccgtcctcc atcgagaaaa ccatctccaa agccaaaggg | 1080 |
| cagccccgag agccacaggt gtacaccctg cccccatccc aggaggagat gaccaagaac | 1140 |
| caggtcagcc tgacctgcct ggtcaaaggc ttctacccca gcgacatcgc cgtggagtgg | 1200 |
| gagagcaatg ggcagccgga gaacaactac aagaccacgc ctcccgtgct ggactccgac | 1260 |

```
ggctccttct tcctctacag caggctaacc gtggacaaga gcaggtggca ggagggaat    1320 gtcttctcat gctccgtgat gcatgaggct ctgcacaacc actacacaca gaagagcctc    1380
tccctgtctc tgggtaaatg a                                              1401
```

<210> SEQ ID NO 150
<211> LENGTH: 851
<212> TYPE: DNA
<213> ORGANISM: Artificial Sequence
<220> FEATURE:
<223> OTHER INFORMATION: scFv VSF DNA

<400> SEQUENCE: 150

```
cgtcgacgag atccagctgc agcagtctga gatccagctg cagcagtctg gagctgagct    60
ggtgaagcct ggggcttcag tgaagatatc ctgcaaggct tctggttact cattcactgg    120
ctacaacatg aactgggtga agcagagcca tggaaagagc cttgagtgga ttggaaatat    180
tgatccttac tatggtagta ctacctacaa tcagaagttc aagggcaagg ccacattgac    240
tgtagacaaa tcttccagca cagcctacat gcagctcaac agcctgacat ctgaggactc    300
tgcagtctat tactgtgcaa gagactgg gacgagggct atggactact ggggtcaagg    360
aacctcagtc accgtctcct cacctgga tcagtggcag aggagtccac ctcacgagac    420
cacccctcct aggccacctc aggaggatcc ggtggaggtg gctctggtgg aggtggctct    480
gacatccaga tgactcagtc gacatccaga tgactcagtc tccagcctcc ctatctgcat    540
ctgtgggaga aactgtcacc atgacatgtc gagcaagtga gaatatttac agtaatttag    600
catggtatca gcagaaacag ggaaaatctc ctcagctcct ggtctatgtt gcaacaaact    660
tagcagatgg tgtgccatca aggttcagtg gcagtggatc aggcacacag ttttctctga    720
agatcaacag cctgcagcct gaagattttg ggagttatta ctgtcaacat ttttatggtt    780
ctcctcggac gttcggtgga ggcaccaagc tggaaatcaa accgtggtt cgacctttag    840 tttggagctc c                                                         851
```

<210> SEQ ID NO 151
<211> LENGTH: 30
<212> TYPE: PRT
<213> ORGANISM: Artificial Sequence
<220> FEATURE:
<223> OTHER INFORMATION: FR1 of heavy chain

<400> SEQUENCE: 151

Glu Ile Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr
            20                  25                  30

<210> SEQ ID NO 152
<211> LENGTH: 14
<212> TYPE: PRT
<213> ORGANISM: Artificial Sequence
<220> FEATURE:
<223> OTHER INFORMATION: FR2 of heavy chain

<400> SEQUENCE: 152

Trp Val Arg Gln Ala Pro Gly Lys Gly Leu Glu Trp Ile Gly
1               5                   10

<210> SEQ ID NO 153
<211> LENGTH: 18

```
<212> TYPE: DNA
<213> ORGANISM: Artificial Sequence
<220> FEATURE:
<223> OTHER INFORMATION: HBV cccDNA primer

<400> SEQUENCE: 153
tgaatccygc ggacgacc                                              18

<210> SEQ ID NO 154
<211> LENGTH: 20
<212> TYPE: DNA
<213> ORGANISM: Artificial Sequence
<220> FEATURE:
<223> OTHER INFORMATION: HBV cccDNA primer R

<400> SEQUENCE: 154
cagcttggag gcttgaacag                                            20

<210> SEQ ID NO 155
<211> LENGTH: 18
<212> TYPE: DNA
<213> ORGANISM: Artificial Sequence
<220> FEATURE:
<223> OTHER INFORMATION: HBV total DNA primer F

<400> SEQUENCE: 155
cctcttcatc ctgctgct                                              18

<210> SEQ ID NO 156
<211> LENGTH: 19
<212> TYPE: DNA
<213> ORGANISM: Artificial Sequence
<220> FEATURE:
<223> OTHER INFORMATION: HBV total DNA primer R

<400> SEQUENCE: 156
aactgaaagc caaacagtg                                             19

<210> SEQ ID NO 157
<211> LENGTH: 20
<212> TYPE: DNA
<213> ORGANISM: Artificial Sequence
<220> FEATURE:
<223> OTHER INFORMATION: HCV target primer F

<400> SEQUENCE: 157
gggctataag gtgctagtgc                                            20

<210> SEQ ID NO 158
<211> LENGTH: 20
<212> TYPE: DNA
<213> ORGANISM: Artificial Sequence
<220> FEATURE:
<223> OTHER INFORMATION: HCV target primer R

<400> SEQUENCE: 158
ggctgccagt ggtaattgtt                                            20

<210> SEQ ID NO 159
<211> LENGTH: 20
<212> TYPE: DNA
<213> ORGANISM: Artificial Sequence
<220> FEATURE:
<223> OTHER INFORMATION: GAPDH primer F

<400> SEQUENCE: 159
```

```
tccctgagct gaacgggaag                                              20

<210> SEQ ID NO 160
<211> LENGTH: 20
<212> TYPE: DNA
<213> ORGANISM: Artificial Sequence
<220> FEATURE:
<223> OTHER INFORMATION: GAPDH primer R

<400> SEQUENCE: 160
ggaggagtgg gtgtcgctgt                                              20

<210> SEQ ID NO 161
<211> LENGTH: 20
<212> TYPE: DNA
<213> ORGANISM: Artificial Sequence
<220> FEATURE:
<223> OTHER INFORMATION: HCV target primer F-2

<400> SEQUENCE: 161
atgcagccca agggtataag                                              20

<210> SEQ ID NO 162
<211> LENGTH: 23
<212> TYPE: DNA
<213> ORGANISM: Artificial Sequence
<220> FEATURE:
<223> OTHER INFORMATION: HCV target primer R-2

<400> SEQUENCE: 162
ggttctgatg ttagggtcga tac                                          23
```

METHOD FOR TREATING SKIN DISEASES USING A HUMANIZED ANTIBODY THAT BINDS TO VIMENTIN

CROSS-REFERENCE TO RELATED APPLICATIONS

This application is the U.S. National Phase under 35 U.S.C. § 371 of International Application PCT/KR2018/010049, filed Aug. 30, 2018, designating the U.S., and published in Korean as WO 2019/045477 on Mar. 7, 2019 which claims priority to Korean Patent Application No. 10-2017-0110924, filed Aug. 31, 2017, and International Application No. PCT/KR2017/013706, filed Nov. 28, 2017, the entire contents of which are incorporated herein by reference.

SEQUENCE LISTING STATEMENT

The present application contains a Sequence Listing, which is being submitted via EFS-Web on even date herewith. The Sequence Listing is submitted in a file entitled "OPA18283-US_Sequence_listing.txt," which was created on Feb. 4, 2020, and is approximately 206 kb in size. This Sequence Listing is hereby incorporated by reference.

TECHNICAL FIELD

The present invention relates to a pharmaceutical composition for preventing or treating skin diseases including, as an active ingredient, a material which specifically binds to a peptide derived from isolated vimentin. Specifically, the present invention relates to a pharmaceutical composition, a cosmetic composition, a quasi-drug composition, and an external skin preparation for preventing or treating skin diseases including, as an active ingredient, an antibody which specifically binds to a peptide of SEQ ID NO: 1 or a fragment binding to the peptide, a method for preventing or treating skin diseases, therapeutic use thereof, and use thereof for the preparation of medicine, cosmetics, quasi-drugs or external skin preparations, etc.

BACKGROUND ART

Skin disease refers to all abnormalities occurring in the skin of animals including humans. In modern society, various skin diseases, which had not occurred in the past, have been emerging due to various harmful substances, as the industrialization is advanced. In particular, as time passes, the proliferation or metabolism of skin cells is weakened, resulting in the progression of natural aging, whereby the elasticity of skin tissues is reduced or wrinkles are formed. Additionally, a variety of skin lesions may occur due to long-term exposure to direct sunlight, burns, abrasions, etc., which may damage healthy skin. Such skin lesions caused by natural aging or accidents lead to a decrease in the defensive function of the skin, which is found in the outermost part of the human body, and thus provide the cause of infection by viruses, microorganisms, bacteria, etc., thereby contributing to the development of various skin diseases.

Atopic dermatitis, a representative disease of which the specific etiology has not been identified, is a chronic inflammatory skin disease that occurs mostly during infancy or childhood, whose symptoms improve and worsen repeatedly, and may be exacerbated by infections, mental stress, seasonal and climate changes, irritation and allergens. Although atopic dermatitis is considered to be a genetic disease implicated with immunological abnormalities, its specific etiology has not yet been identified. The cause of other skin diseases, such as psoriasis, lichen simplex chronicus, etc., is also unknown.

Anti-inflammatory agents and antiviral agents composed of chemical drugs, or plant extract- or natural product-derived compounds are currently being utilized, most of the time, in the treatment of skin diseases such as atopic dermatitis, psoriasis, lichen simplex chronicus, pityriasis rosea, etc., of which the specific etiology has not yet been identified. For example, Korean Patent No. 10-1741281 discloses "a pharmaceutical composition including A3 adenosine receptor agonist (IB-MECA/CF-101) tor treatment of psoriasis", and Korean Application Publication No. 10-2017-0041149 discloses "a composition for ameliorating atopic skin containing an enzymatically hydrolyzed Aronia extract and Orostachys japonicus extract.

However, the probability of completely curing such skin diseases by these treatment methods is rather low, and since the methods are not a therapeutic agent targeting only the skin tissue and skin cells of the affected area, the treatment efficiency is somewhat low, and there is a relatively high possibility of side effects.

DISCLOSURE

Technical Problem

Under the circumstances, the present inventors have made extensive efforts to solve the problems described above. As a result, it was confirmed, when a material which specifically binds to a vimentin-derived peptide, specifically, an antibody which specifically binds to a peptide of SEQ ID NO: 1, is applied to the skin tissue of patients suffering from various skin diseases, of which the specific etiology has not yet been clarified, these skin diseases can be effectively treated, thereby completing the present invention.

Technical Solution

One object of the present invention is to provide a pharmaceutical composition for preventing or treating skin diseases, including, as an active ingredient, a material which specifically binds to a peptide of SEQ ID NO: 1.

Another object of the present invention is to provide a cosmetic composition for preventing or ameliorating skin diseases, including, as an active ingredient, a material which specifically binds to a peptide of SEQ ID NO: 1.

Still another object of the present invention is to provide a quasi-drug composition for preventing or ameliorating skin diseases, including, as an active ingredient, a material which specifically binds to a peptide of SEQ NO: 1.

Still another object of the present invention is to provide an external skin preparation for preventing or ameliorating skin diseases, including, as an active ingredient, a material which specifically binds to a peptide of SEQ ID NO: 1.

Still another object of the present invention is to provide a method for preventing or treating skin diseases, including administering a composition including, as an active ingredient, a material which specifically binds to a peptide of SEQ ID NO: 1 to a subject.

Still another object of the present invention is to provide the use of a composition for preventing or treating skin diseases, including, as an active ingredient, a material which specifically binds to a peptide of SEQ ID NO: 1.

Still another object of the present invention is to provide the use of a composition including, as an active ingredient, a material which specifically binds to a peptide of SEQ ID NO: 1 for the preparation of medicine in the prevention or treatment of skin diseases.

Still another object of the present invention is to provide the use of a composition including, as an active ingredient, a material which specifically binds to a peptide of SEQ NO: 1 for the preparation of cosmetics, quasi-drugs, or external skin preparations in the amelioration of skin diseases.

Advantageous Effects

The material which specifically binds to the peptide of SEQ ID NO: 1, more specifically, an antibody which specifically binds to the peptide of SEQ ID NO: 1 or a fragment binding to the peptide can effectively prevent and treat skin diseases expressing a vimentin-derived peptide, and thus can be effectively used as a therapeutic agent for various skin diseases, of which the specific etiology has not yet been clarified.

BRIEF DESCRIPTION OF DRAWINGS

FIG. 1 is a schematic diagram of a vector for the preparation of chimeric VSF.

FIG. 2 is a schematic diagram of chimeric VSF.

FIG. 3 is a diagram confirming the expression of chimeric VSF.

FIG. 4 is a diagram showing the DNA sequence of scFv of VSF.

FIG. 5 is a schematic diagram showing the cloning of scFv of VSF into a vector.

FIG. 6 is a diagram confirming scFV of VSF after purification.

FIG. 7 is a schematic diagram of a vector for the preparation of hzVSF, a humanized antibody.

FIG. 8 is a schematic diagram of hzVSF, a humanized antibody of the present invention.

FIG. 9 is a diagram showing the expression of hzVSF, a humanized antibody.

FIG. 10 is a diagram showing the results of reducing and non-reducing SDS-PAGE, which confirmed the physical properties of hzVSF_var13, a humanized antibody.

FIG. 11 is a diagram showing the LC/MS results, which confirmed the physical properties of hzVSF_var13, a humanized antibody.

FIG. 12 is a diagram showing the SEC-HPLC results, which confirmed the physical properties of hzVSF_var13, a humanized antibody.

FIG. 13 is a diagram showing IF (Isoelectric focusing), which confirmed the physical properties of hzVSF_var13, a humanized antibody.

FIG. 14 is a diagram showing the number of donors with T cell proliferation in response to KLH, hzVSF_var12, and hzVSF_var13 among 51 blood donors.

FIG. 15 is a diagram showing the degree of T cell proliferation of 51 donors in response to hzVSF_var12 and hzVSF_var13, which are representative variants of hzVSF, a humanized antibody.

FIG. 16 is a diagram showing T cell proliferation induced by KLH, hzVSF_var12 and hzVSF_var13 in terms of mean SI values.

FIG. 17 is a diagram showing the results of reactivity between human normal tissues and VSF.

FIG. 18 is a diagram confirming VR expression in various skin diseases.

FIG. 19 is a diagram confirming VR expression in pityriasis rosea, herpes zoster, lichen simplex chronicus, herpes simplex, nummular eczema, and molluscum contagiosum.

FIG. 20 is a diagram confirming VR expression in psoriasis, verruca vulgaris, atopic dermatitis and allergic contact dermatitis.

FIG. 21 a diagram confirming the therapeutic efficacy of VSF in patient 1 with psoriasis.

FIG. 22 is a diagram confirming the therapeutic efficacy of VSF in patient 2 with psoriasis.

FIG. 23 is a diagram confirming the therapeutic efficacy of VSF in patient 1 with lichen simplex chronicus.

FIG. 24 is a diagram confirming the therapeutic efficacy of VSF in patient 2 with lichen simplex chronicus.

FIG. 25 is a diagram confirming the therapeutic efficacy of VSF in patient 3 with lichen simplex chronicus.

FIG. 26 is a diagram confirming the therapeutic efficacy of VSF in patient with nummular eczema.

FIG. 27 is a diagram showing eczema area and severity index (EASI) scores, which measure erythema, edema/tubercles/papules, abrasion, and lichenification in patients with lichen simplex chronicus, nummular eczema, eczema, atopic dermatitis, and dermatitis applied with VSF, and psoriasis area severity index (PASI) scores, which measure erythema, thickness, and scaling in patients with psoriasis.

FIG. 28 is a diagram showing visual analogue scale (VAS) in patients with lichen simplex chronicus, nummular eczema, eczema, atopic dermatitis, dermatitis, and psoriasis applied with VSF.

DETAILED DESCRIPTION OF PREFERRED EMBODIMENTS

The specific details of the present invention may be explained as follows. Meanwhile, the explanations and embodiments disclosed in the present invention may be applied to other explanations and embodiments, respectively. That is, all combinations of various elements disclosed herein belong to the scope of the present invention. Additionally, the scope of the present invention should not be limited by the specific descriptions described herein below.

In order to achieve the objects above, an aspect of the present invention provides a pharmaceutical composition for preventing or treating skin diseases, including, as an active ingredient, a material which specifically binds to a vimentin-derived peptide.

More specifically, the present invention provides a pharmaceutical composition for preventing or treating skin diseases, including, as an active ingredient, a material which specifically binds to a peptide of SEQ ID NO: 1.

As used herein, vimentin, which is a protein encoded by the VIM gene, serves the function of supporting and anchoring intracellular organelles in place, and is known to be mainly involved in maintenance of cytoskeleton, transport of proteins, and cell signaling. In the present invention, it was confirmed that although vimentin is not expressed extracellularly in normal cells, it is expressed extracellularly in the skin tissues of patients with various skin diseases, of which the specific etiology has not yet been clarified, and additionally, when a material that can bind to a vimentin-derived peptide, such as an antibody specific thereto, was applied to the skin tissues of the patients, various skin diseases can be effectively treated.

Specifically, the vimentin-derived peptide may be a peptide of SEQ ID NO: 1.

In the present invention, "the material which specifically binds to a vimentin-derived peptide", which is a material having a binding affinity to the vimentin-derived peptide, may specifically be a material which specifically binds to the peptide of SEQ ID NO: 1.

In the present invention, the isolated peptide of SEQ ID NO: 1 corresponds to the amino acid sequence of vimentin at amino acid positions 142 to 294, and the peptide may include not only the above amino acid sequence but also any amino acid sequence having a homology of 80% or higher, preferably 90% or higher, more preferably 95% or higher, and even more preferably 97% or higher to the above sequence, as long as the antibody of the present invention or a fragment thereof can bind thereto.

More specifically, the material which specifically binds to the peptide of SEQ ID NO: 1 may be an antibody which specifically binds to the peptide of SEQ ID NO: 1 or a fragment binding to the peptide, a compound, a peptide, or an aptamer of the peptide. More specifically, the material may be an antibody which specifically binds to the peptide of SEQ ID NO: 1 or a fragment binding to the peptide, but is not limited thereto.

Specifically, the present invention provides a pharmaceutical composition for preventing or treating skin diseases, including, as an active ingredient, an antibody which specifically binds to the peptide of SEQ ID NO: 1 or a fragment binding to the peptide.

Examples of the antibody may include mouse antibodies, chimeric antibodies, or humanized antibodies, but are not limited thereto.

The humanized antibody or a fragment binding to the peptide of the present invention has superiority in inhibiting human anti-mouse antibody (HAMA) reaction in the human body while maintaining the original affinity and specificity of mouse antibody by transplanting the complementarity-determining region of the variable region of a mouse monoclone or monoclonal antibody, which directly binds to an antigen, to a human antibody backbone. Additionally, the humanized antibodies of the present invention have immunogenicity lowered by de-immunization, and thus can be used as a safe agent when administered to humans by significantly lowering the immunogenicity. That is, the humanized antibodies of the present invention can treat target cells more efficiently by favorably interacting with the human immune system while responding to and influencing the cells in which the peptide region of SEQ ID NO: 1 is exposed to the outside of cell membrane, for example, preventing complement-dependent cytotoxicity (CDC) or antibody-dependent cell-mediated cytotoxicity (ADCC). Additionally, the humanized antibodies of the present invention have an advantage in that the human immune system does not recognize the humanized antibodies as proteins of foreign origin due to the lowered immunogenicity. Additionally, the humanized antibodies of the present invention also have an advantage in that the half-lives of the humanized antibodies in the human circulatory system are similar to those of naturally occurring antibodies, even when the drug is administered in a smaller dose and less frequently.

In the present invention, the mouse antibodies which specifically bind to the isolated peptide of SEQ ID NO: 1 may be collectively referred to as "mouse virus suppressing factor (mVSF)"; chimeric antibodies as "chimeric virus suppressing factor (chVSF)"; and humanized antibodies as "humanized virus suppressing factor (hzVSF)". As used herein, the term "humanized antibody hzVSF" or "variants thereof" can be used interchangeably, and hzVSF can be used interchangeably with the wild-type hzVSF (hzVSF_wt) and a variant of hzVSF (e.g., indicated as hzVSF_var1, hzVSF_v1, hzVSF_1, etc.).

The isolated peptide of SEQ ID NO: 1 is an antigenic region including an epitope, and it may be an amino acid sequence of vimentin at amino acid positions 142 to 211 or at amino acid positions 211 to 294, as long as the peptide can exhibit a function similar to that of the present invention, by binding to an antibody or a peptide-binding fragment. Additionally, it is obvious that any amino acid sequence having such homology described above can belong to the scope of the present invention, although the sequence may have deletion, modification, substitution, or addition in part of the sequence. Vimentin, which is a protein encoded by the VIM gene, serves the functions of supporting and anchoring intracellular organelles in place, and is known to be mainly involved in maintenance of cytoskeleton, transport of proteins, and cell signaling. Vimentin is also known to be used as a cancer marker, however, it is not known whether antibodies capable of binding to vimentin can be used for treatment of skin diseases.

The antibody, which specifically binds to the isolated peptide of SEQ ID NO: 1 of the present invention or a fragment binding to the peptide specifically responds to skin cells of patients having skin diseases, and the antibody or a fragment binding to the peptide binds to the receptors of virus-suppressing factor (VSF) which are exposed to the cell surface in the skin tissue or skin cells of the area affected with the diseases. The antibody or a fragment binding to the peptide of the present invention can thus be used effectively in the field of prevention or treatment of various skin diseases, of which the specific etiology has not yet been clarified.

Specifically, the antibody or a fragment binding to the peptide may be one which specifically binds to the amino acid residue at the $9^{th}$, the $45^{th}$, the $54^{th}$, the $76^{th}$, the $94^{th}$, or the $129^{th}$ position of the peptide of SEQ ID NO: 1, and more specifically, one which specifically binds to the amino acid residue at the $9^{th}$, the $45^{th}$, the $54^{th}$, the $76^{th}$, the $94^{th}$, and the $129^{th}$ positions of the peptide of SEQ ID NO: 1, but is not limited thereto as long as it can specifically bind to the isolated peptide of SEQ ID NO: 1.

As used herein, the term "antibody" immunologically refers to a protein molecule which has the role of a ligand specifically recognizing an antigen, including an immunoglobulin molecule having reactivity to a specific antigen, and it may include all of a polyclonal antibody, a monoclonal antibody, a whole antibody, and an antibody fragment. Additionally, the term "antibody" may include a chimeric antibody (e.g., a humanized murine antibody), a bivalent or bispecific molecule (e.g., a bispecific antibody), a diabody, a triabody, and a tetrabody. Additionally, the term "antibody" may include a single-chain antibody having binding affinity to FcRn, scAb, a derivative of a constant region of an antibody, and an artificial antibody based on a protein scaffold. A whole antibody has a structure consisting of two full-length light chains and two full-length heavy chains, where each light chain is linked to a heavy chain by a disulfide bond. The whole antibody includes IgA, IgD, IgE, IgM, and IgG, and the subtypes of IgG include IgG1, IgG2, IgG3, and IgG4. As used herein, the terms "fragment", "fragment binding to a peptide", and "antibody fragment" refer to any fragment of the antibodies of the present invention having an antigen-binding activity of the antibodies and these terms may be used interchangeably. Examples of the antibody fragment include a single-chain antibody, Fd, Fab, Fab', F(ab')2, dsFv, or scFv, but is not limited thereto. The Fd refers to a heavy chain part included in the Fab fragment. The Fab has a structure consisting of variable regions of the heavy chain and the light chain, constant regions of the light chain, and the first constant region of the heavy chain (CH1 domain), and has a single antigen-binding domain. Fab' differs from Fab in that Fab' has a hinge region containing at least one cysteine residue at the C-terminus of the heavy chain CH1 domain. The F(ab')2 antibody is produced when the cysteine residues in the hinge region of Fab' form a disulfide bond. As used herein, the term "variable fragment (Fv)" refers to a minimum antibody fragment having only the variable region of a heavy chain and the variable region of a light chain. Disulfide-stabilized Fv (dsFv) is characterized in that the variable region of a heavy chain and the variable region of a light chain are linked by a. disulfide bond, and single-chain Fv (scFv) is characterized in that the variable region of a heavy chain and the variable region of a light chain are generally linked by a covalent bond through a linker. These antibody fragments may be obtained using a protease (for example, papain restriction cleavage of the whole antibody can yield Fab, while pepsin cleavage of the whole antibody can yield F(ab')$_2$ fragments), and may preferably be prepared using genetic recombinant technology.

Specifically, the fragment binding to the peptide may be Fab, Fab', F(ab')$_2$, scFv, dsFv, ds-scFv, dimers thereof, minibodies, diabodies, multimers, or bispecific antibody fragments.

As used herein, the term "monoclonal antibody" refers to an antibody molecule consisting of a single molecule obtained from substantially the same antibody group, and the monoclonal antibody exhibits a single binding specificity and affinity to a particular epitope.

Typically, immunoglobulins have heavy chains and light chains, and each of the heavy chains and light chains includes a constant region and a variable region (also known as a domain). The variable regions of the light chain and the heavy chain include three highly variable regions, which are called complementarity-determining regions (hereinafter, "CDR"), and four framework regions (hereinafter, "FR"). The CDR mainly has a role of binding to the epitope of an antigen. The CDR in each chain is called CDR1, CDR2, and CDR3 in sequence, typically starting from the N-terminus, and these are identified by the chain in which a particular CDR is located.

Additionally, when the antibody of the present invention includes a constant region, a constant region derived from IgG, IgA, IgD, IgE, and IgM, or a combination thereof or a hybrid thereof may be included.

As used herein, the term "combination" refers to the formation of a binding between a polypeptide encoding a single-chain immunoglobulin constant region of the same origin and a single-chain polypeptide of a different origin when forming a dimer or multimer. For example, a dimer or multimer may be formed from two or more constant regions selected from the group consisting of the constant regions of IgG, IgA, IgD, IgE, and IgM.

As used herein, the term "hybrid" refers to the presence of sequences corresponding to two or more immunoglobulin heavy chain constant regions of different origins within a single-chain immunoglobulin heavy chain constant region, and for example, a hybrid consisting of one to four domains selected from the group consisting of the CH1, CH2, CH3, and CH4 of IgG, IgA, IgD, IgE, and IgM may be possible.

The humanized antibody of the present invention may be humanized based on human immunoglobulin γ4, although humanization is not limited thereto, and it may have an advantage in that it does not cause CDC due to lack of complement binding.

The humanized antibody or a fragment binding to the peptide may include: a heavy chain variable region including a heavy chain CDR1 of SEQ ID NO: 2; a heavy chain CDR2 of SEQ ID NO: 3 or SEQ ID NO: 14 (in which threonine, the 9$^{th}$ amino acid of SEQ ID NO: 3, is substituted with aspartic acid); and a heavy chain CDR3 of SEQ ID NO: 4 or SEQ ID NO: 15 (in which threonine, the 4$^{th}$ amino acid of SEQ ID NO: 4, is substituted with asparagine); and a light chain variable region including a light chain CDR1 of SEQ ID NO: 5; a light chain CDR2 of SEQ ID NO: 6, SEQ ID NO: 16 (in which threonine, the 3$^{rd}$ amino acid of SEQ ID NO: 6, is substituted with aspartic acid), SEQ ID NO: 17 (in which threonine, the 3$^{rd}$ amino acid of SEQ ID NO: 6, is substituted with aspartic acid; and alanine, the 6$^{th}$ amino acid of SEQ ID NO: 6, is substituted with glycine), or SEQ ID NO: 18 (in which threonine, the 3$^{rd}$ amino acid of SEQ ID NO: 6, is substituted with aspartic acid; leucine, the 5$^{th}$ amino acid of SEQ ID NO: 6, is substituted with arginine; and alanine, the 6$^{th}$ amino acid of SEQ ID NO: 6, is substituted with glycine); and a light chain CDR3 of SEQ ID NO: 7 or SEQ ID NO: 19 (in which serine, the 6$^{th}$ amino acid of SEQ ID NO: 7, is substituted with threonine).

Additionally, the humanized antibody or a fragment binding to the peptide may include a human framework region (FR), and may be human immunoglobulin gamma of SEQ ID NO: 29, SEQ ID NO: 30, and SEQ ID NO: 31, or a heavy chain variable region, which includes a heavy chain framework region 1 (FR1) of SEQ ID NO: 20, a heavy chain FR2 of SEQ ID NO: 21, a heavy chain FR3 of SEQ ID NO: 22 or SEQ ID NO: 28 (in which lysine, the 8$^{th}$ amino acid of SEQ ID NO: 22, is substituted with threonine; and isoleucine, the 10$^{th}$ amino acid of SEQ ID NO: 22, is substituted with alanine), and a heavy chain FR4 of SEQ ID NO: 23; and a light chain variable region, which includes a light chain FR1 of SEQ ID NO: 24, a light chain FR2 of SEQ ID NO: 25, a light chain FR3 of SEQ ID NO: 26, and a light chain FR4 of SEQ ID NO: 27, but is not limited thereto.

Specifically, the humanized antibody or a fragment binding to the peptide may include: (a) a heavy chain CDR1, a heavy chain CDR2, and a heavy chain CDR3 of SEQ ID NO: 2, SEQ NO: 3, and SEQ ID NO: 4, respectively; and a light chain CDR1, a light chain CDR2, and a light chain CDR3 of SEQ ID NO: 5, SEQ ID NO: 6, and SEQ ID NO: 7, respectively; (b) a heavy chain CDR1, a heavy chain CDR2, and a heavy chain CDR3 of SEQ ID NO: 2, SEQ ID NO: 3, and SEQ ID NO: 4, respectively; and a light chain CDR1, a light chain CDR2, and a light chain CDR3 of SEQ ID NO: 5, SEQ ID NO: 16, and SEQ ID NO: 7, respectively; (c) a heavy chain CDR1, a heavy chain CDR2, and a heavy chain CDR3 of SEQ ID NO: 2, SEQ ID NO: 3, and SEQ ID NO: 4, respectively; and a light chain CDR1, a light chain CDR2, and a light chain CDR3 of SEQ ID NO: 5, SEQ ID NO: 17, and SEQ ID NO: 7, respectively; (d) a heavy chain CDR1, a heavy chain CDR2, and a heavy chain CDR3 of SEQ ID NO: 2, SEQ ID NO: 3, and SEQ ID NO: 4, respectively; and a light chain CDR1, a light chain CDR2, and a light chain CDR3 of SEQ NO: 5, SEQ M NO: 18, and SEQ NO: 7, respectively; (e) a heavy chain CDR1, a heavy chain CDR2, and a heavy chain CDR3 of SEQ NO: 2, SEQ ID NO: 3, and SEQ ID NO: 4, respectively; and a light chain CDR1, a light chain CDR2, and a light chain CDR3 of SEQ ID NO: 5, SEQ ID NO: 18, and SEQ ID NO: 19, respectively; (f) a heavy chain CDR1, a heavy chain CDR2, and a heavy chain CDR3 of SEQ NO: 2, SEQ ID NO: 14, and SEQ ID NO: 4, respectively; and a light chain CDR1, a light chain CDR2, and a light chain CDR3 of SEQ ID NO: 5, SEQ ID NO: 6, and SEQ ID NO: 7, respectively; (g) a heavy chain CDR1, a heavy chain CDR2, and a heavy chain CDR3 of SEQ NO: 2, SEQ ID NO: 3, and. SEQ ID NO: 4, respectively; heavy chains FR1, FR2, FR3, and FR4 of SEQ ID NO: 20, SEQ ID NO: 21, SEQ ID NO: 28, and SEQ ID NO: 23, respectively; a light chain CDR1, a light chain CDR2, and a light chain CDR3 of SEQ ID NO: 5, SEQ ID NO: 6, and SEQ NO: 7, respectively; and light chains FR1, FR2, FR3, and FR4 of SEQ ID NO: 24, SEQ ID NO: 25, SEQ ID NO: 26, and SEQ ID NO: 27, respectively; (h) a heavy chain CDR1, a heavy chain CDR2, and a heavy chain CDR3 of SEQ ID NO: 2, SEQ ID NO: 14, and SEQ ID NO: 4, respectively; heavy chains FR1, FR2, FR3, and FR4 of SEQ ID NO: 20, SEQ ID NO: 21, SEQ ID NO: 28, and SEQ ID NO: 23, respectively; a light chain CDR1, a light chain CDR2, and a light chain CDR3 of SEQ ID NO: 5, SEQ ID NO: 6, and SEQ ID NO: 7, respectively; and light chains FR1, FR2, FR3, and FR4 of SEQ ID NO: 24, SEQ ID NO: 25, SEQ ID NO: 26, and SEQ ID NO: 27, respectively; (i) a heavy chain CDR1, a heavy chain CDR2, and a heavy chain CDR3 of SEQ ID NO: 2, SEQ ID NO: 14, and SEQ ID NO: 15, respectively; heavy chains FR1, FR2, FR3, and FR4 of SEQ ID NO: 20, SEQ ID NO: 21, SEQ ID NO: 28, and SEQ ID NO: 23, respectively; a light chain CDR1, a light chain CDR2, and a light chain CDR3 of SEQ ID NO: 5, SEQ NO: 6, and SEQ NO: 7, respectively; and light chains FR1, FR2, FR3, and FR4 of SEQ ID NO: 24, SEQ ID NO: 25, SEQ ID NO: 26, and SEQ ID NO: 27, respectively; (j) a heavy chain CDR1, a heavy chain CDR2, and a heavy chain CDR3 of SEQ ID NO: 2, SEQ ID NO: 14, and SEQ ID NO: 4, respectively; heavy chains FR1, FR2, FR3, and FR4 of SEQ ID NO: 20, SEQ ID NO: 21, SEQ ID NO: 28, and SEQ ID NO: 23, respectively; a light chain CDR1, a light chain CDR2, and a light chain CDR3 of SEQ ID NO: 5, SEQ ID NO: 18, and SEQ ID NO: 7, respectively; and light chains FR1, FR2, FR3, and FR4 of SEQ ID NO: 24, SEQ ID NO: 25, SEQ ID NO: 26, and SEQ ID NO: 27, respectively; (k) a heavy chain CDR1, a heavy chain CDR2, and a heavy chain CDR3 of SEQ ID NO: 2, SEQ ID NO: 14, and SEQ ID NO: 15, respectively; heavy chains FR1, FR2, FR3, and FR4 of SEQ ID NO: 20, SEQ ID NO: 21, SEQ ID NO: 28, and SEQ NO: 23, respectively; a light chain CDRI, a light chain CDR2, and a light chain CDR3 of SEQ ID NO: 5, SEQ ID NO: 18, and SEQ ID NO: 7, respectively; and light chains FR1, FR2, FR3, and FR4 of SEQ ID NO: 24, SEQ ID NO: 25, SEQ ID NO: 26, and SEQ ID NO: 27, respectively; (I) a heavy chain CDRI, a heavy chain CDR2, and a heavy chain CDR3 of SEQ ID NO: 2, SEQ ID NO: 14, and SEQ ID NO: 4, respectively; heavy chains FR1, FR2, FR3, and FR4 of SEQ ID NO: 20, SEQ ID NO: 21, SEQ ID NO: 28, and SEQ ID NO: 23, respectively; a light chain CDR1, a light chain CDR2, and a light chain CDR3 of SEQ ID NO: 5, SEQ ID NO: 18, and SEQ ID NO: 19, respectively; and light chains FR1, FR2, FR3, and FR4 of SEQ ID NO: 24, SEQ ID NO: 25, SEQ ID NO: 26, and SEQ ID NO: 27, respectively; (m) a heavy chain CDR1, a heavy chain CDR2, and a heavy chain CDR3 of SEQ ID NO: 2, SEQ ID NO: 14, and SEQ ID NO: 15, respectively; heavy chains FR1, FR2, FR3, and FR4 of SEQ ID NO: 20, SEQ ID NO: 21, SEQ ID NO: 28, and SEQ ID NO: 23, respectively; a light chain CDR1, a light chain CDR2, and a light chain CDR3 of SEQ ID NO: 5, SEQ ID NO: 18, and SEQ ID NO: 19, respectively; and light chains FR1, FR2, FR3, and FR4 of SEQ ID NO: 24, SEQ ID NO: 25, SEQ ID NO: 26, and SEQ ID NO: 27, respectively; and (n) a heavy chain CDR1, a heavy chain CDR2, and a heavy chain CDR3 of SEQ ID NO: 2, SEQ ID NO: 14, and SEQ ID NO: 4, respectively; and a light chain CDR1, a light chain CDR2, and a light chain CDR3 of SEQ ID NO: 5, SEQ ID NO: 16, and SEQ ID NO: 7, respectively.

The antibody (a) may include hzVSF_WT, antibody (b) may include hzVSF_var1, antibody (c) may include hzVSF_var2, antibody (d) may include hzVSF_var3, antibody (e) may include hzVSF_var4, antibody (f) may include hzVSF_var5, antibody (g) may include hzVSF_var6, antibody (h) may include hzVSF_var7, antibody (i) may include hzVSF_var8, antibody (j) may include hzVSF_var9, antibody (k) may include hzVSF_var10, antibody (l) may include hzVSF_var11, antibody (m) may include hzVSF_var12, and antibody (n) may include hzVSV_var13.

The humanized antibody or a fragment binding to the peptide may include a heavy chain variable region and a light chain variable region of SEQ ID NO: 10 and SEQ ID NO: 12; SEQ ID NO: 32 and SEQ ID NO: 34; SEQ ID NO: 36 and SEQ ID NO: 38; SEQ ID NO: 40 and SEQ ID NO: 42; SEQ ID NO: 44 and SEQ ID NO: 46; SEQ ID NO: 48 and SEQ ID NO: 50; SEQ ID NO: 52 and SEQ ID NO: 54; SEQ ID NO: 56 and SEQ ID NO: 58; SEQ ID NO: 60 and SEQ ID NO: 62; SEQ ID NO: 64 and SEQ ID NO: 66; SEQ ID NO: 68 and SEQ ID NO: 70; SEQ ID NO: 72 and SEQ ID NO: 74; SEQ ID NO: 76 and SEQ ID NO: 78; or SEQ ID NO: 80 and SEQ ID NO: 82, respectively, but is not limited thereto.

Specifically, the mouse antibody may include a heavy chain variable region including a heavy chain CDR1 of SEQ ID NO: 137; a heavy chain CDR2 of SEQ ID NO: 138; and a heavy chain CDR3 of SEQ ID NO: 139; and a light chain variable region including a light chain CDR1 of SEQ ID NO: 134; a light chain CDR2 of SEQ ID NO: 135; and a light chain CDR3 of SEQ ID NO: 136, and more specifically, include a heavy chain variable region of SEQ ID NO: 9 and a. light chain variable region of SEQ ID NO: 8, but is not limited thereto.

Specifically, the chimeric antibody may include a heavy chain variable region of SEQ ID NO: 141 or SEQ ID NO: 142 and a light chain variable region of SEQ ID NO: 140, and more specifically, a heavy chain of SEQ ID NO: 146 or SEQ ID NO: 148 and a light chain of SEQ ID NO: 144, but is not limited thereto.

The scFv may also include a scFv prepared for the safety of mVSF, but is not limited thereto, and for example, the scFv may be prepared by the sequence shown in FIG. 4. Additionally, the scFv may be in the form where the heavy chain variable region of SEQ ID NO: 131 and the light chain variable region of SEQ ID NO: 133 are linked by a linker. Additionally, the scFv may be in the form where the heavy chain variable region encoding the nucleotide sequence of SEQ ID NO: 130 and the light chain variable region encoding the nucleotide sequence of SEQ ID NO: 132 are linked by a linker. Such scFv may be cloned into an *E. coli* expression vector with a nucleotide sequence of SEQ ID NO: 150.

According to a specific embodiment of the present invention, the present inventors prepared humanized antibodies, i.e., hzVSF_wt, three alternatives, and 13 variants thereof (Example 5). Additionally, as a result of comparing the immunogenicity of the humanized antibodies with commercially available drugs which have received FDA approval, it was confirmed that the immunogenicity of the humanized antibodies was similar to that of Humira, which is the human antibody having the lowest immunogenicity among the commercially available antibodies (Table 7), thus confirming that the humanized antibodies can be used as safe drugs, quasi-drugs, external skin preparations, etc., without any adverse effects that may occur when used as therapeutic agents for skin diseases.

Additionally, the T cells analysis revealed that hzVSF_wt variants do not significantly affect T cell proliferation (Table 8), and thus it was confirmed that they have a low risk of causing adverse reactions by acting as immunogens when used in clinical trials.

In the present invention, the skin disease may be pityriasis rosea, herpes zoster, lichen simplex chronicus, herpes simplex, nummular eczema, eczema, molluscum contagiosum, psoriasis, verruca vulgaris, atopic dermatitis or allergic contact dermatitis, and specifically, the skin disease may be lichen simplex chronicus, psoriasis, nummular eczema, eczema, atopic dermatitis or allergic contact dermatitis. However, the skin disease of the present invention may include any skin disease as long as VR is expressed in the skin tissue or skin cells thereof.

In a specific embodiment of the present invention, it was confirmed that the vimentin-derived peptide of SEQ ID NO: 1 was expressed in the skin tissues of patients having various skin diseases, however, the peptide was not expressed in normal cell (FIG. 17). Additionally, it was confirmed that the material which specifically binds to the peptide of SEQ ID NO: 1 substantially showed excellent therapeutic efficacy for skin diseases even in patients with lichen simplex chronicus, nummular eczema, eczema, atopic dermatitis or allergic contact dermatitis (FIGS. 21 to 28), and thus can be used as a pharmaceutical composition for preventing and treating various skin diseases, of which the specific etiology has not yet been clarified.

The pharmaceutical composition may further include a pharmaceutically acceptable carrier.

As used herein, the term "pharmaceutically acceptable carrier" refers to a carrier or diluent which does not inhibit the biological activities or properties of a compound to be administered to an organism without causing irritation to the organism. Examples of the pharmaceutically acceptable carrier used in the composition to be formulated into a liquid solution include saline, sterile water, Ringer's solution, buffered saline, an albumin injection solution, a dextrose solution, a maltodextrin solution, glycerol, ethanol, and a mixture of at least one component thereof, as those suitable for sterilization and in vivo use, and other conventional additive(s) such as an antioxidant, a buffer, a bacteriostatic agent, etc. may be further added as necessary. Additionally, the composition may be formulated into injection formulations such as an aqueous solution, a suspension, an emulsion, etc., pills, capsules, granules, or tablets by additionally adding a diluent, a dispersant, a surfactant, a binder, a lubricant, etc.

The pharmaceutical composition may be prepared in various oral or parenteral formulations. For the preparation of these formulations, the pharmaceutical composition may be formulated in combination with a commonly-used diluent or excipient such as a filler, an extender, a binder, a humectant, a disintegrating agent, a surfactant, etc. Solid formulations for oral administration may include tablets, pills, powders, granules, capsules, etc., and these solid formulations may be prepared by mixing at least one excipient, e.g., starch, calcium carbonate, sucrose or lactose, gelatin, etc. In addition to a simple excipient, a lubricant such as magnesium stearate, talc, etc. may be used. Liquid formulations for oral administration may include suspensions, oral solutions, emulsions, syrups, etc., and in addition to a simple diluent such as water or liquid paraffin, various excipients such as humectants, sweeteners, flavoring agents, preservatives, etc. may be included in the liquid preparations. Formulations for parenteral administration may include sterile aqueous solutions, non-aqueous solvents, suspensions, emulsions, lyophilized formlations, suppositories. Examples of the non-aqueous solvents and suspensions may include propylene glycol, polyethylene glycol, vegetable oils such as olive oil, an injectable ester such as ethyl oleate, etc. Examples of the bases for suppositories may include Witepsol, macrogol, Tween 61, cacao butter, laurinum, glycerogelatin, etc.

The pharmaceutical composition may have any formulation type selected from the group consisting of tablets, pills, powders, granules, capsules, suspensions, oral solutions, emulsions, syrups, sterile aqueous solutions, non-aqueous solvents, suspensions, lyophilized formulations, and suppositories.

The composition of the present invention is administered in a pharmaceutically effective dose.

As used herein, the term "pharmaceutically effective dose" refers to an amount sufficient for the treatment of diseases at a reasonable benefit/risk ratio applicable to a medical treatment, and the level of the effective dose may be determined based on the factors including the kind of a subject, severity of illness, age, sex, kind of disease(s), drug activity, drug sensitivity, administration time, administration route and dissolution rate, duration of treatment, factors including drug(s) to be simultaneously used in combination, and other factors well-known in the medical field. The composition of the present invention may be administered as an individual therapeutic agent, in combination with other therapeutic agent(s), and sequentially or simultaneously with a conventional therapeutic agent(s). Additionally, the composition of the present invention may be administered in a single dose or multiple doses. It is important to administer an amount to obtain the maximum effect with a minimum amount without adverse effects considering the factors described above, and these factors can easily be determined by one of ordinary skill in the art. The other therapeutic agent may be interferon but is not limited thereto.

As used herein, the term "prevention" may refer to all actions resulting in suppression or delay of the onset of a disease by the administration of the composition, and the term "treatment" may refer to all actions associated with the amelioration or advantageous changes in symptoms of a disease by the administration of the composition.

Another aspect of the present invention provides a cosmetic composition for preventing or ameliorating skin diseases, including, as an active ingredient, a material which specifically binds to a peptide of SEQ ID NO: 1.

More specifically, the present invention provides a cosmetic composition tier preventing or ameliorating skin diseases, including, as an active ingredient, an antibody which specifically binds to a peptide of SEQ ID NO: 1 or a fragment binding to the peptide.

The material which specifically binds to the peptide of SEQ ID NO: 1, the peptide of SEQ ID NO: 1, the antibody, the fragment binding to the peptide, the skin disease, and the prevention are as described above.

In a specific embodiment of the present invention, it was confirmed that the material which specifically binds to the peptide of SEQ ID NO: 1 substantially showed excellent therapeutic efficacy even in patients with psoriasis, lichen simplex chronicus, nummular eczema, eczema, atopic dermatitis or allergic contact dermatitis (FIGS. 21 to 28), and thus can be used as a cosmetic composition for preventing and ameliorating various skin diseases, of which the specific etiology has not yet been clarified.

The cosmetic composition according to the present invention may be prepared in formulations selected from the group consisting of solution, topical ointment, cream, foam, nutritive cosmetic water, softening cosmetic water, pack, softening water, latex, makeup base, essence, soap, liquid washing agent, bath foam, sunscreen cream, sun oil, suspension, emulsion, paste, gel, lotion, powder, surfactant-containing cleanser, oil, powder foundation, emulsion foundation, wax foundation, patch and spray, but is not limited thereto.

Additionally, the cosmetic composition of the present invention may further include at least one cosmetically acceptable carrier mixed to a general skin cosmetic composition. As common ingredients, for example, oil, water, surfactants, moisturizers, lower alcohols, thickening agents, chelating agents, colorings, preservatives, fragrances, etc. may be appropriately mixed, but are not limited thereto.

The cosmetically acceptable carrier contained in the cosmetic composition of the present invention may vary depending on the formulations.

When the formulation of the present invention is an ointment, paste, cream or gel, animal oil, vegetable oil, wax, paraffin, starch, tragacanth, cellulose derivatives, polyethylene glycol, silicone, bentonite, silica, talc, zinc oxide, or mixtures thereof may be used as a carrier ingredient.

When the formulation of the present invention is a powder or spray, lactose, talc, silica, aluminum hydroxide, calcium silicate, polyamide powder or mixtures thereof may be used as a carrier ingredient, and in particular, when it is a spray, a propellant such as chlorofluorohydrocarbon, propane/butane or dimethyl ether may be additionally included.

When the formulation of the present invention is a solution or emulsion, solvents, solubilizing agents or emulsifying agents may be used as a carrier ingredient, and for example, water, ethanol, isopropanol, ethyl carbonate, ethyl acetate, benzyl alcohol, benzyl benzoate, propylene glycol, 1,3-buthylglycol oil may be used. In particular, cottonseed oil, peanut oil, maize germ oil, olive oil, castor oil and sesame seed oil, glycerol aliphatic ester, polyethylene glycol or aliphatic ester of sorbitan may be used.

When the formulation of the present invention is a suspension, liquid diluents such as water, ethanol or propylene glycol, suspending agent, such as ethoxylated isostearyl alcohol, polyoxyethylene sorbitol ester and polyoxyethylene sorbitan ester, microcrystalline cellulose, aluminum metahydroxide, bentonite, agar, or tragacanth, etc. may be used as a carrier ingredient.

When the formulation of the present invention is a soap, alkali metal salts of fatty acids, fatty acid hemiester salts, fatty acid protein hydrolysates, isethionate, lanolin derivatives, aliphatic alcohols, vegetable oil, glycerol, sugars, etc. may be used as a carrier ingredient.

Still another aspect of the present invention provides a quasi-drug composition for preventing or ameliorating skin diseases, including, as an active ingredient, a material which specifically binds to a peptide of SEQ ID NO: 1.

More specifically, the present invention provides a quasi-drug composition for preventing or ameliorating skin diseases, including, as an active ingredient, an antibody which specifically binds to a peptide of SEQ ID NO: 1 or a fragment binding to the peptide.

The material which specifically binds to the peptide of SEQ ID NO: 1, the peptide of SEQ ID NO: 1, the antibody, the fragment binding to the peptide, the skin disease, and the prevention are as described above.

The quasi-drug composition of the present invention may further include a pharmaceutically acceptable carrier, excipient or diluent as necessary in addition to the above components. The pharmaceutically acceptable carrier, excipient or diluent is not limited as long as the effect of the present invention is not impaired, and may include, for example, fillers, extenders, binders, wetting agents, disintegrants, surfactants, lubricants, sweeteners, flavoring agents, preservatives, etc.

Examples of the quasi-drug composition of the present invention may include disinfecting cleaners, shower foams, ointments, wet wipes, coating agents, etc., but are not limited thereto. The formulation method, dosage, method of use, components, etc. of the quasi-drug can be suitably selected from conventional techniques known in the art.

Still another aspect of the present invention provides an external skin preparation for preventing or ameliorating skin diseases, including, as an active ingredient, a material which specifically binds to a peptide of SEQ ID NO: 1.

Specifically, the present invention provides an external skin preparation for preventing or ameliorating skin diseases, including, as an active ingredient, an antibody which specifically binds to a peptide of SEQ ID NO: 1 or a fragment binding to the peptide.

The material which specifically binds to the peptide of SEQ ID NO: 1, the peptide of SEQ ID NO: 1, the antibody, the fragment binding to the peptide, the skin disease, and the prevention are as described above.

As used herein, the term "external skin preparation" is a general concept encompassing all substances generally used for external application of the skin. Non-limiting examples of formulations including the pharmaceutical composition may include plasters, lotions, liniments, liquids and solutions, aerosols, extracts, ointments, fluid extracts, emulsions, suspensions, capsules, creams, soft or hard gelatin capsules, patches, or sustained release agents.

The external skin preparation according to the present invention may be a parent era administration preparation formulated into solids, semisolids or liquids by adding a commonly used inorganic or organic carrier, excipient, and diluent. For the parenteral administration, the external skin preparation may be a transdermal administration formulation selected from the group consisting of drops, ointments, lotions, gels, creams, patches, sprays, suspensions and emulsions, but is not limited thereto.

Carriers, excipients, and diluents that may be included in the external skin preparation include lactose, dextrose, sucrose, oligosaccharides, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil.

In the composition for external skin preparation according to each formulation, other components, in addition to the composition of the present invention described above, may be appropriately selected and blended without difficulty by one of ordinary skill in the art according to the formulation or the purpose of use of other external skin preparations, and in this case, a synergistic effect may be achieved when these components are simultaneously applied together with other raw materials.

Still another aspect of the present invention provides a method for preventing or treating skin diseases, including administering a composition including, as an active ingredient, a material which specifically binds to a peptide of SEQ ID NO: 1 to a subject.

Specifically, the present invention provides a method for preventing or treating skin diseases, including administering a composition including, as an active ingredient, an antibody which specifically binds to a peptide of SEQ ID NO: 1 or a fragment binding to the peptide to a subject.

The method for treating skin diseases may be a method including administering a pharmaceutical composition, which includes an antibody or additional pharmaceutically acceptable carrier, to a subject having a skin disease or suspected of having the same. The pharmaceutically acceptable carrier is as described above.

The subject may include mammals, birds, etc., such as cattle, pigs, sheep, chickens, dogs, humans, etc., and may include without limitation any subject in which the skin diseases can be treated by administering the composition of the present invention.

In particular, the composition may be administered in a pharmaceutically acceptable amount in a single or multiple dose. The composition may be administered in the form of liquids, powders, aerosols, capsules, enteric coated tablets, capsules, or suppositories. Examples of the administration routes may include intraperitoneal, intravenous, intramuscular, subcutaneous, endothelial, oral, topical, intranasal, intrapulmonary, or intrarectal administration, etc., but is not limited thereto. However, since peptides are digested when being administered orally, the composition for oral administration must be formulated such that the active ingredient can be coated or protected from degradation in the stomach. Additionally, the pharmaceutical composition may be administered using any device which can transport the active ingredient to the target cell.

Still another aspect of the present invention provides the use of a composition for preventing or treating skin diseases, including, as an active ingredient, a material which specifically binds to a peptide of SEQ NO: 1.

Still another aspect of the present invention provides the use of a composition including, as an active ingredient, a material which specifically binds to a peptide of SEQ ID NO: 1 for the preparation of medicine in the prevention or treatment of skin diseases.

Still another aspect of the present invention provides the use of a composition including, as an active ingredient, a material which specifically binds to a peptide of SEQ ID NO: 1 for the preparation of cosmetics, quasi-drugs, or external skin preparations in the amelioration of skin diseases.

MODE FOR CARRYING OUT THE INVENTION

The present invention will be described in more detail by Examples. However, these Examples are given for illustrative purposes only, and are not intended to limit the scope of the present invention.

EXAMPLE 1

Preparation of Vsf (Virus Suppressing Factor)

EXAMPLE 1-1

Preparation of chVSF (Chimeric VSF)

Based on the assumption that the major functional part of the mouse VSF (mVSF) is a monoclonal antibody, a mouse/human chimeric antibody (chAb) was chimerized by genetic engineering using the mVSF and human immunoglobulin.

Specifically, for the preparation of a chimeric antibody, the constant regions of the light and heavy chains of mVSF were replaced with the constant regions of human immunoglobulin antibody (κ, γ2, or γ4). For chVSF, an expression vector was prepared using the pCAGGS vector as a template (FIG. 1). The heavy chain variable region of mVSF (mVH) (SEQ ID NO: 9) including the SacI and KpnI restriction enzyme sites was amplified by PCR. The light chain variable region (mVL) (SEQ ID NO: 8) including the ClaI and XhoI restriction enzyme sites was amplified by PCR. The primers used in PCR are described in Table 1, and the PCR was performed for a total of 35 cycles at 94° C. for 45 sec, at 60° C. for 45 sec, and at 72° C. for 45 sec, followed by performing at 72° C. for 10 min.

TABLE 1

| Primer | Sequence | Sequence No. |
|---|---|---|
| mVH F | cgagctcatgggatggagctggatc | 124 |
| mVH R | cggtacctgaggagacggtgactg | 125 |
| KpnI_delR | gggcccttggtgaaagctgaggaga cggtaactgagg | 126 |
| mVL F | catcgatatgagtgtgcccactcag | 127 |
| mVL R | cctcgagtttgatttccagcttgg | 128 |
| Xho_modR | agatggtgcagccaccgtgcgtttg atttccagcttggtgcc | 129 |

The human heavy chain (SEQ ID NO: 11) was cloned using the KpnI and SphI restriction enzyme sites, and the light chain (SEQ ID NO: 13) was cloned using the XhoI and BglI restriction enzyme sites. For the simultaneous expression of both heavy and light chains, an internal ribosome entry site (IRES) was cloned between the light chain and the heavy chain using the SphI and ClaI restriction enzyme sites. A selectable marker was inserted into the SalI restriction enzyme site. Accordingly, the chVSFs were prepared as illustrated in the schematic diagram of FIG. 2.

EXAMPLE 1-2

Expression of chVSF Using Two-Vector Expression System

15 μg of pCAGGS-GFP was transfected into HEK 293T cells using 1 mg/mL of polyethylenimine (PEI) to examine the levels of transfection and expression. The chVSF prepared in Example 1-1 was transfected into HEK 293T cells in the same manner, and after 6 hours, the medium was replaced with a medium containing 2% FBS. The cell culture supernatant was collected every 3 days, and impurities contained therein were removed using a filter (0.45 μm). The chVSF was purified using nProtein A Sepharose® beads. The chVSF was eluted with 0.2 M glycine/HCl buffer (pH 2.5), and 1 M Tris-Cl buffer (pH 9.0) was used as a neutralization buffer. Specifically, after homogenizing a resin with a 10-fold volume of 1 M Tris-Cl buffer (pH 8.0) relative to the resin volume, the VSF culture supernatant was passed through a column. The resultant was washed by flowing thereinto an at least 5-fold volume of 0.1 M Tris-Cl butler (pH 8.0) relative to the column volume. The resultant was eluted by flowing thereinto a 5-fold volume of 0.2 M glycine/HCl buffer (pH 2.5) relative to the resin volume, and purified VSFs were thereby obtained in a tube added with a neutralization buffer in advance. The purified VSFs were then confirmed by SDS-PAGE.

As a result, as illustrated in FIG. 3, it was confirmed that the chVSF has a structure consisting of a heavy chain (50 kDa) and a light chain (25 kDa), which have the characteristics of an immunoglobulin.

EXAMPLE 2

Preparation of Single-Chain Variable Fragment (say)

A single-chain variable fragment (scFv) was prepared using the variable regions of VSF. The scFv has the DNA sequence of SECT ID NO: 150, and the scFv was prepared by cloning the DNA into pET-22b (+), an *E. coli* expression vector (FIGS. 4 and 5).

Specifically, the scFV was prepared by linking the VH and VL of mVSF via a linker, inserted into the bacterial expression vector, pET-22b (+), treated with IPTG to induce its expression, and then purified using a Ni-NTA column (FIG. 6).

EXAMPLE 3

Preparation of Humanized Antibody VSF hzVSF, a humanized antibody, was prepared using the chVSF based on Example 1.

In particular, the pdCMV-dhfr vector, which corresponds to a two-gene expression vector, i.e., an expression system used for expressing two different kinds of recombinant proteins using a eukaryotic cell (FIG. 7), was used. The vector consists of two different transcription units for two different kinds of genes in a single vector and thereby expresses the two different genes using the promoter and polyA signal in each transcription unit, and it is a vector system utilizing the cytomegalovirus (CMV) promoter, a strong mammalian promoter. The hzVSFs were prepared using the promoter, as illustrated in FIG. 8.

In this regard, the amino acid sequence of the heavy chain variable region of the hzVSF was indicated by SEQ ID NO: 10, and the amino acid sequence of the heavy chain region was indicated by SEQ ID NO: 11, whereas the amino acid sequence of the light chain variable region was indicated by SEQ ID NO: 12, and the amino acid sequence of the light chain was indicated by SEQ ID NO: 13.

15 μg of pCAGGS-GFP was transfected into HEK 293T cells using 1 mg/mL of polyethylenimine (PEI) to examine the levels of transfection and expression. The chVSF and hzVSF were transfected into HEK 293T cells in the same manner, and after 6 hours, the medium was replaced with a medium containing 2% FBS. The cell culture supernatant was collected every 3 days, and impurities contained therein were removed using a filter (0.45 μm). The chVSF and hzVSF were purified using nProtein A Sepharose® beads. The chVSF and hzVSF were eluted with 0.2 M glycine/HCl buffer (pH 2.5), and 1 M Tris-Cl buffer (pH 9.0) was used as a neutralization buffer. Specifically, after homogenizing a resin with a 10-fold volume of 1 M Tris-Cl buffer (pH 8.0) relative to the resin volume, the VSF culture supernatant was passed through a column. The resultant was washed by flowing thereinto an at least 5-fold volume of 0.1 M Tris-Cl buffer (pH 8.0) relative to the column volume. The resultant was eluted by flowing thereinto a 5-fold volume of 0.2 M glycine/HCl buffer (pH 2.5) relative to the resin volume, and purified VSFs were thereby obtained in a tube added with a neutralization buffer in advance. The purified VSFs were then confirmed by SDS-PAGE, and their activities were confirmed by MVIT assay.

The VSFs used in the experiment are shown in Table 2 below

TABLE 2

| Types of VSF | Expression Cells | mg/L Harvested Sup. |
|---|---|---|
| mVSF | Mouse hybridoma | 4.14 |
| *rmVSF | HEK293T | 5.71 |
| chVSF γ 2 | HEK293T | 5.15 |
| chVSF γ 4 | HEK293T | 7.32 |
| hzVSF γ 2 | HEK293T | 5.01 |
| hzVSF γ 4 | HEK293T | 9.38 |

*rmVSF: recombinant of mouse VSF

As a result, as can be seen in FIG. 9, it was confirmed that the chVSFγ2 and chVSFγ4, and hzVSFγ2 and hzVSFγ4 consist of a heavy chain (50 kDa) and a light chain (25 kDa), respectively, which have the characteristics of an immunoglobulin.

EXAMPLE 4

Confirmation of Physical Properties of Humanized Antibody VSF

The physical properties of the hzVSF prepared in Example 3 were confirmed as follows.

EXAMPLE 4-1

Confirmation of Basic Molecular Weight Patterns and Purity

Molecular weight patterns and purities were confirmed by reducing and non-reducing SDS-PAGE. Specifically, hsVSF_v13 was stained by Coomassie staining using SDS-PAGE according to molecular weight, and thereby the molecular weight and purity were confirmed.

As a result, as illustrated in FIG. 10, in lane 1 as a non-reducing gel, a major band was observed in the position where IgG antibody (150 kDa) was expected to appear; and in lane 2 as a reducing gel, the bands corresponding to the positions of the heavy chain (about 50 kDa) and the light chain (about 25 kDa) of immunoglobulin G (IgG) antibody were observed, thus confirming that the hzVSF_v13 showed a general IgG antibody pattern.

EXAMPLE 4-2

Confirmation of Molecular Weight, Glycosylation Pattern, Size Variation, etc

In order to confirm the molecular weight, glycosylation pattern, size variation, etc., of the hzVSF_v13, liquid chromatography/mass spectrometry was performed. A small amount of the hzVSF_v13 was injected into HPLC, and the peaks were observed.

As a result, it was confirmed that the hzVSF_v13 exhibited the characteristics of IgG (FIG. 11). In Intact Mass, the total molecular weight (about 140 kDa) of the hzVSF_v13 was observed, and the peak patterns corresponding to general glycosylated IgG (e.g., G0/G0, G0F/G1, G1/G1, etc.) were observed. Additionally, the heavy chain (about 49 kDa) and the light chain (about 23 kDa) after deglycosylation were observed. Based on the molecular weights of the heavy chain, where the glycan was removed by treating with PNGase F, and the heavy chain without PNGase F treatment, a general glycan pattern of IgG could be confirmed (G0F, G1F, and G2F).

EXAMPLE 4-3

Confirmation of Purity and Aggregation

In order to confirm the purity and aggregation of the hzVSF_v13, SEC-HPLC was performed.
SEC-HPLC conditions are as follows:
HPLC system: Dionex Ultimate 3000
Column: Tosoh TSKgel G3000 SWx1
Mobile phase: phosphate buffer, 0.5 ml/min
Injection Volume: 10 μL
As a result, 92.44% of the major peak was observed at the position corresponding to the monomers of a typical IgG antibody (at the retention time of about 16 minutes) and about 6.84% of the peak was observed at the position corresponding to the dimers of a typical IgG antibody (at the retention time of about 13 minutes) (FIG. 12).

EXAMPLE 4-4

Confirmation of pI and Charge Heterogeneity

In order to confirm the isoelectric point of the hzVSF_v13, electrophoresis was performed using a gel exhibiting a gradient of pH 3 to pH 10.
As a result, as illustrated in FIG. 13, the hzVSF_v13 was shown to have a pI of 7.7, and acidic/basic isoforms were also observed in addition to the major bands. This corresponds to the isomers generally observed in IgG antibodies (e.g., deamination at the C-terminal region).
The above results support that the hzVSF_v13s, humanized antibodies of the present invention, have physical properties similar to those of IgG antibodies.

EXAMPLE 5

Preparation of hzVSF Variants which are Humanized Antibodies with Reduced Immunogenicity

EXAMPLE 5-1

Preparation of hzVSF Alternatives

Three hzVSF alternatives were prepared based on the hzVSF prepared in Example 3. The activity of each alternative was similar to or lower than that of the wild-type (0.5=≤1 U<1 mg/mL) (Tables 3 and 4). The amino acid sequences of CDR 1 to CDR 3 for each of the alternatives are shown in Table 3, and the amino acid sequences of FR1 to FR4 of each of the variants are shown in Table 4.

TABLE 3

| Antibody | CDR1 | CDR2 | CDR3 |
|---|---|---|---|
| hzVSF_WT | Heavy chain GYNMN (SEQ ID NO: 2) | NIDPYYGSTTYA QKFQG (SEQ ID NO: 3) | ETGTRAMDY (SEQ ID NO: 4) |
| | Light chain RASENTYSNLA (SEQ ID NO: 5) | VATNLAD (SEQ ID NO: 6) | QHFYGSPRT (SEQ ID NO: 7) |

TABLE 3-continued

| Antibody | CDR1 | CDR2 | CDR3 |
|---|---|---|---|
| hzVSf_a1 | Heavy chain GYNMN (SEQ ID NO: 2) | NIDPYYGSTTYA QKFQG (SEQ ID NO: 3) | ETGTRAMDY (SEQ ID NO: 4) |
| | Light chain RASENIYSNL A (SEQ ID NO: 5) | VATNLAD (SEQ ID NO: 6) | QHFYGSPRT (SEQ ID NO: 7) |
| hzVSF_a2 | Heavy chain GYNMN (SEQ ID NO: 2) | NIDPYYGSTINA QKFQG (SEQ ID NO: 3) | ETGTRAMDY (SEQ ID NO: 4) |
| | Light chain RASENIYSNL A (SEQ ID NO: 5) | VATNLAD (SEQ ID NO: 6) | QUIFYGSPRT (SEQ ID NO: 7) |
| hzVSF_a3 | Heavy chain GYNMN (SEQ ID NO: 2) | NIDPYYGSTTYA QKFQG (SEQ ID NO: 3) | ETGTRAMDY (SEQ ID NO: 4) |
| | Light chain RASENIYSNL A (SEQ ID NO: 5) | VATNLAD (SEQ ID NO: 6) | QHFYGSPRT (SEQ ID NO: 7) |

TABLE 4

| Antibody | | FR1 | FR2 | FR3 | FR4 |
|---|---|---|---|---|---|
| hzVSF_WT | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_a1 | Heavy chain | SEQ ID NO: 151 | SEQ ID NO: 21 | SEQ ID NO: 22 | SEQ ID NO:23 |
| | Light chain | SEQ ID NO: 24 | SEQ ID NO: 25 | SEQ ID NO: 26 | SEQ ID NO: 27 |
| hzVSF_a2 | Heavy chain | SEQ ID NO: 20 | SEQ ID NO: 152 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_a3 | Heavy chain | SEQ ID NO: 151 | SEQ ID NO: 152 | SEQ ID NO: 22 | SEQ ID NO: 23 |
| | Light chain | SEQ ID NO: 24 | SEQ ID NO: 25 | SEQ ID NO: 26 | SEQ ID NO: 27 |

EXAMPLE 5-2

Preparation of hzVSF Variants

Based on the hzVSF prepared in Example 3, hzVSF variants for actual use in viva were prepared via immunogenicity reduction and affinity maturation. As a result, a total of 13 variants were prepared (Tables 5 and 6). The amino acid sequences of CDR 1 to CDR 3 for each of the variants are shown in Table 5, and the amino acid sequences of FR1 to FR4 for each of the variants are shown in Table 6.

TABLE 5

| Antibody | | CDR1 | CDR2 | CDR3 |
|---|---|---|---|---|
| hzVSF_var 7 | Heavy chain | GYNMN (SEQ ID NO: 2) | NIDPYYGSDTYAQKFQG (SEQ ID NO: 14) | ETGTRAMDY (SEQ ID NO: 4) |
| | Light chain | RASENIYSNLA (SEQ ID NO: 5) | VATNLAD (SEQ ID NO: 6) | QHFYGSPRT (SEQ ID NO: 7) |
| hzVSF_var 8 | Heavy chain | GYNMN (SEQ ID NO: 2) | NIDPYYGSDTYAQKFQG (SEQ ID NO: 14) | ETGNRAMD (SEQ ID NO: 15) |
| | Light chain | RASENIYSNLA (SEQ ID NO: 5) | VATNLAD (SEQ ID NO: 6) | QHFYGSPRT (SEQ ID NO: 7) |
| hzVSF_var 9 | Heavy chain | GYNMN (SEQ ID NO: 2) | NIDPYYGSDTYAQKFQG (SEQ ID NO: 14) | ETGTRAMDY (SEQ ID NO: 4) |
| | Light chain | RASENIYSNLA (SEQ ID NO: 5) | VADNRGD (SEQ ID NO: 18) | QHFYGSPRT (SEQ ID NO: 7) |
| hzVSF_var 10 | Heavy chain | GYNMN (SEQ ID NO: 2 | NIDPYYGSDTYAQKFQG (SEQ ID NO: 14) | ETGNI ID (SEQ ID NO: 15) |
| | Light chain | RASENIYSNLA (SEQ ID NO: 5) | VADNRGD (SEQ ID NO: 18) | QHFYGSPRT (SEQ ID NO: 7) |
| hzVSF_var 11 | Heavy chain | GYNMN (SEQ ID NO: 2) | NIDPYYGSDTYAQKFQG (SEQ ID NO: 14) | ETGTRAMDY (SEQ ID NO: 4) |
| | Light chain | RASENIYSNLA (SEQ ID NO: 5) | VADNRGD (SEQ ID NO: 18) | QHFYGTPRT (SEQ ID NO: 19) |
| hzVSF_var 12 | Heavy chain | GYNMN SEQ ID NO: 2) | NIDPYYGSDTYAQKFQG (SEQ ID NO: 14) | ETGNRAMD (SEQ ID NO: 15) |
| | Light chain | RASENIYSNLA (SEQ ID NO: 5) | VADNRGD (SEQ ID NO: 18) | QHFYGTPRT (SEQ ID NO: 19) |
| hzVSF_var 13 | Heavy chain | GYNMN SEQ ID NO: 2) | NIDPYYGSDTYAQKFQG (SEQ ID NO: 14) | ETGTRAMDY (SEQ ID NO: 4) |
| | Light chain | RASENIYSNLA (SEQ ID NO: 5) | VADNLAD (SEQ ID NO: 16) | QHFYGSPRT (SEQ ID NO: 7) |

TABLE 6

| Antibody | | FR1 | FR2 | FR3 | FR4 |
|---|---|---|---|---|---|
| hzVSF_WT | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_var1 | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_var2 | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_var3 | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_var4 | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_var5 | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |
| hzVSF_var6 | Heavy chain | SEQ ID NO: 20 | SEQ ID NO: 21 | SEQ ID NO: 28 (K74T, I76A) | SEQ ID NO: 23 |
| | Light chain | SEQ ID NO: 24 | SEQ ID NO: 25 | SEQ ID NO: 26 | SEQ ID NO: 27 |
| hzVSF_var7 | Heavy chain | SEQ ID NO: 20 | SEQ ID NO: 21 | SEQ ID NO: 28 (K74T, I76A) | SEQ ID NO: 23 |
| | Light chain | SEQ ID NO: 24 | SEQ ID NO: 25 | SEQ ID NO: 26 | SEQ ID NO: 27 |
| hzVSF_var8 | Heavy chain | SEQ ID NO: 20 | SEQ ID NO: 21 | SEQ ID NO: 28 (K74T, I76A) | SEQ ID NO: 23 |
| | Light chain | SEQ ID NO: 24 | SEQ ID NO: 25 | SEQ ID NO: 26 | SEQ ID NO: 27 |
| hzVSF_var9 | Heavy chain | SEQ ID NO: 20 | SEQ ID NO: 21 | SEQ ID NO: 28 (K74T, I76A) | SEQ ID NO: 23 |
| | Light chain | SEQ ID NO: 24 | SEQ ID NO: 25 | SEQ ID NO: 26 | SEQ ID NO: 27 |
| hzVSF_var10 | Heavy chain | SEQ ID NO: 20 | SEQ ID NO: 21 | SEQ ID NO: 28 (K74T, I76A) | SEQ ID NO: 23 |
| | Light chain | SEQ ID NO: 24 | SEQ ID NO: 25 | SEQ ID NO: 26 | SEQ ID NO: 27 |
| hzVSF_var11 | Heavy chain | SEQ ID NO: 20 | SEQ ID NO: 21 | SEQ ID NO: 28 (K74T, I76A) | SEQ ID NO: 23 |
| | Light chain | SEQ ID NO: 24 | SEQ ID NO: 25 | SEQ ID NO: 26 | SEQ ID NO: 27 |
| hzVSF_var12 | Heavy chain | SEQ ID NO: 20 | SEQ ID NO: 21 | SEQ ID NO: 28 (K74T, I76A) | SEQ ID NO: 23 |
| | Light chain | SEQ ID NO: 24 | SEQ ID NO: 25 | SEQ ID NO: 26 | SEQ ID NO: 27 |
| hzVSF_var13 | Heavy chain | SEQ ID NO: 20 | SEQ ID NO: 21 | SEQ ID NO: 22 | SEQ ID NO: 23 |
| | Light chain | SEQ ID NO: 24 | SEQ ID NO: 25 | SEQ ID NO: 26 | SEQ ID NO: 27 |

It was confirmed that all of the 13 variants prepared above had reduced immunogenicity compared to those of the wild-type.

EXAMPLE 5-3

Confirmation of Epitope Counts of hzVSF Wild-Type and Variants Thereof

The epitope counts of the hzVSF wild-type; hzVSF_var12 and hzVSF_var13, which are the representative variants among the variants with reduced immunogenicity of the wild-type; and four kinds of blockbuster antibody drugs currently available in the pharmaceutical market were compared. As a result, the possibility of relative immunogenicity in each HLA class II was confirmed, as shown in Table 7.

TABLE 7

| Type of Protein | DRB1 | DRB 3/4/5 | DQ | DP | Total |
|---|---|---|---|---|---|
| hzVSF wt | 31 | 17 | 1 | 3 | 52 |
| hzVSF_var1 | 30 | 18 | 1 | 3 | 52 |
| hzVSF_var2 | 30 | 17 | 0 | 3 | 50 |
| hzVSF_var3 | 30 | 16 | 0 | 3 | 49 |
| hzVSF_var4 | 28 | 16 | 0 | 3 | 47 |
| hzVSF_var5 | 30 | 16 | 1 | 3 | 50 |
| hzVSF_var6 | 29 | 16 | 1 | 3 | 49 |
| hzVSF_var7 | 28 | 15 | 1 | 3 | 47 |
| hzVSF_var8 | 27 | 14 | 1 | 3 | 45 |
| hzVSF_var9 | 27 | 14 | 0 | 3 | 44 |
| hzVSF_var10 | 26 | 13 | 0 | 3 | 42 |
| hzVSF_var11 | 25 | 14 | 0 | 3 | 42 |
| hzVSF_var12 | 24 | 13 | 0 | 3 | 40 |
| hzVSF_var13 | 29 | 17 | 0 | 3 | 49 |
| Humira (human) | 25 | 12 | 4 | 1 | 42 |
| Remicade (chimeric) | 74 | 37 | 3 | 1 | 115 |
| Rituxan (chimeric) | 65 | 33 | 9 | 3 | 110 |
| Herceptin (humanized) | 40 | 20 | 3 | 1 | 64 |

In Table 7, a higher total value means that there is a higher likelihood of adverse effects due to the HLA class II. From the above results, it was confirmed that the epitope counts of the hzVSF_var12 and hzVSF_var13 with reduced immunogenicity of the present invention were similar to that of Humira, which has the lowest epitope count among the four kinds of pharmaceutical drugs. These results suggest that the humanized antibodies of the present invention would have a very low level of serious side effects that may arise, and thus support the safety of the humanized antibodies of the present invention as safe drugs.

EXAMPLE 5-4

Confirmation of T Cell Analysis of hzVSF Variants

In order to evaluate the immunogenicity of the hzVSF_var12 and hzVSF_var13, it was confirmed whether the material examined by in vitro T cell analysis of Lonza can have an effect on T cell proliferation using the blood samples of 51 healthy donors. The total peripheral blood mononuclear cells (PBMC) of each donor were treated with the hzVSF_var12, hzVSF_var13, or Keyhole limpet hemocyanin (KLH) and cultured for 7 days. The KLH is an oxygen-carrying metalloprotein that can be used as a carrier protein in the production of antibodies, and it was used as a positive control for its ability to effectively elicit immune responses. Then, the ratio (%) of T cells stained with $CD3^+CD4^+Edu^+$ was measured. As a result, the KLH showed T cell proliferation in 45 blood donors (a response rate of 88%), whereas the hzVSF_var12 and hzVSF_var13 induced T cell proliferation in only 3 subjects (a response rate of 5.8%), in response to the material (FIG. 14).

Meanwhile, the stimulation index (SI) of T cell proliferation induced by the KLH, hzVSF_v12, or hzVSF_v13 was calculated using the PBMC cultured as a control for 7 days. When the SI value is greater than 2, the immunogenicity is expected to be large when applied to humans. In contrast, when the SI value is less than 0.5, T cell proliferation is expected to be inhibited. As a result, it was confirmed that the hzVSF_v12 and hzVSF_v13 showed low SI values of 1.12 and 1.03, respectively, and also showed SI values in the range of 0.6 or greater and 2 or less. In contrast, the KUL which was used as a positive control, showed a high SI value of 3.91 (FIGS. 15 and 16; and Table 8).

TABLE 8

| Product (Antigen) | Mean SI | p-value |
|---|---|---|
| hzVSF_var12 | 1.12 | 0.008 |
| hzVSF_var13 | 1.05 | 0.3229 |
| KLH | 3.91 | <0.0001 |

From the above results, it is expected that the hzVSF_v12 and hzVSF_v13 would have less immunogenicity when administered to patients having skin diseases and subsequently have few side effects.

EXAMPLE 6

Investigation of Reactivity Between Human Normal Tissues and VSF

Hereinafter, the therapeutic effects of the hzVSF (hereinafter, VSF) prepared and confirmed in Examples 1 to 5 on skin diseases were confirmed in various ways.

First, in order to investigate activity between human normal tissues and VSF, immunohistochemical staining was performed with mVSF using tissue microarray (TMA), a slide in which normal tissues for human major organs were arrayed.

As a result, no staining by mVSF was observed at all in normal tissues (FIG. 17). Therefore, it can be seen that VR, which is a VSF receptor, is not expressed in normal tissues, and VSF will only act on skin cells with skin diseases. Additionally, VSF does not affect normal tissues, and thus it may have excellent pharmacological effects with small side effects, even when used as a pharmaceutical composition, etc.

EXAMPLE 7

Confirmation of VR Expression in Various Skin Diseases

Since it was confirmed in Example 6 that YR was not expressed in normal tissues (normal cells), it was confirmed whether VR was expressed in skin tissues with skin diseases.

First, immunohistochemical staining was performed with mVSF using slides on which skin tissues of patients with various skin diseases were fixed. Specific experimental method of each step is as follows:

EXAMPLE 7-1

Paraffin Embedding

Skin specimens of tissues obtained from patients with skin disease were fixed for 48 hours in 10% neutral buffered formalin (NBF). The fixed solution (10% NBF) was removed from the fixed skin specimens and washed with 1× PBS for 30 minutes using an agitator. After removing 1× PBS, a dehydration process was performed in the agitator using 70%, 90%, and 100% alcohol for 1 hour each. Then, a clearing process was carried out as a pretreatment for 1 hour in a solution of xylene: 100% alcohol (1:1). Subsequently, a clearing process was carried out using xylene for 3 times within 1 hour, and an infiltration process was carried out using paraffin melted at 60° C. for 2 times within 1 hour. Thereafter, an infiltration process was carried out by treating paraffin melted in an oven at 60° C. to the skin specimens for 12 hours. 50% of the paraffin melted at 60° C. was filled into a mold using a paraffin section preparation machine, and then 50% of the melted paraffin was added thereto. The paraffin mold was then dried for 1 hour on a cold pad and 6 hours on an experimental table.

After drying, the mold was removed to obtain a paraffin block, which was refrigerated (4° C.). Specifically, 80% of an ice box was filled with ice, and an appropriate amount of tap water was added to make a cold state, then the refrigerated paraffin block was placed in the ice box in the direction of the specimen. This was because the tissues may crack and suitable tissues may not be obtained, unless the block is kept in a cold state.

Thereafter, the tissues were cut into 4 μm using a tissue cutting machine, and the thus-cut tissues were immersed in 50% alcohol and subsequently placed in a constant temperature bath at 43° C. The cut-skin tissues were attached to the slide. The slide was placed on a heating pad warmed to 43° C., dried for 1 hour, and then refrigerated (4° C.).

EXAMPLE 7-2

Hematoxylin-Eosin Staining (H&E Staining)

The skin specimen slides were allowed to stand in xylene for 10 minutes. The slides were filled with new xylene, and allowed to stand therein for 10 minutes and then in 100% alcohol (1:1) for 3 minutes. Thereafter, deparaffinization was carried out by allowing the slides to stand in 100%, 95%, 90%, 70%, and 50% alcohol for 3 minutes each. After hydrating the slides for 10 minutes under running tap water, the slides were allowed to stand in Harris hematoxylin for 3 minutes to first stain the nuclei. Subsequently, the hydration process was performed for 5 minutes under running tap water.

The slides were bleached by adding 1% hydrochloric acid (a few drops) to remove stained hematoxylin, and were allowed to stand in eosin for 3 minutes to stain surrounding tissues, followed by hydration for 3 minutes under running tap water. Thereafter, the slides were allowed to stand in 70%, 90%, 95%, and 100% alcohol for 3 minutes each and then allowed to stand in xylene for 5 minutes, and encapsulated with an organic solvent encapsulant. The slides were dried in the hood until the smell of xylene disappeared, and the tissues were observed under a microscope.

EXAMPLE 7-3

Immunohistochemistry (IHC) Staining

The skin specimen slides were allowed to stand in xylene for 10 minutes. The slides were filled with new xylene, and allowed to stand therein for 10 minutes, and then in xylene: 100% alcohol (1:1) for 3 minutes. Thereafter, deparaffinization was carried out by allowing the slides to stand in 100%, 95%, 90%, 70%, and 50% alcohol for 3 minutes each.

After hydrating the slides for 10 minutes under running tap water, the slides were allowed to stand in 3% hydrogen peroxide for 5 minutes and washed twice with PBS for 3 minutes each. The slides were added to the retrieval buffer and boiled in a microwave oven (95° C.) for 10 minutes (additional buffer was added when the buffer was boiled away so as to avoid drying of tissues). The buffer was cooled at room temperature for 30 minutes and washed twice with PBS twice for 3 minutes each. 1% bovine serum albumin (BSA) was prepared using 1× TBST (50 mM Tris, 150 mM NaCl, 0.1% Tween 20) and allowed to stand at room temperature for 1 hour. The slides were incubated overnight in a 4° C. constant humidity chamber with mVSF (1:50) and washed 3 times for 10 minutes using 1× TBST. Then, the slides were incubated with horseradish peroxidase (HRP)-conjugated anti-mouse IgG antibody (1:2000) for 30 minutes at room temperature and washed 3 times for 10 minutes using 1× TBST. Subsequently, the slides were allowed to stand in a diaminobenzidine (DAB): hydrogen peroxide (1:20) solution for 5 minutes to detect chromogens, and then allowed to stand in Harris hematoxylin for 30 seconds to stain the nuclei, followed by hydration under running tap water. Finally, the slides were encapsulated using a water-soluble encapsulant.

EXAMPLE 7-4

Confirmation Result of VR Expression in Skin Tissues of Patients with Skin Diseases In the same manner as above, the expression of VR, a receptor of VSF in skin tissues of patients with various skin diseases and a biomarker expressed only in skin cells with skin diseases, were confirmed through immunohistochemical staining.

Specifically, a punch biopsy was performed on the skin tissue of patients with skin diseases to make paraffin blocks by the above method. Accordingly, H&E staining and immunohistochemical staining were performed with mVSF to confirm VR expression.

As a result, as shown in FIGS. 18 to 20, VR was expressed in all skin tissues of 10 patients with pityriasis rosea, and VR was expressed 90% or more in the skin tissues of patients with herpes zoster, lichen simplex chronicus and herpes simplex. Additionally, VR was expressed 67% or more in the skin tissues of patients with circular eczema, molluscum contagiosum, psoriasis, verruca vulgaris, atopic dermatitis and allergic contact dermatitis. Finally, it was confirmed that VR expression was observed in the skin issues of 88 patients with skin diseases (a response rate of 80%) out of 110 patients.

Therefore, VR, which can bind to the VSF, is expressed in the skin tissues of patients with pityriasis rosea, lichen simplex chronicus, nummular eczema, psoriasis, atopic dermatitis, etc., which are skin diseases of which the definite etiology has not yet been clarified. Thus, it can be implied that the treatment effect on the skin diseases can be expected by treatment with VSF.

Accordingly, the therapeutic effect of VSF in patients with skin diseases was examined in more detail.

EXAMPLE 8

Evaluation of Therapeutic Efficacy of VSF in Patients with Skin Diseases

The aim of this Example was to determine the therapeutic effect of VSF in patients with skin diseases.

This evaluation was conducted under the guidance of dermatologists for a more objective evaluation of efficacy and was applied to patients who voluntarily requested the application of hzVSF.

The efficacy of the hzVSF was evaluated using 50 μl of 5 mg/ml hzVSF dissolved in PBS for each application, and the treatment effect was visually evaluated by the dermatologists.

EXAMPLE 8-1

Confirmation of Therapeutic Efficacy of VSF in Patients with Psoriasis

The psoriasis patient 1, who had psoriasis in his right leg, was applied with hzVSF to the knee lesion at the first visit (Aug. 17, 2016) and additionally applied with the same on Aug. 29, 2016 and Sep. 7, 2016.

As a result, when the knee lesion was examined on Sep. 15, 2016, a remarkable therapeutic effect was observed in the knee area where the hzVSF was applied as compared to other areas, and when the lesion area was examined again on Oct. 20, 2016, which was about one month after the fourth application on Sep. 15, 2016, it was confirmed that the lesion area with application was reduced by 90% or more (FIG. 21).

Therefore, it can be seen that the hzVSF prepared in Example 5 has an excellent therapeutic effect on skin diseases expressing VR, such as psoriasis.

Meanwhile, the psoriasis patient 2 had psoriasis on his back, and a biopsy was performed at the first visit (Aug. 19, 2016) to confirm the expression of VR, a receptor of hzVSF, by immunohistochemistry staining, thereby confirming the degree of VR expression. At the first visit, hzVSF was applied to the lesion on the back, and when the lesion area was examined five days later, on August 24, the degree of keratin formation and redness were decreased by 50% or more (FIG. 22). Therefore, an excellent treatment effect was confirmed even in patient 2.

EXAMPLE 8-2

Confirmation of Therapeutic Efficacy of VSF in Patients with Lichen Simplex Chronicus The patient 1 with lichen simplex chronicus had a lesion on the right leg. At the first visit (Aug. 7, 2016), hzVSF was applied to the lesion area of the shin once every 5 days. When the lesion area was examined on Aug. 22, 2016, which was after third application, it was confirmed that 70% or more of keratin formation and redness was suppressed (FIG. 23).

After that, hzVS was also applied to the lesion area of the ankle. Specifically, the shin area was applied with hzVS six times in total until Sep. 2, 2016, and examined a month later on Oct. 2, 2016. As a result, it was confirmed that the therapeutic effect was maintained without recurrence of the disease. The ankle was administered with the hzVS three times in total until Sep. 2, 2016, and examined a month later, on Oct. 2, 2016. As a result, it was confirmed that the lesion area was reduced by 50% or more (FIG. 23).

The patient 2 with lichen simplex chronicus had lesions on the ankles of both legs and applied with hzVSF to the lesions at the first visit (Aug. 7, 2016). When the lesion areas were examined on Sep. 30, 2016, which was about six weeks after the second application on Aug. 19, 2016, it showed a therapeutic effect to the extent that the lesion was almost cured. In particular, upon application of hzVSF, the area where keratin formation occurred almost disappeared, and it showed a therapeutic effect to the extent that the lesion area was reduced by 90% or more (FIG. 24).

The patient 3 with lichen simplex chronicus had lesions on the shin of the right leg, and received the first application of the hzVSF at the first visit (Sep. 17, 2016). When the lesion was examined on Sep. 19, 2016, which was two days later, it was confirmed that the lesion was decreased by 50% or more, confirming an excellent therapeutic effect of the hzVSF (FIG. 25).

EXAMPLE 8-3

Confirmation of Therapeutic Efficacy of VSF in Patients with Nummular Eczema

The patient with nummular eczema had lesions on the right calf and received the application of hzVSF twice daily from the first visit (Feb. 9, 2018). When the lesion area was examined on Feb. 23, 2018 and Mar. 26, 2018, it was visually confirmed that the lesion area was ameliorated, and the EASI score, which measures erythema, edema/tubercles/papules, abrasions and lichenification, improved from 11 to 4 at the third visit (after 45 days), compared to the first visit. Additionally, pruritus was also ameliorated from 10 to 5 at the third visit, thereby confirming a therapeutic effect (FIG. 26).

EXAMPLE 8-4

Quantitative Measurement of Therapeutic Efficacy of VSF in Patients with Skin Diseases HzVSF was applied twice daily to the lesion areas of patients with lichen simplex chronicus, nummular eczema, eczema, atopic dermatitis and psoriasis from the first visit, and the lesion areas were examined at the second and third visits. In the case of lichen simplex chronicus, the experiment was progressed for an average of 40 days from the first visit to the third visit, and the EASI score improved from 8.5 to 4 on average and the pruritus from 6.5 to 2.5. In the case of nummular eczema, the experiment was progressed for an average of 36 days from the first visit to the third visit, and the EASI score improved fr©m 8.3 to 3 on average and the pruritus from 8 to 3. In the case of eczema, the experiment was progressed for 35 days from the first visit to the third visit, and the EASI score improved from 5 to 1 and the pruritus from 5 to 2. In the case of atopic dermatitis, the experiment was progressed for 42 days from the first visit to the third visit, and the EASI score improved from 10 to 4, and the pruritus from 6 to 2. In the case of dermatitis, the experiment was progressed for 35 days from the first visit to the third visit, and the EASI score improved from 6 to 3 and the pruritus from 5 to 4. In the case of psoriasis, the experiment was progressed for an average of 26 days from the first visit to the third visit, and the PASI score improved from 8 to 3.6 on average and the pruritus from 6.3 to 2.6. From these results, it was confirmed that the lesion areas were visually ameliorated, and the EASI score, which measures erythema, edema/tubercles/papules, abrasions, and lichenification, and the PASI score, which measures erythema, thickness, and scaling, were improved in all skin diseases at the third visit as compared to the first visit. Additionally, it was confirmed that the pruritus was also ameliorated at the third visit, thereby confirming a therapeutic effect (FIGS. 27 and 28).

In conclusion, the VSF of the present invention, i.e., the hzVSF prepared in Examples 5 and 8, can exhibit an excellent therapeutic effect when applied to skin diseases expressing VR, such as psoriasis, lichen simplex chronicus, pityriasis rosea, herpes simplex, nummular eczema, molluscum contagiosum, verruca vulgaris, atopic dermatitis and allergic contact dermatitis. Therefore, it can be suggested that the VSF can effectively be used as a therapeutic composition for the prevention and treatment of skin diseases expressing VR, etc.

One of ordinary skill in the art would recognize that the present invention may be embodied in other specific forms without departing from its spirit or essential characteristics. The described embodiments are to be considered in all respects only as illustrative and not restrictive. The scope of the present invention is therefore indicated by the appended claims rather than by the foregoing description. All changes which come within the meaning and range of equivalency of the claims are to be embraced within the scope of the present invention.

The invention claimed is:

1. A method for treating a skin disease, comprising administering or applying a pharmaceutical composition comprising a humanized antibody or fragment thereof which specifically binds to a peptide of SEQ ID NO: 1 to an individual in need thereof,
   wherein the skin disease is selected from the group consisting of pityriasis rosea, lichen simplex chronicus, nummular eczema, eczema, molluscum contagiosum, psoriasis, verruca vulgaris, atopic dermatitis, and allergic contact dermatitis.

2. The method of claim 1, wherein the humanized antibody or fragment thereof comprises:
   a heavy chain variable region comprising a heavy chain CDR1 of SEQ ID NO: 2; a heavy chain CDR2 of SEQ ID NO: 3 or SEQ ID NO: 14; and a heavy chain CDR3 of SEQ ID NO: 4 or SEQ ID NO: 15; and
   a light chain variable region comprising a light chain CDR1 of SEQ ID NO: 5; a light chain CDR2 of SEQ ID NO: 6, SEQ ID NO: 16, SEQ ID NO: 17, or SEQ ID NO: 18; and a light chain CDR3 of SEQ ID NO: 7 or SEQ ID NO: 19.

3. A method for ameliorating a skin disease, comprising administering or applying a cosmetic composition comprising a humanized antibody or fragment thereof which specifically binds to a peptide of SEQ ID NO: 1 to an individual in need thereof wherein the skin disease is selected from the group consisting of pityriasis rosea, lichen simplex chronicus, nummular eczema, eczema, molluscum contagiosum, psoriasis, verruca vulgaris, atopic dermatitis, and allergic contact dermatitis.

4. The method of claim 2, wherein the humanized antibody or the fragment further comprises:
   a heavy chain variable region comprising a heavy chain framework region 1 (FR1) of SEQ ID NO: 20; a heavy chain FR2 of SEQ ID NO: 21; a heavy chain FR3 of SEQ ID NO: 22 or SEQ ID NO: 28; and a heavy chain FR4 of SEQ ID NO: 23; and a light chain variable region comprising a light chain FR1 of SEQ ID NO: 24; a light chain FR2 of SEQ ID NO: 25; a light chain FR3 of SEQ ID NO: 26; and a light chain FR4 of SEQ ID NO: 27.

* * * * *

UNITED STATES PATENT AND TRADEMARK OFFICE
CERTIFICATE OF CORRECTION

| | | |
|---|---|---|
| PATENT NO. | : 11,649,277 B2 | |
| APPLICATION NO. | : 16/636834 | |
| DATED | : May 16, 2023 | |
| INVENTOR(S) | : Yoon-Won Kim, Sungman Park and Min Soo Kim | |

It is certified that error appears in the above-identified patent and that said Letters Patent is hereby corrected as shown below:

In the Specification

In Column 2, Line 13, delete "tor" and insert --for--.

In Column 2, Line 52, after "SEQ" insert --ID--.

In Column 3, Line 6, after "SEQ" insert --ID--.

In Column 7, Line 17, delete "a." and insert --a--.

In Column 8, Line 44, after "SEQ" insert --ID--.

In Column 8, Line 60, after "SEQ" insert --ID--.

In Column 8, Line 60, delete "M" and insert --ID--.

In Column 8, Line 61, after "SEQ" insert --ID--.

In Column 8, Line 62, after "SEQ" insert --ID--.

In Column 8, Line 67, after "SEQ" insert --ID--.

In Column 9, Line 5, after "SEQ" insert --ID--.

In Column 9, Line 5, delete "and." and insert --and--.

In Column 9, Line 10, after "SEQ" insert --ID--.

In Column 9, Line 28, after "SEQ" insert --ID--.

Signed and Sealed this
Twenty-first Day of November, 2023

Katherine Kelly Vidal
*Director of the United States Patent and Trademark Office*

CERTIFICATE OF CORRECTION (continued)
U.S. Pat. No. 11,649,277 B2

In Column 9, Line 28, after "SEQ" insert --ID--.

In Column 9, Line 44, after "SEQ" insert --ID--.

In Column 9, Line 44, delete "CDRI," and insert --CDR1,--.

In Column 9, Line 49, delete "(I)" and insert --(l)--.

In Column 9, Line 49, delete "CDRI," and insert --CDR1,--.

In Column 10, Line 15, delete "hzVSV_var13." and insert --hzVSF_var13.--.

In Column 10, Line 37, delete "a." and insert --a--.

In Column 12, Line 5, delete "formlations," and insert --formulations,--.

In Column 12, Line 51, delete "tier" and insert --for--.

In Column 13, Line 21, delete "fbrmulation" and insert --formulation--.

In Column 13, Line 37, delete "buthylglycol" and insert --butylglycol--.

In Column 14, Line 36, delete "parent era" and insert --parenteral--.

In Column 15, Line 33, after "SEQ" insert --ID--.

In Column 15, Line 55, delete "Vsf" and insert --VSF--.

In Column 16, Lines 20-21 (Approx.), delete "gggcccttggtgaaagctgaggagacggtaactgagg" and insert --gggcccttggtggaagctgaggagacggtgactgagg--.

In Column 16, Line 62, delete "butler" and insert --buffer--.

In Column 17, Line 9 (Approx.), delete "(say)" and insert --(scFv)--.

In Column 17, Line 13 (Approx.), delete "SECT" and insert --SEQ--.

In Column 18, Line 39, delete "hsVSF_v13" and insert --hzVSF_v13--.

In Column 18, Line 54 (Approx.), delete "etc" and insert --etc.--.

In Column 20, Line 16 (Approx.), delete "NIDPYYGSTINA" and insert --NIDPYYGSTTYA--.

In Column 20, Line 19 (Approx.), delete "QUIFYGSPRT" and insert --QHFYGSPRT--.

CERTIFICATE OF CORRECTION (continued)
U.S. Pat. No. 11,649,277 B2

In Column 20, Line 42, delete "NO:23" and insert --NO: 23--.

In Column 20, Line 62, delete "viva" and insert --vivo--.

In Column 21, Line 15, delete "ETGNI ID" and insert --ETGNRAMD--.

In Column 21, Line 16, delete "2" and insert --2)--.

In Column 21, Line 23, Delete "SEQ" and insert --(SEQ--.

In Column 21, Line 27, Delete "SEQ" and insert --(SEQ--.

In Column 24, Line 10, Delete "KUL" and insert --KLH,--.

In Column 24, Line 34, Delete "activity" and insert --the reactivity--.

In Column 24, Line 53, Delete "YR" and insert --VR--.

In Column 25, Line 38, After "in" insert --xylene:--.

In Column 26, Line 48, Delete "issues" and insert --tissues--.

In Column 28, Line 45, Delete "fr©m" and insert --from--.